(12) United States Patent
Levesque et al.

(10) Patent No.: US 9,254,322 B2
(45) Date of Patent: *Feb. 9, 2016

(54) COMPOSITIONS COMPRISING E-SELECTIN ANTAGONISTS AND USES THEREFOR

(75) Inventors: Jean-Pierre Levesque, Yeerongpilly (AU); Ingrid Winkler, Yeerongpilly (AU)

(73) Assignee: The University of Queensland, St. Lucia (AU)

(*) Notice: Subject to any disclaimer, the term of this patent is extended or adjusted under 35 U.S.C. 154(b) by 901 days.

This patent is subject to a terminal disclaimer.

(21) Appl. No.: 12/747,324

(22) PCT Filed: Dec. 9, 2008

(86) PCT No.: PCT/AU2008/001810
§ 371 (c)(1),
(2), (4) Date: Oct. 12, 2010

(87) PCT Pub. No.: WO2009/073916
PCT Pub. Date: Jun. 18, 2009

(65) Prior Publication Data
US 2011/0020270 A1   Jan. 27, 2011

Related U.S. Application Data

(60) Provisional application No. 61/012,756, filed on Dec. 10, 2007.

(51) Int. Cl.
| | | |
|---|---|---|
| *A61K 38/08* | (2006.01) | |
| *A61K 38/10* | (2006.01) | |
| *A61K 38/18* | (2006.01) | |
| *A61K 39/395* | (2006.01) | |
| *A61K 45/06* | (2006.01) | |
| *A61K 31/00* | (2006.01) | |
| *A61K 31/7004* | (2006.01) | |
| *A61K 31/7016* | (2006.01) | |
| *A61K 31/702* | (2006.01) | |
| *A61K 31/7032* | (2006.01) | |
| *A61K 31/7056* | (2006.01) | |
| *A61K 38/19* | (2006.01) | |
| *C07K 7/06* | (2006.01) | |
| *C07K 7/08* | (2006.01) | |
| *C07K 16/28* | (2006.01) | |
| *C07K 14/475* | (2006.01) | |
| *C07K 14/54* | (2006.01) | |
| *C07K 14/705* | (2006.01) | |
| *C07K 7/00* | (2006.01) | |
| *A61K 38/04* | (2006.01) | |
| *A61K 38/17* | (2006.01) | |
| *A61K 39/00* | (2006.01) | |

(52) U.S. Cl.
CPC .............. *A61K 45/06* (2013.01); *A61K 31/00* (2013.01); *A61K 31/702* (2013.01); *A61K 31/7004* (2013.01); *A61K 31/7016* (2013.01); *A61K 31/7032* (2013.01); *A61K 31/7056* (2013.01); *A61K 38/1732* (2013.01); *A61K 38/193* (2013.01); *A61K 38/04* (2013.01); *A61K 38/08* (2013.01); *A61K 38/10* (2013.01); *A61K 38/178* (2013.01); *A61K 38/18* (2013.01); *A61K 39/3955* (2013.01); *A61K 2039/505* (2013.01); *C07K 7/00* (2013.01); *C07K 7/06* (2013.01); *C07K 7/08* (2013.01); *C07K 14/475* (2013.01); *C07K 14/54* (2013.01); *C07K 14/70564* (2013.01); *C07K 16/2854* (2013.01)

(58) Field of Classification Search
None
See application file for complete search history.

(56) References Cited

U.S. PATENT DOCUMENTS

| | | |
|---|---|---|
| 5,789,573 A | 8/1998 | Baker et al. |
| 5,830,871 A | 11/1998 | Wong et al. |
| 5,856,300 A | 1/1999 | Rittershaus et al. |
| 6,121,233 A | 9/2000 | Magnani et al. |
| 6,387,884 B1 | 5/2002 | Magnani et al. |
| 6,391,857 B1 | 5/2002 | Magnani et al. |
| 6,407,214 B1 | 6/2002 | Owens |
| 7,060,685 B2 | 6/2006 | Magnani et al. |
| 7,361,644 B2 | 4/2008 | Magnani et al. |
| 2002/0086356 A1 | 7/2002 | Tuschi et al. |
| 2002/0165178 A1* | 11/2002 | Schetter et al. ............... 514/44 |
| 2003/0073632 A1 | 4/2003 | Ciaccia et al. |

(Continued)

FOREIGN PATENT DOCUMENTS

| | | |
|---|---|---|
| WO | WO-94/25043 A1 | 11/1994 |
| WO | WO-95/31210 A1 | 11/1995 |

(Continued)

OTHER PUBLICATIONS

Komrokji et al. The colony stimulating factors: use to prevent and treat neutropenia and its complications. Expert Opin Biol Ther 4(12): 1897-1910, 2004.*

(Continued)

*Primary Examiner* — Bridget E Bunner
(74) *Attorney, Agent, or Firm* — Finnegan, Henderson, Farabow, Garrett & Dunner LLP

(57) ABSTRACT

This invention discloses the use of an E-selectin antagonist and a mobilizer of hematopoietic stem cells or progenitor cells in methods and compositions for treating or preventing immunocompromised conditions resulting from medical treatment. The present invention is particular relevant for prophylaxis and/or treatment of hematopoeitic disorders including neutropenia, agranulocytosis, anemia and thrombocytopenia in individuals receiving or proposed to receive treatments that target rapidly dividing cells or that disrupt the cell cycle or cell division.

26 Claims, 7 Drawing Sheets

(56) References Cited

U.S. PATENT DOCUMENTS

| | | |
|---|---|---|
| 2004/0067220 A1 | 4/2004 | Sykes |
| 2005/0181987 A1 | 8/2005 | Blaszczyk-Thurin et al. |
| 2005/0214283 A1 | 9/2005 | Sackstein |
| 2006/0194745 A1 | 8/2006 | Magnani et al. |
| 2007/0021378 A1 | 1/2007 | Varki |
| 2009/0053198 A1* | 2/2009 | Sackstein ............... 424/130.1 |
| 2011/0002881 A1 | 1/2011 | Levesque |
| 2011/0020270 A1 | 1/2011 | Levesque et al. |

FOREIGN PATENT DOCUMENTS

| | | |
|---|---|---|
| WO | WO 9640942 A1 | 12/1996 |
| WO | WO-98/46771 A2 | 10/1998 |
| WO | WO-99/65712 A2 | 12/1999 |
| WO | WO-00/50032 A1 | 8/2000 |
| WO | WO-03/032925 A2 | 4/2003 |
| WO | WO-03/097658 A2 | 11/2003 |
| WO | WO-2004/004636 A2 | 1/2004 |
| WO | WO-2004/094619 A2 | 11/2004 |
| WO | WO-2005/046597 A2 | 5/2005 |
| WO | WO-2005/051920 A2 | 6/2005 |
| WO | WO-2005/054264 A2 | 6/2005 |
| WO | WO-2006/062946 A2 | 6/2006 |
| WO | WO-2006/089106 A2 | 8/2006 |
| WO | WO-2006/127906 A1 | 11/2006 |
| WO | WO-2007/028050 A1 | 3/2007 |
| WO | WO 2008/011094 A2 | 1/2008 |
| WO | WO-2008/060378 A2 | 5/2008 |
| WO | WO-2008/100453 A1 | 8/2008 |

OTHER PUBLICATIONS

Bedard et al. Selectin inhibitors: a patent review. Expert Opin Ther Patents 20(6): 781-793, 2010.*

Cottler-Fox et al. Stem Cell Mobilization. Hematol Am Soc Hematol Educ Program, pp. 419-437, 2003.*

Frenette et al. Sulfated glycans induce rapid hematopoietic progenitor cell mobilization: evidence for selectin-dependent and independent mechanisms. Blood 96: 2460-2468, 2000.*

Katayama et al. PSGL-1 participates in E-selectin-mediated progenitor homing to bone marrow: evidence for cooperation between E-selectin ligands and alpha4 integrin. Blood 102: 2060-2067, 2003.*

Moore, M.A.S. Waking up HSCs: a new role for E-selectin. Nat Med 18(11): 1613-1614, 2012.*

Rood et al. E-selectin and very late activation antigen-4 mediate adhesion of hematopoietic progenitor cells to bone marrow endotherlium. Ann Hematol 79: 477-484, 2000.*

Sudhoff et al. Circulating Endothelial Adhesion molecules (sE-selectin, sVCAM-1, and sICAM-1) during rHuG-CSF-stimulated stem cell mobilization. J Hematotherapy & Stem Cell Res 11: 147-151, 2002.*

Winkler et al. Absence of E-selectin at the vascular niche delays hematopoietic stem cell turn-over. Blood 110(11): p. 609; Nov. 16, 2007.*

Winkler et al. Vascular niche E-selectin regulates hematopoietic stem cell dormancy, self renewal and chemoresistance. Nat Med 18(11): 1651-1657 (plus two pages of online methods), 2012.*

Demain et al. Natural products for cancer chemotherapy. Microbial Biotechnol 4(6): 687-699, 2011.*

"International Application Serial No. PCT/AU2008/001652, International Preliminary Report on Patentability issued Jun. 15, 2010", 6 pgs.

"International Application Serial No. PCT/AU2008/001652, Writen Opinion mailed Jan. 13, 2009", 5 pgs.

"International Application Serial No. PCT/AU2008/001810, International Preliminary Report on Patentability issued Jun. 15, 2010", 6 pgs.

"International Application Serial No. PCT/AU2008/001810, Written Opinion mailed Feb. 18, 2009", 5 pgs.

Ali, M., et al., "Polymers beearing sLE$^x$-mimetics are superior inhibitors of E-selectin-dependent leukocyte rolling in vivo", The FASEB Journal, 18(1), (2004), 152-154.

Alousi, A., et al., "Reduced-Intensity Conditioning Allogeneic Hematopoietic Stem Cell Transplantation", Clinical Advances in Hematology & Oncology, 5(7), (2007), 560-570.

Bennett, C.F., et al., "Inhibition of Endothelial Cell Adhesion Molecule Expression with Antisense Oligonucleotides", Journal of Immunology, 152(7), (1994), 3530-3540.

Bogden, A.E., et al., "Amelioration of Chemotherapy-Induced Toxicity by Cotreatment with AcSDKP, a Tetrapeptide Inhibitor of Hematopoietic Stem Cell Proliferation", Annals New York Academy of Sciences, 628, (1991), 126-139.

Bradford, G.B., et al., "Quiescence, cycling, and turnover in the primitive hematopoietic stem cell compartment", Experimental Hematology, 25, (1997), 445-453.

Burkhardt, K., et al., "The Significance of Adhesion Molecules in Nephrology", Artificial Organs, 20(5), (1996), 433-436.

Devereux, J., et al., "A comprehensive set of sequence analysis programs for the VAX", Necleic Acids Research, 12(1), (1984), 387-395.

Fruehauf, S., et al., "Protection of hematopoietic stem cells from chemotherapy-induced toxicity by multidrug-resistance 1 gene transfer", Recent Results in Cancer Research, 144, (Abstract Only), 1 pg., 1998.

Hamamoto, N., et al., "Inhibition of Dextram Sulphat Sodium (DSS)—induced Colitis in Mice by Intracolonically Administered Antibodies Against Adhesion Molecules (Endothelial Leucocyte Adhesion Molecule-1 (ELAM-1) or Intercellukar Adhesion Molecule-1 (ICAM-1))", Clinical Experimental Immunology, 117, (1999), 462-468.

Katayama, Y., et al., "CD 44 is a physiological E-selectin ligand on neutrophils", J. Exp. Med., 201(8), (2005), 1183-1189.

Khatib, A.-M., et al., "Inhibition of Hepatic Endothelial E-Selectin Expression by C-raf Antisense Oligonecleotides Blocks Colorectal Carcinoma Liver Metastasis", Cancer Research, 62(19), (2002), 5393-5398.

Kiel, M.J., et al., "Slam Family Receptors Distinguish Hematopoietic Stem and Progenitor Cells and Receal Endothelial Niches for Stem Cells", Cell, 121 (7), (2006), 1109-1121.

Maly, P., et al., "The $\alpha(1,3)$Fucosyltransferase Fuc-TVII Controls Leukocyte Trafficking through an Essential Role in L-, E-, and P-selection Ligand Biosynthesis", Cell 86(4), (1996), 643-653.

Muach, P., et al., "Hematopoietic Stem Cell Compartment: Acute and Late Effects of Radiation Therapy and Chemotherapy", Int. J.Radiation Oncology Biol. Phys., 315(5), (1995), 1319-1339.

McKenzie, J.L., et al., "Low rhodamine 123 retention identifies long-term human hematopoietic stem cells with the Lin$^-$CD34*CD38$^-$ population", Blood, 109, (2007), 543-545.

Plasterk, R. H. A.,et al., "The silence of the genes", Current Opinion in Genetics and Development, 10, (2000), 562-567.

Roberge, J. Y., et al., "A Strategy for a Convergent Synthesis of N-Linked Glycopeptides on a Solid Support", Science, 269(5221), (1995), 202-204.

Sanz, M.-J., et al., "Roflumilast inhibits leukocyte-endothelial cell interactions, expression of adhesion molecules and microvascular permeability", British Journal of Pharmacology, 152(4), (2007), 481-492.

Winkler, I.G., et al., "Adhesion to E-selectin promotes growth inhibition and apoptosis of human and murine hematopoeitic progenitor cells independent of PSGL-1", Blood, 104(5), (2004), 1685-1692.

USPTO Office Action mailed Mar. 21, 2012 in U.S. Appl. No. 12/746,894, filed Sep. 14, 2010 (8 pages).

USPTO Office Action mailed Nov. 27, 2012 in U.S. Appl. No. 12/746,894, filed Sep. 14, 2010 (10 pages).

USPTO Office Action mailed Jun. 7, 2013 in U.S. Appl. No. 12/746,894, filed Sep. 14, 2010 (11 pages).

USPTO Final Office Action mailed Jan. 27, 2014 in U.S. Appl. No. 12/746,894, filed Sep. 14, 2010 (8 pages).

USPTO Office Action mailed Jul. 23, 2015 in U.S. Appl. No. 12/746,894, filed Sep. 14, 2010 (14 pages).

USPTO Advisory Office Action mailed Jun. 18, 2014 in U.S. Appl. No. 12/746,894, filed Sep. 14, 2010 (4 pages).

(56) References Cited

OTHER PUBLICATIONS

Dagia, N.M., et al., "G-CSF Induses E-Selectin Ligand Expression on Human Myeloid Cells," Nat. Med., 10:1185-1190, (2006).
Definition of Allogenic, Medline Plus-Merriam-Webster Medical Dictionary (last accessed Jun. 3, 2013).
Definition of Sygeneic. Medline Plus-Merriam-Webster Medical Dictionary (last accessed Jun. 3, 2013).
Definition of Xenogenic. Medline Plus-Merriam-Webster Medical Dictionary (last accessed Jun. 3, 2013).
Kneuer, Carsten et al., "Selectins-Potential Pharmacological Targets," Drug Disc. Today, 31/22:1034-1040.
Kyriakides et al., (Surgery, Aug. 2000; 128(2):327-31).
Mulligan, et al. J. Clin. Invest., 88:1396-406, (1991).
Todderud et al., J. Pharmacol. Exp. Ther. 282: 1298-304, (1997).
Co-pending Application U.S. Appl. No. 12/746,894.

\* cited by examiner

COMPOSITIONS COMPRISING E-SELECTIN ANTAGONISTS AND USES THEREFOR

FIELD OF THE INVENTION

This invention relates generally to the use of an E-selectin antagonist and a mobilizer of hematopoietic stem cells or progenitor cells in methods and compositions for treating or preventing immunocompromised conditions resulting from medical treatment. The present invention is particular relevant for prophylaxis and/or treatment of hematopoeitic disorders including neutropenia, agranulocytosis, anemia and thrombocytopenia in individuals receiving or proposed to receive treatments that target rapidly dividing cells or that disrupt the cell cycle or cell division.

Bibliographic details of certain publications numerically referred to in this specification are collected at the end of the description.

BACKGROUND OF THE INVENTION

Hematopoiesis is an essential, lifelong process whereby highly specialized blood cells are generated from hematopoietic stem cells, including cells responsible for carbon dioxide and oxygen transport (erythrocytes), blood clotting (platelets), humoral immunity (B lymphocytes), cellular immunity (T lymphocytes), as well as cells which respond to foreign organisms and their products (granulocytes, monocytes, and macrophages).

Mature functional end cells and their immediate precursors have a limited life-span and a limited proliferative capacity and hence are not self-maintaining. Thus, these cells are continuously replaced from a pool of more primitive proliferating progenitor cells. The proliferation and self-renewal of these cells depend on stem cell factor (SCF). Glycoprotein growth factors regulate the proliferation and maturation of the cells that enter the blood from the marrow, and cause cells in one or more committed cell lines to proliferate and mature. Three more factors which stimulate the production of committed stem cells are called colony-stimulating factors (CSFs) and include granulocyte-macrophage CSF (GM-CSF), granulocyte CSF (G-CSF) and macrophage CSF (M-CSF).

Under normal conditions, senescent mature cells are continuously removed and replaced with newly generated cells. Under stress conditions, there may be an increased rate at which blood cells are destroyed or lost, or there may be a compromised capacity to replenish cells undergoing normal senescent attrition, resulting in depletion of erythrocytes (anemia), platelets (thrombocytopenia), leukocytes (leukopenia) including neutrophil granulocytes (neutropenia), and/or agranulocytosis (complete absence of white cells).

Radiation and chemotherapeutic treatment frequently produce severe reversible neutropenia or agranulocytosis, thrombocytopenia, and anemia. This effect comes about as the result of the toxicity of these treatment regimens on dividing hematopoietic stem cells and the consequent depletion of hematopoietic precursors and of the cells responsible for producing the required CSFs and hematopoietic potentiators. The depletion of hematopoietic precursors in the bone marrow associated with chemotherapy and irradiation sometimes results in life-threatening hemorrhagic and infectious complications. Severe suppression of hematopoiesis is a major factor in limiting chemotherapy use and dose escalation. Replacement of depleted blood cell types by transfusion is not always practical or desirable as it often affords only temporary improvement, is expensive, and is associated with risks of infection, fluid overload, and immune-mediated adverse reactions. Thus there has been intense interest in developing methods of using hematopoietic CSFs and potentiators to treat neutropenia, agranulocytosis, thrombocytopenia, and anemia.

In recent years three recombinant human hematopoietic growth factors became available for clinical use: erythropoietin (EPO) for stimulating the production of erythrocytes in the treatment of anemia, as well as G-CSF and GM-CSF for stimulating the production of neutrophils in the treatment of neutropenia. Apart from their effect on stimulating granulopoiesis, G-CSF and GM-CSF also mobilize large numbers of hematopoietic stem and progenitor cells (HSPCs) from the bone marrow into the peripheral blood, which further accelerates reconstitution of the hematopoietic system. HSPC mobilization is mediated by several factors including trans-acting signals that originate from the release of proteases including serine- and metallo-proteinases whose substrates include various molecules implicated in progenitor trafficking such as VCAM-1 membrane-bound Kit ligand, the c-Kit receptor, stromal-derived factor-1 (SDF-1 or CXCL12) and its cognate receptor CXCR4.

In work leading up to the present invention, it was discovered that E-selectin, a $Ca^{2+}$-dependent adhesion molecule expressed by bone marrow endothelial sinuses and on inflamed endothelial cells, regulates hematopoietic stem cell turn-over in the bone marrow. In particular, the present inventors determined that the absence of E-selectin at the endothelial niche significantly delays hematopoietic stem cell turn-over and that blocking E-selectin mediated adhesive interactions protects hematopoietic stem cells from medical treatments that target rapidly dividing cells, including myeloablative therapies such as radiation and chemotherapeutic treatments. Accordingly, it was proposed that E-selectin antagonists would be useful for treating or preventing immunocompromised conditions such as neutropenia, agranulocytosis, thrombocytopenia, and anemia, which result from medical treatment.

SUMMARY OF THE INVENTION

The present invention is predicated in part on the determination that mobilization of hematopoietic stem cells and progenitor cells by mobilizing agents (also referred to herein as "mobilizers" or "mobilizer of hematopoietic stem cells or progenitor cells") such as G-CSF is significantly enhanced by co-administration of an E-selectin antagonist. This in turn results in higher numbers of hematopoietic stem cells, progenitor cells and granulocytes such as neutrophils in peripheral blood when compared to administration of stem cell mobilizers alone. Based on this determination, the present inventors propose that concurrent administration of an E-selectin antagonist and a mobilizer of hematopoietic stem cells or progenitor cells is useful in compositions and methods for stimulating or enhancing hematopoiesis and for treating or preventing immunocompromised conditions that result from medical treatment, as described hereafter.

Accordingly, in one aspect, the present invention provides compositions for stimulating or enhancing hematopoiesis or for treating or preventing an immunocompromised condition in a subject, which condition results from exposure of the subject to a medical treatment. These compositions generally comprise an E-selectin antagonist and a mobilizer of hematopoietic stem cells or progenitor cells. In some embodiments, the mobilizer is characterized by its ability to decrease or block the expression, synthesis or function of CXCL12 or is characterized by its ability to block or antagonize CXCR4.

For example, illustrative mobilizers can be selected from: (1) small organic molecules (e.g., AMD3100); (2) polypeptides such as but not limited to: a cytokine (e.g., interleukin-1 (IL-1), interleukin-3 (IL-3), interleukin-6 (IL-6), interleukin-11 (IL-11), interleukin-7 (IL-7), and interleukin-12 (IL12)), a colony stimulating factor (e.g., granulocyte colony stimulating factor (G-CSF), granulocyte-macrophage colony stimulating factor (GM-CSF), macrophage colony stimulating factor (M-CSF), stem cell factor, FLT-3 ligand or a combination thereof), a protease (e.g., metalloproteinase (like MMP2 or MMP9) a serine protease, (like cathepsin G, or elastase) a cysteine protease (like cathepsin K) and a dipeptidyl peptidase-1 (DDP-1 OR CD26)) and a chemokine (e.g., CXCL12, IL-8, Mip-1α, and Groβ; (3) DNA or RNA molecules (e.g., a small interfering RNA (siRNA) molecule or an antisense molecule specific for CXCL12) and (4) carbohydrates (e.g., a sulfated carbohydrate such as but not limited to Fucoidan and sulfated dextran). In specific embodiments, the mobilizer is a colony stimulating factor such as G-CSF.

Non limiting examples of suitable E-selectin antagonists include small molecules, such as nucleic acids, peptides, polypeptides, peptidomimetics, carbohydrates, lipids or other organic (carbon containing) or inorganic molecules. Suitably, the E-selectin antagonist is selected from antigen-binding molecules that are immuno-interactive with E-selectin, peptides that bind to E-selectin and that block cell-cell adhesion, and carbohydrate or peptide mimetics of E-selectin ligands. In some embodiments, the E-selectin antagonist reduces the expression of an E-selectin gene or the level or functional activity of an expression product of that gene. For example, the E-selectin antagonist may antagonize the function of E-selectin, including reducing or abrogating the activity of at least one of its ligand-binding sites. Suitably, the E-selectin antagonist reduces the expression of the E-selectin gene or the level or functional activity of an expression product of that gene by at least 10%, 20%, 30%, 40%, 50%, 60%, 70%, 80%, 90% relative to the expression, level or functional activity in the absence of the agent. In some embodiments, the E-selectin antagonist is a selective E-selectin antagonist.

In accordance with the present invention, E-selectin antagonists are useful for enhancing a hematopoietic function (e.g., increasing the number of hematopoietic stem cells or progenitor cells and/or neutrophils in the peripheral blood) of a mobilizer of hematopoietic stem cells or progenitor cells. The E-selectin antagonists may be known or identified using any suitable screening assay. Accordingly, in a related aspect, the present invention provides screening methods for identifying agents that are useful for enhancing a hematopoietic function of the mobilizer. In some embodiments, the screening methods comprise contacting a preparation with a test agent, wherein the preparation comprises (i) a polypeptide comprising an amino acid sequence corresponding to at least a biologically active fragment of an E-selectin polypeptide, or to a variant or derivative thereof; or (ii) a polynucleotide comprising at least a portion of a genetic sequence (e.g., a transcriptional element) that regulates the expression of an E-selectin gene, which is operably linked to a reporter gene. A detected reduction in the level and/or functional activity of the polypeptide, or an expression product of the reporter gene, relative to a normal or reference level and/or functional activity in the absence of the test agent, indicates that the agent is useful for useful for treating or preventing the immunocompromised condition. In some embodiments, the E-selectin antagonist antagonizes the binding between E-selectin and an E-selectin ligand, as determined by: contacting an E-selectin and the ligand with the agent and measuring the binding of the E-selectin with the ligand. In these embodiments, agents can bind to the E-selectin or to the ligand and test positive when they reduce or abrogate the binding of the E-selectin with the ligand.

In another related aspect, the present invention provides methods of producing an agent that enhances a hematopoietic function of a mobilizer of hematopoietic stem cells or progenitor cells. These methods generally comprise: testing an agent suspected of antagonizing the function of E-selectin as broadly described above; and synthesizing the agent on the basis that it tests positive for the antagonism. Suitably, the method further comprises derivatizing the agent, and optionally formulating the derivatized agent with a pharmaceutically acceptable carrier and/or diluent, to improve the efficacy of the agent for enhancing the hematopoietic function of the mobilizer.

Another aspect of the present invention provides methods for enhancing a hematopoietic function of a mobilizer of hematopoietic stem cells or progenitor cells in a subject. These methods generally comprise administering concurrently to the subject a mobilizer of hematopoietic stem cells or progenitor cells and an E-selectin antagonist in an effective amount to enhance an hematopoietic function of the mobilizer (e.g., increasing the number of hematopoietic stem cells or progenitor cells and/or neutrophils in the peripheral blood). In a related aspect, the methods are useful for treating or preventing an immunocompromised condition in a subject, which condition results from exposure of the subject to a medical treatment. In these embodiments, the mobilizer and the E-selectin antagonist are administered in amounts effective for treatment or prevention the immunocompromised condition. Suitably, the immunocompromised condition is selected from neutropenia, agranulocytosis, thrombocytopenia, and anemia. In some embodiments, the methods further comprise identifying a subject having or at risk of developing the immunocompromised condition.

In some embodiments, the medical treatment targets rapidly dividing cells or disrupts the cell cycle or cell division. In illustrative examples of this type, the medical treatment is selected from chemotherapy and radiation therapy. Suitably, the medical treatment comprises treatment or prophylaxis of a cancer (e.g., a primary cancer or a metastatic cancer) or an autoimmune disease.

The mobilizer and the E-selectin antagonist are suitably administered in the form of one or more compositions each comprising a pharmaceutically acceptable carrier and/or diluent. The composition(s) may be administered by injection, by topical application or by the oral route including sustained-release modes of administration, over a period of time and in amounts which are effective for increasing the number of hematopoietic stem cells or progenitor cells and/or neutrophils in the peripheral blood.

In some embodiments, the mobilizer and the antagonist are administered simultaneously to the subject. In other embodiments the E-selectin antagonist is administered to the subject prior to administration of the mobilizer. In still other embodiments, the E-selectin antagonist is administered after administration of the mobilizer to the subject.

Similarly, the E-selectin antagonist and the mobilizer may be administered to the subject simultaneously, sequentially or separately with the medical treatment. In some embodiments, the concurrent administration of the E-selectin antagonist and the mobilizer is a prophylactic treatment (e.g., the subject is preparing to undergo chemotherapy or radiation treatment). In others, it is a therapeutic treatment (e.g., the subject has received at least one dose of chemotherapy or at least one radiation treatment).

In some embodiments, the methods may further comprise exposing the subject to an ancillary treatment that treats or prevents the immunocompromised condition. In illustrative examples of this type, the immunocompromised condition is anemia and the ancillary treatment may comprise administering to the subject an anemia medicament selected from recombinant erythropoietin (EPO), ferrous iron, ferric iron, vitamin B12, vitamin B6, vitamin C, vitamin D, calcitriol, alphacalcidol, folate, androgen, and carnitine. In other illustrative examples, the immunocompromised condition is thrombocytopenia and the ancillary treatment may comprise administering to the subject a thrombocytopenia medicament selected from a glucocorticoid, recombinant thrombopoietin (TPO), recombinant megakaryocyte growth and development factor (MGDF), pegylated recombinant MGDF and lisophylline. In still other illustrative examples, the immunocompromised condition is neutropenia and the ancillary treatment suitably comprises administering to the subject a neutropenia medicament selected from glucocorticoid, immunoglobulin, androgens, recombinant IFN-γ, and uteroferrin. In some embodiments, the ancillary treatment is administered to the subject simultaneously, sequentially or separately with the E-selectin antagonist and/or the mobilizer.

In some embodiments, the medical treatment is likely to expose the subject to a higher risk of infection. Accordingly, in these embodiments, the methods may further comprise administering simultaneously, sequentially or separately with the E-selectin antagonist and/or the mobilizer at least one anti-infective agent that is effective against an infection that develops or that has an increased risk of developing from the immunocompromised condition, wherein the anti-infective is selected from antimicrobials, antibiotics, antivirals, antifungals, anthelmintics, antiprotozoals and nematocides.

Typically, one or both of the E-selectin antagonist and the mobilizer are administered on a routine schedule, for example, every day, at least twice a week, at least three times a week, at least four times a week, at least five times a week, at least six times a week, every week, every other week, every third week, every fourth week, every month, every two months, every three months, every four months, and every six months.

In some advantageous embodiments, the concurrent administration of an E-selectin antagonist and a mobilizer of hematopoietic stem cells or progenitor cells (also referred to herein as the combination therapy of the present invention) is useful for treating or preventing hematopoeitic disorders such as neutropenia, agranulocytosis, thrombocytopenia, and anemia, which may result, for example, from myelosuppressive treatments that target rapidly dividing cells or that disrupt the cell cycle or cell division (e.g., chemotherapy or radiation therapy). It is proposed, therefore, that since administration of the combination therapy will reduce the risk of having or developing a hematopoietic disorder as a side effect of the myelosuppressive treatment, it is possible to administer higher therapeutic doses of a chemotherapeutic agent or radiation to a subject in order to kill or inhibit the growth or proliferation of a tumor or to treat or prevent an autoimmune disease in the subject. Accordingly, in yet another aspect, the present invention provides methods for increasing the dose of a medicament in a subject, wherein the medicament results or increases the risk of developing an immunocompromised condition. These methods generally comprise administering concurrently the medicament to the subject in a dose that ordinarily induces side effects (e.g., the development of the immunocompromised condition), together with a mobilizer of hematopoietic stem cells or progenitor cells and an E-selectin antagonist in amounts effective for inhibiting or preventing the induction of those side effects (e.g., in amounts effective for increasing the number of hematopoietic stem cells or progenitor cells and/or neutrophils in the peripheral blood).

In yet another aspect, the present invention provides pharmaceutical compositions for treating or preventing a disease (e.g., cancer or an autoimmune disease) that is treatable or preventable by a medical treatment that targets rapidly dividing cells or that disrupts the cell cycle or cell division (e.g., chemotherapy or radiation therapy). These compositions generally comprise an E-selectin antagonist, a mobilizer of hematopoietic stem cells or progenitor cells and at least one other agent selected from a chemotherapeutic agent (e.g., a cytotoxic agent), a radiosensitizing agent, an anemia medicament, a thrombocytopenia medicament, a neutropenia medicament, an agranulocytosis medicament and an anti-infective agent.

Still another aspect of the present invention provides the use of an E-selectin antagonist for enhancing a hematopoietic function of a mobilizer of hematopoietic stem cells or progenitor cells.

In yet another aspect, the present invention provides the use of an E-selectin antagonist and a mobilizer of hematopoietic stem cells or progenitor cells for treating or preventing an immunocompromised condition that results from a medical treatment. In some embodiments, the E-selectin antagonist and optionally the mobilizer are prepared or manufactured as medicaments for this purpose.

DETAILED DESCRIPTION OF THE INVENTION

1. Definitions

Figure 1:
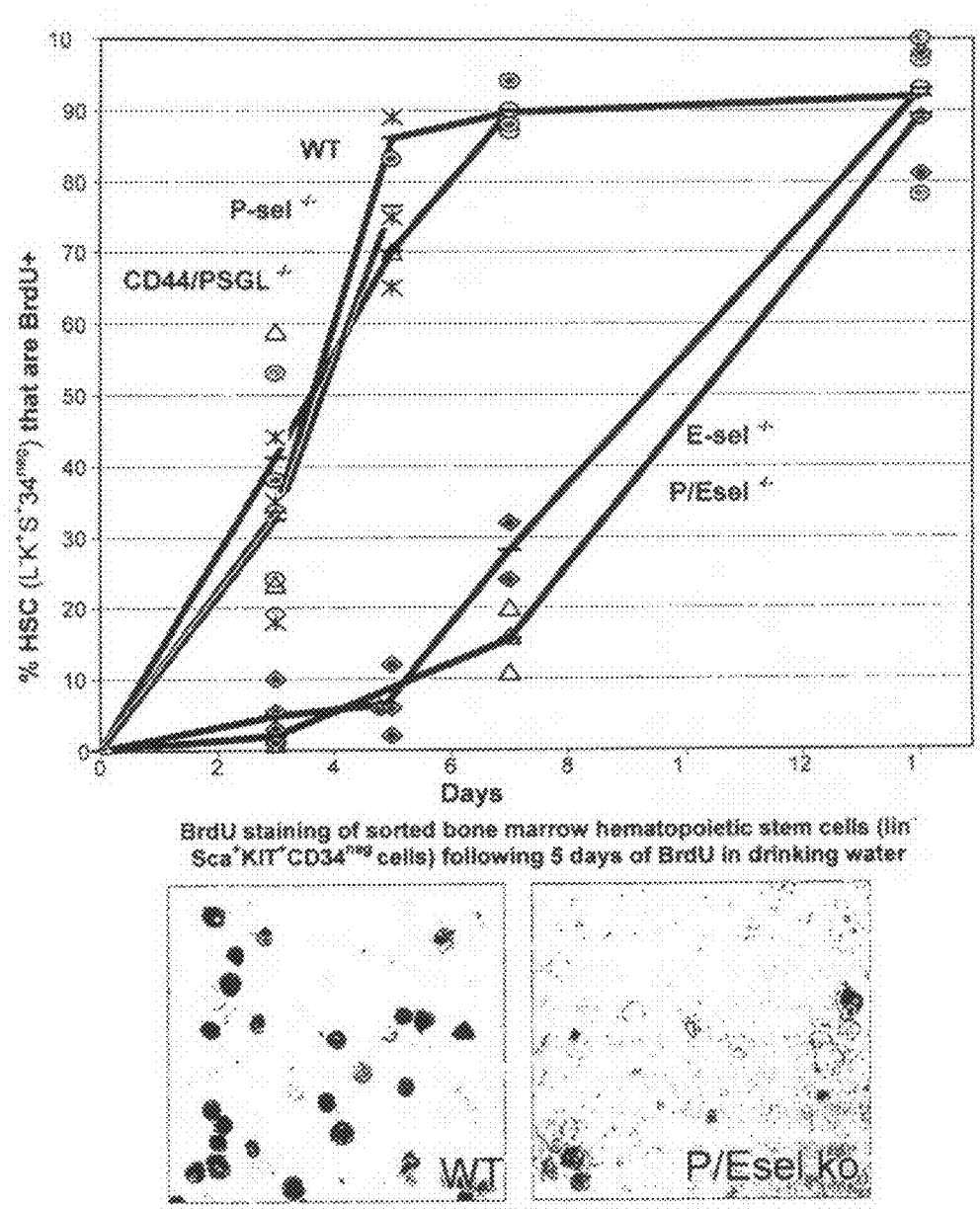
FIG. 1 is a graphical and photographic representation showing the kinetics of BrdU incorporation in vivo in hematopoietic stem cells isolated from the bone marrow of mice lacking P-selectin and/or E-selectin genes. The top panel shows the percentage of bone marrow LSK34-hematopoietic stem cells positive for BrdU in different knock-out strains and wild-type mice. The bottom panel shows a typical micrograph of BrdU staining in hematopoietic stem cells isolated from bone marrow of wild-type and P/E-selectin double knock-out mice fed for 5 days with BrdU.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. For example, an E-selectin antagonist may be administered together with a mobilizer of hematopoietic stem cells or progenitor cells in order to increase the numbers of hematopoietic stem cells, progenitor cells and/or granulocytes (e.g., neutrophils) in peripheral blood. In another example, an E-selectin antagonist and a mobilizer of hematopoietic stem cells or progenitor cells are administered together with another agent to enhance their effects or to ameliorate the effects of a medical treatment that causes or contributes to an immunocompromised condition. By "sequential" administration is meant a time difference of from seconds, minutes, hours or days between the administration of the two types of molecules or active agents. These molecules or active agents may be administered in any order. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. In certain embodiments, the E-selectin antagonist and the mobilizer are administered within about 60 minutes, about 50 minutes, about 40 minutes, about 30 minutes, about 20 minutes, about 10 minutes, about 5 minutes, or about 1 minute of each other or separated in time by about 1 hour, about 2 hours, about 4 hours, about 6 hours, about 10 hours, about 12 hours, about 24 hours, about 36 hours, or about 72 hours, or more. When administered contemporaneously, the agents are suitably administered at the same site on the subject. The term "same site" includes the exact location, but can be within about 0.5 to about 15 centimeters, usually from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell which is capable of producing and secreting the polypeptides referred to herein as well as a polynucleotide comprising a nucleotide sequence that encodes this polypeptide. Thus, the term "agent" extends to nucleic acid constructs including vectors such as viral or non-viral vectors, expression vectors and plasmids for expression in and secretion in a range of cells.

An "agranulocytosis medicament" as used herein refers to a composition of matter which reduces the symptoms related to agranulocytosis, prevents the development of agranulocytosis, or treats existing agranulocytosis.

An "anemia medicament" as used herein refers to a composition of matter which reduces the symptoms related to anemia, prevents the development of anemia, or treats existing anemia.

As used herein, the term "antagonist" means an agent that decreases or inhibits at least one function or biological activity of E-selectin (also known as CD62E, ELAM-1, LECAM-2). An E-selectin antagonist may be a compound which inhibits or decreases the interaction between E-selectin and another molecule, e.g., a target peptide, polypeptide, receptor, ligand or enzyme substrate. An antagonist may also be a compound that down-regulates expression of an E-selectin gene or which reduces the amount of expressed E-selectin protein present.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

Reference herein to "bacteria" or "bacterial infection" includes any bacterial pathogen including emerging bacterial pathogen of vertebrates. Representative bacterial pathogens include without limitation species of: *Acinetobacter, Actinobacillus, Actinomycetes, Actinomyces, Aeromonas, Bacillus, Bacteroides, Bordetella, Borrelia, Brucella* (brucellosis), *Burkholderia, Campylobacter, Citrobacter, Clostridium, Corynebacterium, Enterobacter, Enterococcus, Erysipelothrix, Escherichia, Francisella, Haemophilus, Helicobacter, Klebsiella, Legionella, Leptospira, Listeria, Micrococcus, Moraxella, Morganella, Mycobacterium* (tuberculosis), *Nocardia, Neisseria, Pasteurella, Plesiomonas, Propionibacterium, Proteus, Providencia, Pseudomonas, Rhodococcus, Salmonella, Serratia, Shigella, Staphylococcus, Stenotrophomonas, Streptococcus, Treponema, Vibrio* (cholera) and *Yersinia* (plague).

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

The term "differentiation" of hematopoietic stem cells and/or hematopoietic progenitors as used herein refers to both the change of hematopoietic stem cells into hematopoietic progenitors and the change of hematopoietic progenitors into unipotent hematopoietic progenitors and/or cells having characteristic functions, namely mature cells including erythrocytes, leukocytes (e.g., neutrophils) and megakaryocytes. Differentiation of hematopoietic stem cells into a variety of blood cell types involves sequential activation or silencing of several sets of genes. Hematopoietic stem cells typically choose either a lymphoid or myeloid lineage pathway at an early stage of differentiation.

By "effective amount," is meant the administration of an amount of active agent to a subject, either in a single dose or as part of a series or slow release system, which is effective for prevention or treatment. The effective amount will vary depending upon the health and physical condition of the subject and the taxonomic group of individual to be treated, the formulation of the composition, the assessment of the medical situation, and other relevant factors.

As used herein, the term "function" refers to a biological, enzymatic, or therapeutic function.

The terms "expression" or "gene expression" refer to either production of RNA message or translation of RNA message into proteins or polypeptides. By "expression vector" is meant any genetic element capable of directing the transcription of a polynucleotide contained within the vector and suitably the synthesis of a peptide or polypeptide encoded by the polynucleotide. Such expression vectors are known to practitioners in the art.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "hematopoietic stem cells" as used herein refers to multipotent stem cells that are capable of differentiating into all blood cells including erythrocytes, leukocytes and platelets. For instance, the term "hematopoietic stem cells" includes and encompasses those contained not only in bone marrow but also in umbilical cord blood derived cells.

The term "hematopoietic progenitors," which is used interchangeably with the term "hematopoietic precursors," refers to those progenitor or precursor cells which are differentiated further than hematopoietic stem cells but have yet to differentiate into progenitors or precursors of respective blood cell lineages (unipotent precursor cells). Thus, "progenitor cell(s)" or "precursor cell(s)" are defined as cells that are lineage-committed, i.e., an individual cell can give rise to progeny limited to a single lineage such as the myeloid or lymphoid lineage. They do not have self-renewal properties. They can also be stimulated by lineage-specific growth factors to proliferate. If activated to proliferate, progenitor cells have life-spans limited to 50-70 cell doublings before programmed cell senescence and death occurs. For example, "hematopoietic progenitors" as used herein include granulocyte/macrophage associated progenitors (colony-forming unit granulocyte, macrophage, CFU-GM), erythroid associated progenitors (burst-forming unit erythroid, BFU-E), megakaryocyte associated progenitors (colony-forming unit megakaryocyte, CFU-Mk), and myeloid associated stem cells (colony-forming unit mixed, CFU-Mix). Hematopoietic progenitor cells possess the ability to differentiate into a final cell type directly or indirectly through a particular developmental lineage. Undifferentiated, pluripotent progenitor cells that are not committed to any lineage are referred to herein as "stem cells." All hematopoietic cells can in theory be derived from a single stem cell, which is also able to perpetuate the stem cell lineage, as daughter cells become differentiated. The isolation of populations of mammalian bone marrow cell populations which are enriched to a greater or lesser extent in pluripotent stem cells has been reported (see for example, C. Verfaillie et al., J. Exp. Med., 172, 509 (1990), incorporated herein by reference).

"Homolog" is used herein to denote a gene or its product which is related to another gene or product by decent from a common ancestral DNA sequence.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

The term "immunocompromised" as used herein refers to a subject with an innate, acquired, or induced inability to develop a normal immune response. An immunocompromised subject, therefore, has a weakened or impaired immune system relative to one of a normal subject. A subject with a weakened or impaired immune system has an "immunodeficiency" or "immunocompromised condition," which is associated with a primary or secondary deficiency, induced or non-induced, in one or more of the elements of the normal immune defense system. An immunocompromised condition is commonly due to a medical treatment, e.g., radiation therapy, chemotherapy or other immunosuppressing treatment, such as induced by treatment with steroids, cyclophosphamide, azathioprine, methotrexate, cyclosporine or rapamycin, in particular in relation to cancer treatment or the treatment or prevention of transplant rejection. However, it will be understood that the phrase "risk of acquiring an immunocompromised condition resulting from a medical treatment" refers only to medical treatments that leads to or confers an immunocompromised condition, especially chemotherapy or other immunosuppressing treatment, such as induced by treatment with radiation, steroids, cyclophosphamide, azathioprine, methotrexate, cyclosporine or rapamycin. The presence of an immunocompromised condition in a subject can be diagnosed by any suitable technique known to persons of skill the art. Strong indicators that an immunocompromised condition may be present is when rare diseases occur or the subject gets ill from organisms that do not normally cause diseases, especially if the subject gets repeatedly infected. Other possibilities are typically considered, such as recently acquired infections—for example, HIV, hepatitis, tuberculosis, etc. Generally, however, definitive diagnoses are based on laboratory tests that determine the exact nature of the immunocompromised condition. Most tests are performed on blood samples. Blood contains antibodies, lymphocytes, phagocytes, and complement components—all of the major immune components that might cause immunodeficiency. A blood cell count will determine if the number of phagocytic cells or lymphocytes is below normal. Lower than normal counts of either of these two cell types correlates with an immunocompromised condition. The blood cells are also checked for their appearance. Occasionally, a subject may have normal cell counts, but the cells are structurally defective. If the lymphocyte cell count is low, further testing is usually conducted to determine whether any particular type of lymphocyte is lower than normal. A lymphocyte proliferation test may be conducted to determine if the lymphocytes can respond to stimuli. The failure to respond to stimulants correlates with an immunocompromised condition. Antibody levels and complement levels can also be determined for diagnosing the presence of an immunocompromised condition. However, it shall be understood that the methods of the present invention are not predicated upon diagnosing the absence of an immunocompromised condition in the subjects to be treated.

Reference herein to "immuno-interactive" includes reference to any interaction, reaction, or other form of association between molecules and in particular where one of the molecules is, or mimics, a component of the immune system.

Reference herein to a "infectious agent," "infectious organism," "microbe" or "pathogen" includes any one or more species or subspecies of bacterium, fungus, virus, algae, parasite, (including ecto- or endo-parasites) prion, oomycetes, slime, moulds, nematodes, mycoplasma and the like. The present invention is particularly suited to treating or preventing mixed infections by more than one microbe. Pathogenic algae include *Prototheca* and *Pfiesteria*. Also includes within the scope of these terms are prion proteins causing conditions such as Creutzfeldt-Jakob disease. As the skilled artisan will appreciate, pathogenicity or the ability of a classically non-pathogenic agent to infect a subject and cause pathology can vary with the genotype and expression profile of the infectious agent, the host and the environment. Fungal pathogens include without limitation species of the following genera: *Absidia, Acremonium, Aspergillus, Basidiobolus, Bipolaris, Blastomyces, Candida* (yeast), *Cladophialophora, Coccidioides, Cryptococcus, Cunninghamella, Curvularia, Epidermophyton, Exophiala, Exserohilum, Fonsecaea, Fusarium, Geotrichum, Histoplasma, Hortaea, Lacazia, Lasiodiplodia, Leptosphaeria, Madurella, Malassezia, Microsporum, Mucor, Neotestudina, Onychocola, Paecilomyces, Paracoccidioides, Penicillium, Phialophora, Piedraia, Piedra, Pityriasis, Pneumocystis, Pseudallescheria, Pyrenochaeta, Rhizomucor, Rhizopus, Rhodotorula, Scedosporium, Scopulariopsis, Scytalidium, Sporothrix, Trichophyton, Trichosporon* and *Zygomycete*. Pathogenic conditions include any deleterious condition that develops as a result of infection with an infectious organism.

By "isolated" is meant material that is substantially or essentially free from components that normally accompany it in its native state.

The term "lower alkyl" refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 2-methylpentyl, and the like. In some embodiments, the lower alkyl group is methyl or ethyl.

The term "lower alkoxy" refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 2-methyl-pentoxy, and the like. Usually, the lower alkoxy group is methoxy or ethoxy.

As used herein, a "mobilizer of hematopoietic stem cells or progenitor cells," "mobilizing agent" or "mobilizer" are used interchangeably to refer to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of hematopoietic stem cells or hematopoietic progenitor/precursor cells in the peripheral blood.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

A "neutropenia medicament" as used herein refers to a composition of matter which reduces the sympfoms related to neutropenia, prevents the development of neutropenia, or treats existing neutropenia.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

By "pharmaceutically acceptable carrier" is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

Pathogenic "protozoa" include, without limitation, *Trypanosoma, Leishmania, Giardia, Trichomonas, Entamoeba, Naegleria, Acanthamoeba, Plasmodium, Toxoplasma, Cryptosporidium, Isospora* and *Balantidium*.

Larger pathogenic "parasites" include those from the phyla Cestoda (tapeworms), Nematoda and Trematoda (flukes). Pathogenic trematodes are, for example, species of the following genera; *Schistosoma, Echinostoma, Fasciolopsis, Clonorchis, Fasciola, Opisthorchis* and *Paragonimus*. Cestode pathogens include, without limitation, species from the following orders; *Pseudophyllidea* (e.g., *Diphyllobothrium*) and *Cyclophyllidea* (e.g., *Taenia*). Pathogenic nematodes include species from the orders; *Rhabditida* (e.g., *Strongyloides*), *Strongylida* (e.g., *Ancylostoma*), *Ascaridia* (e.g., *Ascaris, Toxocara*), *Spirurida* (e.g., *Dracunculus, Brugia, Onchocerca, Wucheria*) and *Adenophorea* (e.g., *Trichuris* and *Trichinella*).

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The terms "polynucleotide variant" and "variant" refer to polynucleotides displaying substantial sequence identity with a reference polynucleotide sequence or polynucleotides that hybridise with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

As used herein, the terms "prevent," "prevented," or "preventing," when used with respect to the treatment of an immunocompromised condition (e.g., anemia, thrombocytopenia, agranulocytosis or neutropenia), refers to a prophylactic treatment which increases the resistance of a subject to developing the immunocompromised condition or, in other words, decreases the likelihood that the subject will develop the immunocompromised condition as well as a treatment after the immunocompromised condition has begun in order to reduce or eliminate it altogether or prevent it from becoming worse.

As used herein; a "repoiter gene" refers to any gene or DNA that expresses a product that is detectable by spectroscopic, photochemical, biochemical, enzymatic, immunochemical, electrical, optical or chemical means. The preferred reporter gene to which a promoter element is ligated is luciferase. Other reporter genes for use for this purpose include, for example, β-galactosidase gene (β-gal) and chloramphenicol acetyltransferase gene (CAT) Assays for expression produced in conjunction with each of these reporter gene elements are well-known to those skilled in the art.

The term "selective" refers to compounds that inhibit or display antagonism towards E-selectin without displaying substantial inhibition or antagonism towards another selectin (e.g., P-selectin). Accordingly, a compound that is selective for E-selectin exhibits an E-selectin selectivity of greater than about 2-fold, 5-fold, 10-fold, 20-fold, 50-fold or greater than about 100-fold with respect to inhibition or antagonism of another selectin (i.e., a selectin other than E-selectin). In some embodiments, selective compounds display at least 50-fold greater inhibition or antagonism towards E-selectin than towards P-selectin. In still other embodiments, selective compounds inhibit or display at least 100-fold greater inhibition or antagonism towards E-selectin than towards P-selectin. In still other embodiments, selective compounds display at least 500-fold greater inhibition or antagonism towards E-selectin than towards P-selectin. In still other embodiments, selective compounds display at least 1000-fold greater inhibition or antagonism towards E-selectin than towards P-selectin.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table A below. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP. Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

As used herein a "small molecule" refers to a composition that has a molecular weight of less than 3 kilodaltons (kDa), and typically less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, less than 1.5 kilodaltons, or even less than about 1 kDa.

"Stem cells" refer to cells, which are not terminally differentiated and are therefore able to produce cells of other types. Stem cells are generally divided into three types, including totipotent, pluripotent, and multipotent. "Totipotent stem cells" can grow and differentiate into any cell in the body, and thus can grow into an entire organism. These cells are not capable of self-renewal. In mammals, only the zygote and early embryonic cells are totipotent. "Pluripotent stem cells" are true stem cells, with the potential to make any differentiated cell in the body, but cannot contribute to making the extraembryonic membranes (which are derived from the trophoblast). "Multipotent stem cells" are clonal cells that self-renew as well as differentiate to regenerate adult tissues. "Multipotent stem cells" are also referred to as "unipotent" and can only become particular types of cells, such as blood cells or bone cells. The term "stem cells", as used herein, refers to pluripotent stem cells capable of self-renewal.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

"Subjects" contemplated in the present invention include any animal of commercial humanitarian or epidemiological interest including conveniently, primates, livestock animals (such as sheep, cows, horses, donkeys, pigs, fish and birds), laboratory test animals (such as mice, rabbits, guinea pigs and hamsters and the like), companion animals (such as dogs and cats), or captive wild animals. Avian species include poultry birds and caged avian species. In some embodiments the subject is a mammalian animal. In other embodiments, the subject is a human subject. The present composition and methods have applications in human and veterinary medicine, domestic or wild animal husbandry, cosmetic or aesthetic treatments for the skin after injury or surgery.

By "substantially complementary" it is meant that an oligonucleotide or a subsequence thereof is sufficiently complementary to hybridize with a target sequence. Accordingly, the nucleotide sequence of the oligonucleotide or subsequence need not reflect the exact complementary sequence of the target sequence. In a preferred embodiment, the oligonucleotide contains no mismatches and with the target sequence.

A "thrombocytopenia medicament" as used herein refers to a composition of matter which reduces the symptoms related to thrombocytopenia, prevents the development of thrombocytopenia, or treats existing thrombocytopenia.

By "treatment," "treat," "treated," "treating" and the like is meant to include both therapeutic and prophylactic treatment, including the administration of medicine or the performance of medical procedures with respect to a patient, for either prophylaxis (prevention) or to cure or reduce the extent of or likelihood of occurrence of the infirmity or malady or condition or event in the instance where the patient is afflicted. In some embodiments of the present invention, the treatments using the agents described may be provided to treat patients suffering from a cancerous condition or hyperproliferative disease, whereby the treatment of the disease with chemotherapy or irradiation therapy results in a decrease in bone marrow cellularity, thus making the patient more immuno-compromised and more prone therefore to acquiring infectious agents or diseases. Thus, the administration of the agents of the invention allows for enhanced mobilization of hematopoietic stem cells or progenitor cells from the bone marrow to the peripheral blood. In some embodiments, the treating is for the purpose of reducing or diminishing the symptoms or progression of a cancerous disease or disorder by allowing for the use of accelerated doses of chemotherapy or irradiation therapy.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

Reference herein to "a virus" includes any virus or viral pathogen or emerging viral pathogen. Viral families contemplated include Adenoviridae, African swine fever-like viruses, Arenaviridae (such as viral haemorrhagic fevers, Lassa fever), Astroviridae (astroviruses) Bunyaviridae (La Crosse), Caliciviridae (Norovirus), Coronaviridae (Corona virus), Filoviridae (such as Ebola virus, Marburg virus), Parvoviridae (B19 virus), Flaviviridae (such as hepatitis C virus, Dengue viruses), Hepadnaviridae (such as hepatitis B virus, Deltavirus), Herpesviridae (herpes simplex virus, varicella zoster virus), Orthomyxoviridae (influenza virus) Papovaviridae (papilloma virus) Paramyxoviridae (such as human parainfluenza viruses, mumps virus, measles virus, human respiratory syncytial virus, Nipah virus, Hendra virus), Picornaviridae (common cold virus), Poxyiridae (small pox virus, orf virus, monkey poxvirus) Reoviridae (rotavirus) Retroviridae (human immunodeficiency virus) Parvoviridae (parvoviruses) Papillomaviridae, (papillomaviruses) alphaviruses and Rhabdoviridae (rabies virus).

As used herein, underscoring or italicizing the name of a gene shall indicate the gene, in contrast to its protein product, which is indicated by the name of the gene in the absence of any underscoring or italicizing. For example, "E-selectin" shall mean the E-selecting gene, whereas "E-selectin" shall indicate the protein product or products generated from transcription and translation and alternative splicing of the "E-selectin" gene.

2. Abbreviations

CFC=colony-forming cells
HSC=hematopoietic stem cells
d=day
h=hour
s=seconds
i.v.=intravenous
i.p.=intraperitoneal
s.c.=subcutaneous 3. Compositions and Methods for Enhancing Hematopoietic Function The present invention is based in part on the surprising discovery that mobilization of hematopoietic stem cells by mobilizing agents such as G-CSF is significantly enhanced in the absence of E-selectin. This increased mobilization in turn results in higher numbers of hematopoietic stem cells, progenitor cells and granulocytes such as neutrophils in peripheral blood when compared to administration of stem cell mobilizers alone. Accordingly, the present invention relates to methods and compositions involving concurrent administration of an E-selectin antagonist and a mobilizer of hematopoietic stem cells or progenitor cells for stimulating or enhancing hematopoiesis and for the treatment or prophylaxis of immunocompromised conditions resulting from medical treatments that target rapidly dividing cells or that disrupt the cell cycle or cell division (e.g., myeloablative therapy). Thus, in some embodiments, the present invention provides compositions comprising an E-selectin antagonist and a mobilizer of hematopoietic stem cells or progenitor cells.

3.1 E-Selectin Antagonists

The E-selectin antagonist includes and encompasses any active compound that binds to E-selectin and that suitably inhibits the functional activity of E-selectin, including small molecules, such as nucleic acids, peptides, polypeptides, peptidomimetics, carbohydrates, lipids or other organic (carbon containing) or inorganic molecules. In some embodiments, the E-selectin antagonist is selected from antigen-binding molecules that are immuno-interactive with E-selectin, peptides that bind to E-selectin and that block cell-cell adhesion, as well as carbohydrate or peptide mimetics of E-selectin ligands. In some embodiments, the E-selectin antagonist reduces the expression of an E-selectin gene or the level or functional activity of an expression product of that gene. For example, the E-selectin antagonist may antagonize the function of E-selectin, including reducing or abrogating the activity of at least one of its ligand-binding sites. Alternatively, the E-selectin antagonist may act indirectly on E-selectin expression by modulating the level or functional activity of a regulator of E-selectin. For example, it is known that cytokine-dependent induction of E-selectin expression is mediated through cooperative signaling involving the Ras/Raf protein kinase pathway and that inhibition of C-raf antisense molecules can block E-selectin expression and E-selectin mediated cell-cell adhesion.

Illustrative agents for reducing or abrogating gene expression include, but are not restricted to, oligoribonucleotide sequences, including anti-sense RNA and DNA molecules and ribozymes, that function to inhibit the translation, for example, of E-selectin-encoding transcripts including E-selectin mRNA. Representative transcripts of this type include:

nucleotide sequences that comprise the sequence:

[SEQ ID NO: 1]
```
atgattgcttcacagtttctctcagctctcactttggtgcttctcattaaa
gagagtggagcctggtcttacaacacctccacggaagctatgacttatgatgaggccagtgc
ttattgtcagcaaaggtacacacacctggttgcaattcaaaacaaagaagagattgagtacc
taaactccatattgagctattcaccaagttattactggattggaatcagaaaagtcaacaat
gtgtgggtctgggtaggaacccagaaacctctgacagaagaagccaagaactgggctccagg
tgaacccaacaataggcaaaagatgaggactgcgtggagatctacatcaagagagaaaag
atgtgggcatgtggaatgatgagaggtgcagcaagaagaagcttgccctatgctacacagct
gcctgtaccaatacatcctgcagtggccacggtgaatgtgtagagaccatcaataattacac
ttgcaagtgtgaccctggcttcagtggactcaagtgtgagcaaattgtgaactgtacagccc
tggaatcccctgagcatggaagcctggtttgcagtcacccactgggaaacttcagctacaat
tcttcctgctctatcagctgtatagggggttacctgccaagcagcatggagaccatgcagtg
tatgtcctctggagaatggagtgctcctattccagcctgcaatgtggttgagtgtgatgctg
tgacaaatccagccaatgggttcgtggaatgtttccaaaaccctggaagcttcccatggaac
acaacctgtacatttgactgtgaagaaggatttgaactaatgggagcccagagccttcagtg
tacctcatctgggaattgggacaacgagaagccaacgtgtaaagctgtgacatgcagggccg
tccgccagcctcagaatggctctgtgaggtgcagccattcccctgctggagagttccccttc
aaatcatcctgcaacttcacctgtgaggaaggcttcatgttgcagggaccagcccaggttga
atgcaccactcaagggcagtggacacagcaaatcccagtttgtgaagctttccagtgcacag
ccttgtccaaccccgagcgaggctacatgaattgtcttcctagtgcttctggcagtttccgt
tatgggtccagctgtgagttctcctgtgagcagggttttgtgttgaagggatccaaaaggct
ccaatgtggccccacaggggagtgggacaacgagaagcccacatgtgaagctgtgagatgcg
atgctgtccaccagccccgaagggtttggtgaggtgtgctcattccctattggagaattc
acctacaagtcctcttgtgccttcagctgtgaggagggatttgaattacatggatcaactca
acttgagtgcacatctcagggacaatggacagaagaggttccttcctgccaagtggtaaaat
gttcaagcctggcagttccgggaaagatcaacatgagctgcagtggggagcccgtgtttggc
actgtgtgcaagttcgcctgtcctgaaggatggacgctcaatggctctgcagctcggacatg
tggagccacaggacactggtctggcctgctacctacctgtgaagctcccactgagtccaaca
ttcccttggtagctggactttctgctgctggactctccctcctgacattagcaccatttctc
ctctggcttcggaaatgcttacggaaagcaaagaaatttgttcctgccagcagctgccaaag
ccttgaatcagatggaagctaccaaaagccttcttacatcctttaa;
``` nucleotide sequences that share at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with SEQ ID NO: 1;

nucleotide sequences that hybridize under at least low, medium or high stringency conditions to SEQ ID NO: 1;

nucleotide sequences that encode the amino acid sequence:

[SEQ ID NO: 2]
MIASQFLSALTLVLLIKESGAWSYNTSTEAMTYDEASAYCQQRYTHLVAIQ
NKEEIEYLNSILSYSPSYYWIGIRKVNNVWVWVGTQKPLTEEAKNWAPGEPNNRQKDEDCVE
IYIKREKDVGMWNDERCSKKKLALCYTAACTNTSCSGHGECVETINNYTCKCDPGFSGLKCE
QIVNCTALESPEHGSLVCSHPLGNFSYNSSCSISCDRGYLPSSMETMQCMSSGEWSAPIPAC
NVVECDAVTNPANGFVECFQNPGSFPWNTTCTFDCEEGFELMGAQSLQCTSSGNWDNEKPTC

-continued

```
KAVTCRAVRQPQNGSVRCSHSPAGEFTFKSSCNFTCEEGFMLQGPAQVECTTQGQWTQQIPV

CEAFQCTALSNPERGYMNCLPSASGSFRYGSSCEFSCEQGFVLKGSKRLQCGPTGEWDNEKP

TCEAVRCDAVHQPPKGLVRCAHSPIGEFTYKSSCAFSCEEGFELHGSTQLECTSQGQWTEEV

PSCQVVKCSSLAVPGKINMSCSGEPVFGTVCKFACPEGWTLNGSAARTCGATGHWSGLLPTC

EAPTESNIPLVAGLSAAGLSLLTLAPFLLWLRKCLRKAKKFVPASSCQSLESDGSYQKPSYIL;
``` nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with SEQ ID NO: 2; and nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with SEQ ID NO: 2.

Anti-sense RNA and DNA molecules act to directly block the translation of mRNA by binding to targeted mRNA and preventing protein translation. In regard to antisense DNA, oligodeoxyribonucleotides derived from the translation initiation site, e.g., between − and + regions are preferred.

In some embodiments, anti-sense RNA and DNA molecules are used to directly block the translation of E-selectin mRNA by binding to targeted mRNA and preventing protein translation. In regard to antisense DNA, oligodeoxyribonucleotides derived from the translation initiation site, e.g., between −10 and +10 regions are desirable. Illustrative E-selectin antisense molecules are described, for example, by Bennett et al. (1994, J. Immunol., 152(7): 3530-3540) and by Baker et al. (U.S. Pat. No. 5,789,573). In other embodiments, C-raf antisense molecules can be used, which block C-raf expression, leading to reduced or abrogated E-selectin expression, as disclosed for example by Khatib et al. (2002, Cancer Res. 62(19):5393-5398).

In other embodiments, anti-E-selectin ribozymes are used for catalyzing the specific cleavage of E-selectin RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of target sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' or 3' ends of the molecule or the use of phosphorothioate or 2' O-methyl rather than phosphodiesterase linkages within the oligodeoxyribonucleotide backbone.

In other embodiments, RNA molecules that mediate RNA interference (RNAi) of an E-selectin gene or E-selectin transcript can be used to reduce or abrogate gene expression. RNAi refers to interference with or destruction of the product of a target gene by introducing a single stranded, and typically a double stranded RNA (dsRNA) that is homologous to the transcript of a target gene. Thus, in some embodiments, dsRNA per se and especially dsRNA-producing constructs corresponding to at least a portion of an E-selectin gene may be used to reduce or abrogate its expression. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for an E-selectin gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, Current Opinion in Genetics and Dev. 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are suitably at least about 100 nucleotides in length. RNA-encoding constructs that express a single RNA designed to form a dsRNA via internal folding are usually at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In other embodiments, RNA molecules of about 21 to about 23 nucleotides, which direct cleavage of specific mRNA to which they correspond, as for example described by Tuschl et al. in U.S. Patent Application Publication No. 20020086356, can be utilized for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

Illustrative RNAi molecules are commercially available from Santa Cruz Biotechnology, Inc. (Santa Cruz, Calif., USA).

In still other embodiments, the functional activity of an E-selectin polypeptide in the cell is inhibited through use of an anti-E-selectin antigen-binding molecule (e.g., a neutralizing antibody) as described for example by Owens et al. in U.S. Pat. No. 6,407,214. A range of anti-E-selectin antibodies are available commercially, for example from Abcam (Cambridge, UK), Beckman Coulter (Fullerton, Calif., USA), Bender MedSystems (Vienna, Austria), BioGenex (San Ramon, Calif., USA), Biomeda Corporation (Foster City, Calif., USA), BioVision, Inc. (Mountain View, Calif., USA), Cell Sciences (Canton, Mass., USA), Covance Research Products (Denver, Pa., USA), Celltech Chiroscience (Slough, UK; CDP850 humanized monoclonal antibody against E-selectin), GeneTex (San Antonio, Tex., USA), Hycult Biotechnology BV (Uden, The Netherlands), Protein Design Labs (Freemont, Calif., USA; SMART HuEP57C humanized monoclonal antibody), and R&D Systems (Minneapolis, Minn., USA).

In some embodiments, the E-selectin antagonist is selected from peptide inhibitors of E-selectin. Representative inhibitors of this type are disclosed, for example, by Cwirla et al. in International Publication WO 94/25043, which is expressly incorporated herein by reference in its entirety, and include peptides of from 9 to 20 amino acids having a core structure comprising:

WXXLWXXX' [SEQ ID NO: 3] where each amino acid is indicated by the one-letter amino acid code where specifically W is tryptophan, L is leucine, and X is any amino acid and X' is selected from the group consisting of M and Nle where M is methionine and Nle is norleucine. Specific peptides having this core structure comprise the sequence X, $X_2X_3WX_4X_5LWX_6X_7X_8X_9$ [SEQ ID NO: 4], wherein each residue can be independently selected as follows: X is H, E, or D; $X_2$ is I, M, or Nle; $X_3$ is T or S; $X_4$ is D, E, or L; $X_5$ is Q or E; X* is N or D; $X_7$ is L, M, V, or I; $X_g$ is M or Nle; and X, is N, S, Q.

In specific embodiments, the peptides are selected from the following sequences:

DGDITWDQLWDLMK; [SEQ ID NO: 5]

DYTWFELWDMMQ; [SEQ ID NO: 6]

DITWDELWKIMN; [SEQ ID NO: 7]

QITWAQLWNMMK; [SEQ ID NO: 8]

DYSWHDLWEMMS; [SEQ ID NO: 9]

DITWDQLWDLNleK; [SEQ ID NO: 10]

HITWDQLWRIMT; [SEQ ID NO: 11]

d-DITWDQLWDLMK; Dd-ITWDQLWDLMK; DId-TWDQLWDLMK; DITWd-DQLWDLMK; DITWDQLWDd-LMK; DITWDQLWDLMd-K; and HITWDQLWNVMN; [SEQ ID NO: 12]

ITWDQLWDLMK; (amino acids 4-14 of SEQ ID NO: 5)

DITWDQLWDLMK (amino acids 3-14 of SEQ ID NO: 5)

DGDTTWDQLWDLMK [SEQ ID NO: 13]

DYTWFELWDMMQ; [SEQ ID NO: 14]

DITWDELWKIMN; [SEQ ID NO: 15]

QITWAQLWNMMK; [SEQ ID NO: 16]

DYSWHDLWEMMS; [SEQ ID NO: 17]

DITWDQLWDLNleK; [SEQ ID NO: 18]

ATTWDQLWLLMS; [SEQ ID NO: 19]

ELTWDQLWVLMS; [SEQ ID NO: 20]

DVTWDQLWELMT; [SEQ ID NO: 21]

EVTWDQLWVMMQ; [SEQ ID NO: 22]

NLTWDQLWVLMS; [SEQ ID NO: 23]

EMSWLELWNVMN; [SEQ ID NO: 24]

TITWDQLWQMMS; [SEQ ID NO: 25]

ELSWDQLWNVMN; [SEQ ID NO: 26]

EMTWQELWNVMN; [SEQ ID NO: 27]

EMTWTELWNVMN; [SEQ ID NO: 28]

DMTWSQLWNVMN; [SEQ ID NO: 29]

EMTWLGLWNVMN; [SEQ ID NO: 30]

QITWMELWNLMN; [SEQ ID NO: 31]

ETTWDQLWEVMN; [SEQ ID NO: 32]

ETTWDQLWDVMN; [SEQ ID NO: 33]

DISWDQLWNVMN; [SEQ ID NO: 34]

QITWDQLWDLMK; [SEQ ID NO: 35]

EMTWDQLWNVMN; [SEQ ID NO: 36]

DITWDQLWNMMD; [SEQ ID NO: 37]

DITWNMLWNMMQ; [SEQ ID NO: 38]

DISWDDLWIMMN; [SEQ ID NO: 39]

DITWHQLWNLMN; [SEQ ID NO: 40]

EISWEQLWTMMN; [SEQ ID NO: 41]

DITWEQLWNMMN; [SEQ ID NO: 42]

EITWDQLWTLMT; [SEQ ID NO: 43]

DITWHQLWNLMN; [SEQ ID NO: 44]

DMTWDQLWIVMN; [SEQ ID NO: 45]

DITWEQLWNLMN; [SEQ ID NO: 46]

QITWYQLWNMMN; [SEQ ID NO: 47]

HISWHELWNLMQ; [SEQ ID NO: 48]

YTTWEQLWTMMN; [SEQ ID NO: 49]

HITWDQLWDLMQ; [SEQ ID NO: 50]

QITWDQLWDLMY; [SEQ ID NO: 51]

QITWDQLWNMMI; [SEQ ID NO: 52]

YITWEQLWNMMN; [SEQ ID NO: 53]

HITWDQLWDTMS; [SEQ ID NO: 54]

HITWDQLWEIMS; [SEQ ID NO: 55]

HITWDQLWALMT; [SEQ ID NO: 56]

HITWDQLWSLMS; [SEQ ID NO: 57]

HITWDQLWLMMS; [SEQ ID NO: 58]

HITWDQLWDLMQ; [SEQ ID NO: 59]

HITWDQLWWTMA; [SEQ ID NO: 60]

HITWDQLWLLMA; [SEQ ID NO: 61]

HITWDQLWMLMA; [SEQ ID NO: 62]

GSDSHTTWDELWNLMNPVLA; [SEQ ID NO: 63]

NWLDDITWDELWKIMNPSTA; [SEQ ID NO: 64]

ETDDHITWDQLWRTMTATMA; [SEQ ID NO: 65]

WTDTHITWDQLWHFMNMGEQ; [SEQ ID NO: 66]

GFGEAITWDQLWDMMNGEDA; [SEQ ID NO: 67]

NVAEQITWDQLWNLMSVGSS; [SEQ ID NO: 68]

GQTGLITWDMLWNLMNPVGE; [SEQ ID NO: 69]

GTGDHITWDQLWNLMINEKG; [SEQ ID NO: 70]

EYGRHITWDQLWQLMQSATA; [SEQ ID NO: 71]

MNNWHVSWEQLWDIMNGPPN; [SEQ ID NO: 72]

ESASHITWGQLWDLMNASEV; [SEQ ID NO: 73]

YWRGNITWDQLWNIMNSEYS; [SEQ ID NO: 74]

AGASHITWAQLWNMMNGNEG; [SEQ ID NO: 75]

GSWAHITWDQLWNLMNMGTQ; [SEQ ID NO: 76]

YGNSNITWDQLWSTMNRQTT; [SEQ ID NO: 77]

AHLPHISWDTLWHIMNKGEK; [SEQ ID NO: 78]

ESASHITWGQLWDLMNASEV; [SEQ ID NO: 79]

MNNWHVSWEQLWDIMNGPPN; [SEQ ID NO: 80]

GFGEAITWDQLWDMMNGEDA; [SEQ ID NO: 81]

WTDTHITWDQLWHFMNMGEQ; [SEQ ID NO: 82]

EMTWAELWTLME; [SEQ ID NO: 83]

DISWRQLWDIMN; [SEQ ID NO: 84]

EISWLGLWDIMN; [SEQ ID NO: 85]

DMTWHDLWTLMS; [SEQ ID NO: 86]

RGVWGGLWSMTW; [SEQ ID NO: 87]

EMTWQQLWWMQ; [SEQ ID NO: 88]

AEWTWDQLWHVMNPAESQ; [SEQ ID NO: 89]

RNMSWLELWEHMK; [SEQ ID NO: 90]

SQVTWNDLWSVMNPEVVN; [SEQ ID NO: 91]

HRAEWLALWEQMSP; [SEQ ID NO: 92]

YKKEWLELWHQMQA; [SEQ ID NO: 93]

RSLSWLQLWDQMK; [SEQ ID NO: 94]

KEQQWRNLWKMMS; [SEQ ID NO: 95]

KKEDWLALWRIMSVPD; [SEQ ID NO: 96]

RNMSWLELWEHMK; [SEQ ID NO: 97]

GRPTWNELWDMMQAP; [SEQ ID NO: 98]

KRKQWIELWNIMS; [SEQ ID NO: 99]

KTSEWNNLWKLMSQ [SEQ ID NO: 100]

HVSWEQLWDIMN [SEQ ID NO: 101]

KKEDWLALWRIMSV; [SEQ ID NO: 102]

HRAEWLALWEQMS; [SEQ ID NO: 103]

DGDITWDQLWDLNleK; [SEQ ID NO: 104]

QITWDQLWDLNleK; [SEQ ID NO: 105]

AETWDQLWHVMNPAESQ; [SEQ ID NO: 106]

DITWAQLWNNleNleN; [SEQ ID NO: 107]
and

DITWDQLWDLM (amino acids 3-13 of SEQ ID NO: 5); DITWDQLWDL (amino acids 3-12 of SEQ ID NO: 5); TWDQLWDLMK (amino acids 5-14 of SEQ ID NO: 5); and DITWDQLWDLMK-C(O)NH₂ (amino acids 3-14 of SEQ ID NO: 5) wherein d-indicates a D-amino acid and —C(O)NH₂ represents an amidated carboxy terminus [SEQ ID NO: 108].

Alternative peptide inhibitors of E-selectin can be selected from those disclosed by Barrett et al. in International Publication WO 95/31210, which is expressly incorporated herein by reference in its entirety, and which include peptides and peptide mimetics comprising: a molecular weight of less than about 2000 daltons, and a binding affinity to E-selectin as expressed by an $IC_{50}$-HL6O of no more than about 100 μM wherein from zero to all of the —C(O)NH— linkages of the peptide have been replaced by a linkage selected from the group consisting of a —CH₂OC(O)NR— linkage, a phosphonate linkage, a —CH₂S(O)₂N-linkage, a —CH₂NR— linkage, a —C(O)NR⁶— linkage, and a —NHC(O)NH— linkage where R is hydrogen or lower alkyl, and R⁶ is lower alkyl, further wherein the N-terminus of said peptide or peptide mimetic is selected from the group consisting of a —NRR¹ group, a —NRC(O)R group, a —NRC(O)OR group, a —NRS(O)₂R group, a —NHC(O)NHR group, a succinimide group, a benzyloxycarbonyl-NH— group, and a benzyloxycarbonyl-NH— group having from 1 to 3 substituents on the phenyl ring selected from the group consisting of lower alkyl, lower alkoxy, chloro, and bromo, where R and R¹ are independently selected from the group consisting of hydrogen and lower alkyl, and still further wherein the C-terminus of said peptide or peptide mimetic has the formula —C(O)R² where R² is selected from the group consisting of hydroxy, lower alkoxy, and —NR³R⁴ where R³ and R⁴ are independently selected from the group consisting of hydrogen and lower alkyl and where the nitrogen atom of the —NR³R⁴ group can optionally be the amine group of the N-terminus of the peptide so as to form a cyclic peptide and physiologically acceptable salts thereof Representative peptides and peptide mimetics disclosed in WO 95/31210 include peptides which comprise the following sequences:

YDDVCCELLF; [SEQ ID NO: 109]

DLPQWYTEWC; [SEQ ID NO: 110]

ENSHWCTCPC; [SEQ ID NO: 111]

DIEQDWVTWM; [SEQ ID NO: 112]

NEWCWPCRL; [SEQ ID NO: 1113]

DIWQDWVRWM; [SEQ ID NO: 114]

DLWQDWVTWM; [SEQ ID NO: 115]

DLWQDWVHWM; [SEQ ID NO: 116]

DIWQDWVTWM; [SEQ ID NO: 117]

DIWQDWVKWM [SEQ ID NO: 118]

DIWQDWVRWM-C(O)NH₂; [SEQ ID NO: 119]

DIWEDWVRWM; [SEQ ID NO: 120]

DIWQDWITWM; [SEQ ID NO: 121]

DITNal(1)DQLWDLMK-C(O)NH₂; [SEQ ID NO: 122]

DITWDQLNal(1)DLMK-C(O)NH₂; [SEQ ID NO: 123]

DITNal(2)DQLWDLMK-C(O)NH₂; [SEQ ID NO: 124]

-continued

DITWDQLNal(2)DLMK-C(O)NH$_2$; [SEQ ID NO: 125]

DITChaDQLWbLMK-C(O)NH$_2$; [SEQ ID NO: 126]

DITWDQLChaDLMK-C(O)NH$_2$; [SEQ ID NO: 127]

DITWDQLWDLM(OCH$_3$)K-C(O)NH$_2$; [SEQ ID NO: 128]

DITWDQLWDLM(SOCH$_3$)K-C(O)NH$_2$; [SEQ ID NO: 129]

DITWDQLWDLM(SO$_2$CH$_3$)K-C(O)NH$_2$; [SEQ ID NO: 130]

DITWDQLW-Aib-LMK-C(O)NH$_2$; [SEQ ID NO: 131]

DITWDQLW-Aib-LMK; [SEQ ID NO: 132]

DITW-Aib-QLWKLMK; [SEQ ID NO: 133]

DITW-Aib-QLWDLMK-C(O)NH$_2$; [SEQ ID NO: 134]

DITW-Aib-QLW-Aib-LMK-C(O)NH$_2$; [SEQ ID NO: 135]

DITW-Aib-QLWDLMK; [SEQ ID NO: 136]

DITW-Aib-QLW-Aib-LMK; [SEQ ID NO: 137]

AITWDQLWDLNleK; [SEQ ID NO: 138]

DATWDQLWDLNleK; [SEQ ID NO: 139]

DITADQLWDLNleK; [SEQ ID NO: 140]

DITWAQLWDLNleK; [SEQ ID NO: 141]

DITWDALWDLNleK; [SEQ ID NO: 142]

DITWDQAWDLNleK; [SEQ ID NO: 143]

DITWDQLADLNleK; [SEQ ID NO: 144]

DITWDQLWALNleK; [SEQ ID NO: 145]

DITWDQLWDANleK; [SEQ ID NO: 146]

DITWDQLWDLAK; [SEQ ID NO: 147]

DITWDQLWDLNleA; [SEQ ID NO: 148]

DITNal(1)DQLNal(1)DLMK-C(O)NH$_2$; [SEQ ID NO: 149]

DITWAQLNal(1)DLMK-C(O)NH$_2$; [SEQ ID NO: 150]

DITNal(1)AQLNal(1)DLMK-C(O)NH$_2$; [SEQ ID NO: 151]

DITNal(1)AQLNal(1)DLM(OCH$_3$)K-C(O)NH$_2$; [SEQ ID NO: 152]

DITWAQLWDLM(SO$_2$CH$_3$)K-C(O)NH$_2$; [SEQ ID NO: 153]

DITWAQLNal(1)DLM(SO$_2$CH$_3$)K-C(O)NH$_2$; [SEQ ID NO: 154]

DITNal(1)AQLWDLM(SO$_2$CH$_3$)K-C(O)NH$_2$; [SEQ ID NO: 155]

DITWAQLWDLM(OCH$_3$)K-C(O)NH$_2$; [SEQ ID NO: 156]

DITNal(1)AQLWDLMK-C(O)NH$_2$; [SEQ ID NO: 157]

DITNal(1)DQLWDLM(SO$_2$CH$_3$)K-C(O)NH$_2$; [SEQ ID NO: 158]

DITWDQLNal(1)DLM(SO$_2$CH$_3$)K-C(O)NH$_2$; [SEQ ID NO: 159]

DITWAQLWDLMK-C(O)NH$_2$; [SEQ ID NO: 160]

DITWAibQLWDLMK-C(O)NH$_2$; [SEQ ID NO: 161]

Ac-DITWDQLWKLMK; [SEQ ID NO: 162]

Ac-DITWDQLWDL-Nle-K-C(O)NH$_2$; [SEQ ID NO: 163]

Succ-ITWDQLWDLMK; [SEQ ID NO: 164]

Cbz-TWDQLWDLMK; [SEQ ID NO: 165]

Succ-ITWDQLWDLMK-C(O)NH$_2$; [SEQ ID NO: 166]

Cbz-DITWDQLWDLMK-C(O)NH$_2$; [SEQ ID NO: 167]

Ac-DITWDQLWDLMK-C(O)NH$_2$; [SEQ ID NO: 168]

Cbz-ITWDQLWDLMK; [SEQ ID NO: 169]

Succ-ITWDQLWAibLM(SO$_2$CH$_3$)K-C(O)NH$_2$; [SEQ ID NO: 170]

Succ-ITWAQLWAibLM(SO$_2$CH$_3$)K-C(O)NH$_2$; [SEQ ID NO: 171]

Succ-ITWAQLWDLM(SO$_2$CH$_3$)K-C(O)NH$_2$; [SEQ ID NO: 172]

Succ-rrWAQLWDLM(OCH$_3$)K-C(O)NH$_2$; [SEQ ID NO: 173]

Succ-ITWAQLWAibLM(OCH$_3$)K-C(O)NH$_2$; [SEQ ID NO: 174]

Succ-ITWDQLWAibLM(OCH$_3$)K-C(O)NH$_2$; [SEQ ID NO: 175]

Ac-DITWAQLWDLMK-C(O)NH$_2$; [SEQ ID NO: 176]

Ac-DITWDQLWAibLM(OCH$_3$)K-C(O)NH$_2$; [SEQ ID NO: 177]

Ac-DITWAQLWAibLM(SO$_2$CH$_3$)K-C(O)NH$_2$; [SEQ ID NO: 178]

```
Ac-DITWDQLWAibLM(SO₂CH₃)K-C(O)NH₂;                [SEQ ID NO: 179]

Ac-DITWAQLWDLM(SO₂CH₃)K-C(O)NH₂;                  [SEQ ID NO: 180]

Ac-DITWAQLWDLM(OCH₃)K-C(O)NH₂;                    [SEQ ID NO: 181]

Ac-DITWAQLWAibLM(OCH₃)K-C(O)NH₂;                  [SEQ ID NO: 182]

Ac-DITWDQLWAibLM(OCH₃)K-C(O)NH₂;                  [SEQ ID NO: 183]

DITWAQLWAibLM(OCH₃)K-C(O)NH₂;                     [SEQ ID NO: 184]

DITWAQLWAibLM(SO₂CH₃)K-C(O)NH₂;                   [SEQ ID NO: 185]

DITWDQLWAibLM(OCH₃)K-C(O)NH₂;                     [SEQ ID NO: 186]

WDLMK-C(O)NH₂;                                    [SEQ ID NO: 187]

Cbz-WDLM-C(O)NH₂;                                 [SEQ ID NO: 188]

Cbz-QLWD-C(O)NH₂;                                 [SEQ ID NO: 189]

Cbz-QLWDLM-C(O)NH₂;                               [SEQ ID NO: 190]

Cbz-ITWDQ-C(O)NH₂;                                [SEQ ID NO: 191]

Cbz-TWDQLW-C(O)NH₂;                               [SEQ ID NO: 192]

Cbz-WDQLWD-C(O)NH₂;                               [SEQ ID NO: 193]

Cbz-ITWAQ-C(O)NH₂;                                [SEQ ID NO: 194]

Cbz-ITWDQL-C(O)NH₂;                               [SEQ ID NO: 195]

N-Cbz, N-Me-ITW-C(O)NH₂;                          [SEQ ID NO: 196]

Cbz-rr-[(Me)(DL)W]-C(O)NH₂;                       [SEQ ID NO: 197]

N-Cbz, N-Me-ITWDQ-C(O)NH₂;                        [SEQ ID NO: 198]

Cbz-ITW-N-Me-DQ-C(O)NH₂;                          [SEQ ID NO: 199]

Cbz-rr-N-Me-WDQ-C(O)NH₂;                          [SEQ ID NO: 200]

Cbz-I-(N-Me T)WDQ-C(O)NH₂;                        [SEQ ID NO: 201]

Cbz-I-(N-Me-T)W-C(O)NH₂;                          [SEQ ID NO: 202]

Cbz-IT-[(aMe)(DL)W]-DQ-C(O)NH₂;                   [SEQ ID NO: 203]

Cbz-N-Me-I-T-[(aMe)(DL)W]-C(O)NH₂;                [SEQ ID NO: 204]

DITWDELWTLML;                                     [SEQ ID NO: 205]

HLTWDQLWRIMN;                                     [SEQ ID NO: 206]

HITWDQLWNLMN;                                     [SEQ ID NO: 207]

HITWDQLWDIMN;                                     [SEQ ID NO: 208]

HVTWELLWDIMN;                                     [SEQ ID NO: 209]

HITWGQLWDLMN;                                     [SEQ ID NO: 210]

HITWEQLWDLMN;                                     [SEQ ID NO: 211]

EITWFELWEWME;                                     [SEQ ID NO: 212]

MASWVLLWPYMG-C(O)NH₂;                             [SEQ ID NO: 213]

DITWAQLWNIMN,                                     [SEQ ID NO: 214]
``` where Aib is aminoisobutryic acid, Nal(1) is α-naphthylalanine, Nal(2) is β-naphthylalanine, M(SO₂CH₃) is methionine sulfone, M(OCH₃) is O-methylmethione, Cbz is benzoxycarbonyl, Ac is acetyl, Succ is succinimidyl, and N-Me is a methylated nitrogen on the amine or amide group as designated therein.

Alternative peptide inhibitors of E-selectin are disclosed for example in US Pat. Appl. Pub. No 2005/0181987, which is expressly incorporated herein by reference in its entirety, and which discloses several peptido-mimetics which mimic the topography of the E-selectin ligand: ASAVNLYIPTQE [SEQ ID NO: 215], VYLAPGRISRDY [SEQ ID NO: 216], VYLAPGRFSRDY [SEQ ID NO: 217], CTSHWGVLSQRR [SEQ ID NO: 218], RVLSPESYLGPS [SEQ ID NO: 219], RVLSPESYLGPA [SEQ ID NO: 220], VGNGVLMGRRG [SEQ ID NO: 221], RVLSPESYLGPA [SEQ ID NO: 222], GNCRYIGLRQFG [SEQ ID NO: 223], DIRVEPGGGYTH [SEQ ID NO: 224], APIHTYTGRARG [SEQ ID NO: 225], and RHTCVRSCGHDR [SEQ ID NO: 226].

In other embodiments, the peptide inhibitors are glycopeptide molecules. Representative molecules of this type are disclosed, for example, by Cummings et al. in International Publication WO 99/065712, which is expressly incorporated herein by reference in its entirety. In particular, this reference discloses glycosulfopeptides (GSPs) which have one or more sulfated tyrosine residues and a glycan linked to the peptide, the glycan desirably including a sialyl Lewis$^x$ group or a sialyl Lewis$^a$ group. Illustrative GSPs of this type have an O-glycan comprising a β1,6 linkage to a GalNAc. Several exemplary GSPs are disclosed including compounds represented by the formula:

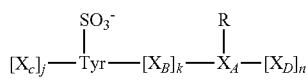

wherein: Tyr is a tyrosine residue; $SO_3^-$ is a sulfate group attached to the tyrosine residue; $X_A$ is an N- or O-linking amino acid residue; R is a sialylated, fucosylated, N-acetyl-lactosamino glycan in O- or N-linkage to $X_A$; $X_B$, $X_C$, and $X_D$ are amino acid residues; and j, k and n are each from 0 to 12, wherein each amino acid sequence $[X_B]j[X_C]_k$, or $[X_D]_n$ comprises from 0 to 12 amino acid residues. In illustrative examples of this type, the compound comprises no more than 38 amino acids.

In specific embodiments, X comprises one or two sulfated tyrosine residues; j=0 to 10, k=0 to 5, and n=0 to 10; R is selected from the group consisting of $R_1$-$R_{15}$; j=0, k=0 to 5 and n=0; $X_B$ comprises proline; $X_C$ comprises tyrosine; the compound further comprises at least one additional sialylated, fucosylated O-glycan linked to an amino acid residue; $X_A$ is an O-linking amino acid; the O-linking amino acid residue is serine or threonine; $X_A$ is an N-linking amino acid; R comprises a β1,6 linkage to a GAlNAc; and/or R is core-2 based.

In other embodiments, suitable GSPs are selected from the compounds disclosed by Cummings et al in International Publication No. WO 2003/032925, which is expressly incorporated herein by reference in its entirety. Representative GSPs disclosed in the reference have the formula:

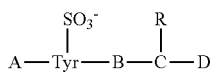

wherein: Tyr is a tyrosine residue; C is an N-, S-, or O-linking amino acid residue; R is a sialylated, fucosylated, N-acetyllactosaminoglycan in O-, S-, or N-linkage to C; A, B, and D are amino acid sequences each comprising from 0 to 12 amino acid residues. In specific embodiments C is serine, threonine, hydroxyproline, tyrosine, lysine, hydroxylysine, methionine, cysteine, asparagine or glutamine; the glycosulfopeptide is conjugated, linked or complexed to a polymeric carrier molecule (e.g., PEG); A of the glycosulfopeptide comprises $X_1$-$X_2$-$X_3$-$X_4$-$X_5$, wherein $X_1$ and $X_3$ are sulfated tyrosines and $X_2$, $X_4$ and $X_5$ are amino acids selected from the group consisting of Ala, Asp, Cys, Glu, Phe, Gly, His, Ile, Lys, Leu, Met, Asn, Pro, Gly, Org, Ser, Thr, Val, Trp, and Tyr, or is absent; B of the glycosulfopeptide is $X_6$-$X_7$-$X_8$-$X_9$-$X_{10}$ wherein each of $X_6$-$X_{10}$ is an amino acid selected from the group consisting of Ala, Asp, Cys, Glu, Phe, Gly, His, Ile, Lys, Leu, Met, Asn, Pro, Gly, Org, Ser, Thr, Val, Trp, and Tyr, or is absent; D of the glycosulfopeptide is $X_{11}$-$X_{12}$-$X_{13}$-$X_{14}$-$X_{15}$-$X_{16}$ wherein each of $X_{11}$-$X_{16}$ is an amino acid selected from the group consisting of Ala, Asp, Cys, Glu, Phe, Gly, His, Ile, Lys, Leu, Met, Asn, Pro, Gly, Org, Ser, Thr, Val, Trp, and Tyr, or is absent.

In still other embodiments, the peptide inhibitor of E-selectin is Ac-TWDQLWDLMK-CONH$_2$ as disclosed for example by Rinnbauer et al. (2003, Glycobiology 13(6). 435-443), which is expressly incorporated herein by reference in its entirety.

In still other embodiments, the E-selectin antagonist is selected from carbohydrate inhibitors of E-selectin. In illustrative examples of this type, the carbohydrate inhibitor is selected from the compounds described by Wong et al. in U.S. Pat. No. 5,830,871, which is expressly incorporated herein by reference in its entirety. In some embodiments, these compounds are represented by any one of the following formulae:

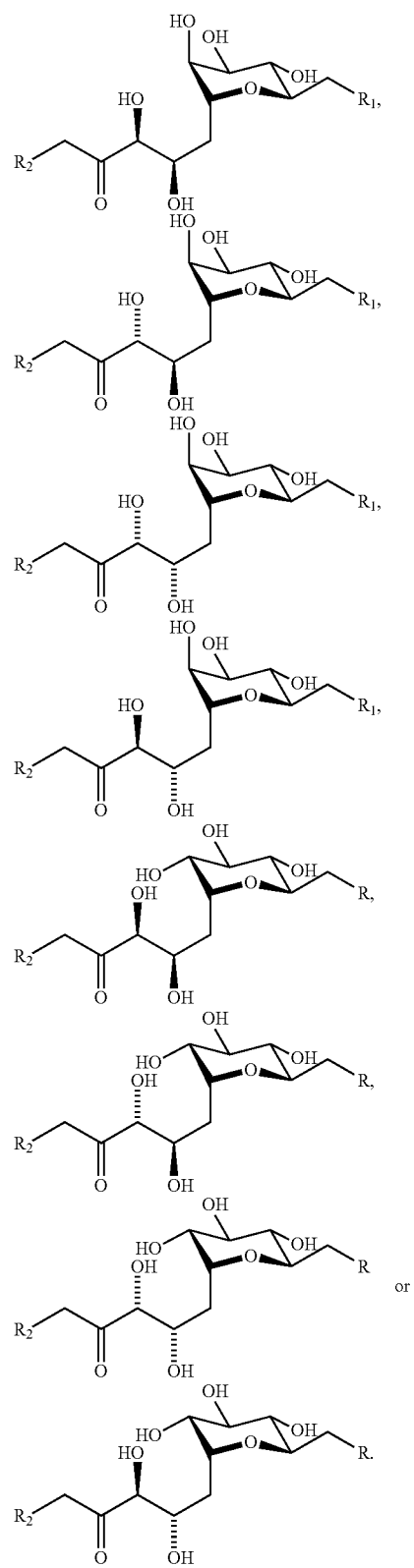

In the above formulas, $R_1$ is a radical selected from the group consisting of —H, —OH, —O—$C_1$-$C_6$, —OBn, —$N_3$, —$OSO_3^{2-}$, —OCOCH$_2$CH$_2$CONHCH(CH$_2$CO$_2$H)CO$_2$H, and —NHR'. R' is a radical selected from the group consisting of alkyl($C_1$-$C_6$), acyl, decanoyl, phenylacetyl, and —COCH$_2$CH$_2$CO$_2$H. R$_2$ is a radical selected from the group consisting of —CH$_2$PO$_3{}^{2-}$ and —OPO$_3{}^{2-}$.

Other embodiments of the carbohydrate inhibitors disclosed by Wong et al., are represented by the following formulae:

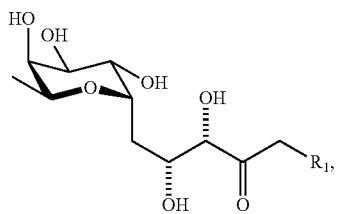

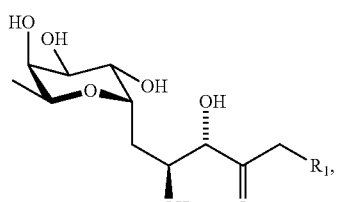

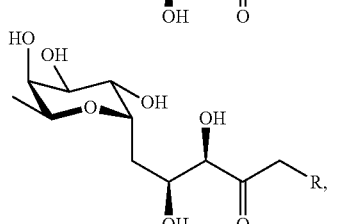

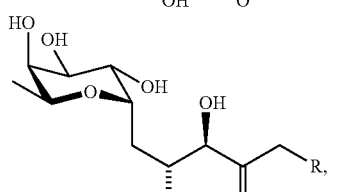

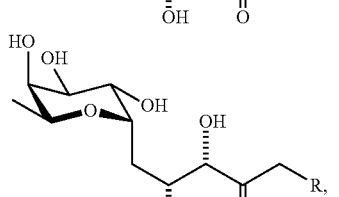

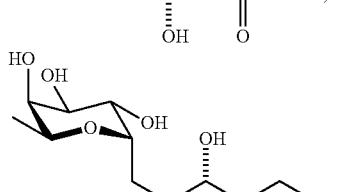, or

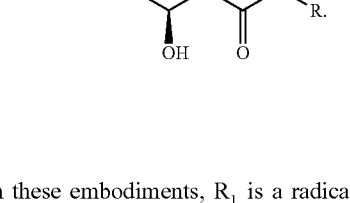.

In these embodiments, R$_1$ is a radical selected from the group consisting of —CH$_2$POPO$_3{}^{2-}$ and —OPOPO$_3{}^{2-}$.

Still other embodiments of the carbohydrate inhibitors disclosed by Wong et al., are represented by the following formulae:

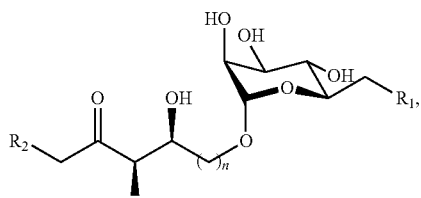

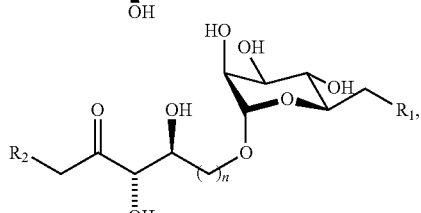

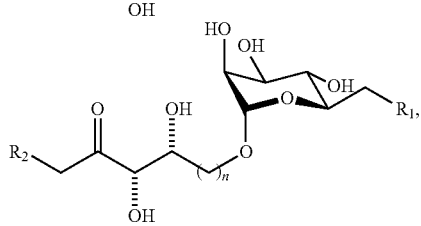

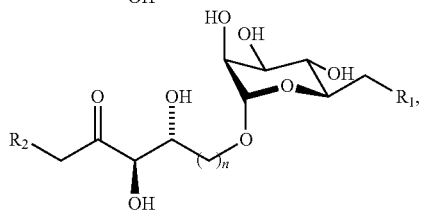

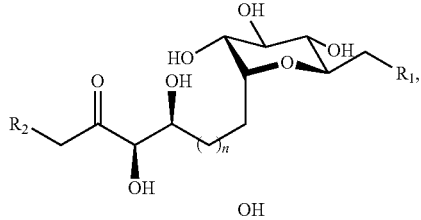

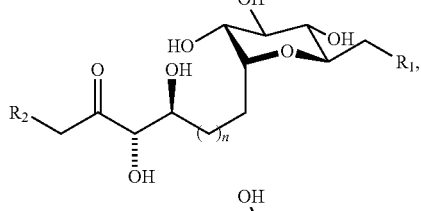

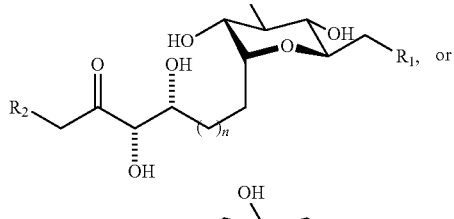, or

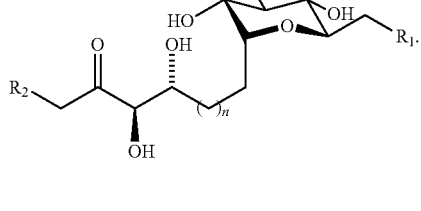.

In the above formulas: R$_1$ is a radical selected from the group consisting of —H, —OH, —O-alkyl(C$_1$-C$_6$), —OBn, —N$_3$, —OPOPO$_3{}^{2-}$, —OCOCH$_2$CH$_2$CONHCH (CH$_2$CO$_2$H)CO$_2$H, and —NHR'; R' is a radical selected from the group consisting of alkyl(C$_1$-C$_6$), acyl, decanoyl, phenylacetyl, and —COCH$_2$CH$_2$CO$_2$H; R$_2$ is a radical selected from the group consisting of —CH$_2$PO$_3^{2-}$ and OPO$_3^{2-}$; and "n" runs from 1 to 4.

In some embodiments, the carbohydrate inhibitor is a derivative of sialyl-Lewis$^x$ (SLe$^x$) or sialyl-Lewis$^a$ (SLe$^a$), illustrative examples of which are described by Thoma et al. in International Publication No. WO 98/06730, which is expressly incorporated herein by reference in its entirety.

In other illustrative examples, the carbohydrate inhibitor is selected from the oligosaccharide or glycomimetic compounds described by Magnani et al. in International Publication Nos. WO 2008/100453 and WO 2008/060378, which are expressly incorporated herein by reference in their entirety. These compounds are represented by the formula:

wherein:

R$^1$=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, OH, or NHX where X=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; C(=O)OX, alkanyl substituted with C(=O) OX, C(=O)NHX, alkanyl substituted with C(=O)NHX, where X=C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; O(=O)X, OX, NHX, NH(=O)X, where X=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH;

R$^2$=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, OH$_1$ or NHX where X=H$_1$C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; —C(=O)OX where X is C$_1$-C$_8$ alkanyl, C$_1$-C$_8$ alkenyl, C$_1$-C$_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; O(=O)X, OX, NHX, NH(=O)X, where X=H$_1$C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; with the proviso that R$^1$ and R$^2$ are not both H;

the cyclohexane derivative is at least attached to the oligosaccharide or glycomimetic compound at an OH, R$^1$ or R$^2$.

In some embodiments, the oligosaccharide or glycomimetic compounds comprise:

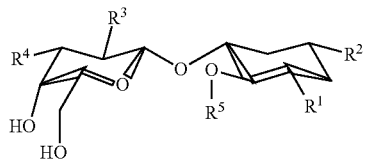

wherein:

R$^1$=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, OH, or NHX where X=H$_1$C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe$_1$ halide, or OH; C(=O)OX, alkanyl substituted with C(=O) OX, C(=O)NHX, alkanyl substituted with C(=O)NHX, where X=C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; O(=O)X, OX, NHX, NH(=O)X, where X=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH;

R$^2$=H$_1$C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, OH, or NHX where X=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; —C(=O)OX where X is C$_1$-C$_8$ alkanyl, C$_1$-C$_8$ alkenyl, C$_1$-C$_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; O(=O)X, OX, NHX$_1$NH(=O)X, where X=H$_1$C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; with the proviso that R$^1$ and R$^2$ are not both H;

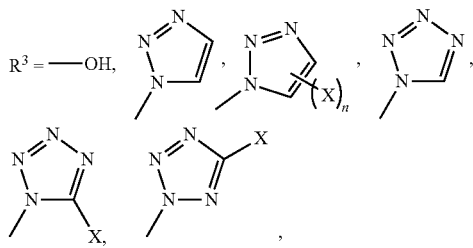

—O—C(=O)—X, —NH$_2$, —NH—C(=O)—NHX, or —NH—C(=O)—X where n=0-2 and X is independently selected from C$_1$-C$_8$ alkanyl, C$_1$-C$_8$ alkenyl, C$_1$-C$_8$ alkynyl,

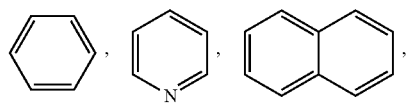

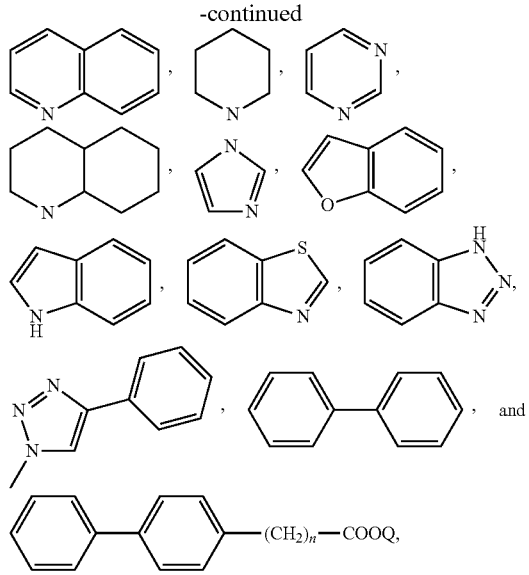

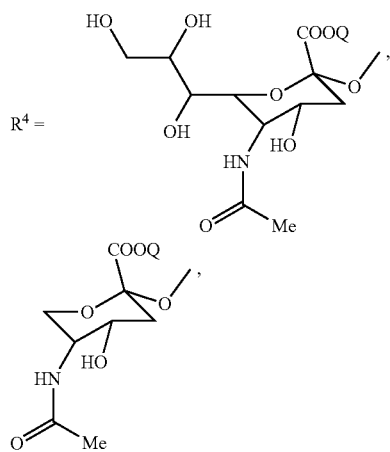

6'sulfated GlcNAc, 6'carboxylated GlcNAc, &sulfated GalNAc, 6'sulfated galactose, 6'carboxylated galactose,

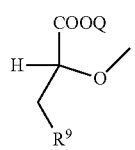

where Q is H or a physiologically acceptable salt or $C_1$-$C_8$ alkanyl, $C_1$-$C_8$ alkenyl, $C_1$-$C_8$ alkynyl, aryl, heteroaryl, $(CH_2)_n$-aryl or $(CH_2)_n$-heteroaryl where n is 1-10, and where $R^9$ is aryl, heteroaryl, cyclohexane, t-butane, adamantane, or triazole, and any of $R^9$ may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl or OY, C(=O) OY, $NY_2$ or C(=O)NHY where Y is H, $C_1$-$C_8$ alkanyl, $C_1$-$C_8$ alkenyl, $C_1$-$C_8$ alkynyl or $C_1$-$C_{14}$ aryl; or

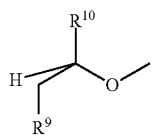

where $R^{10}$ is one of

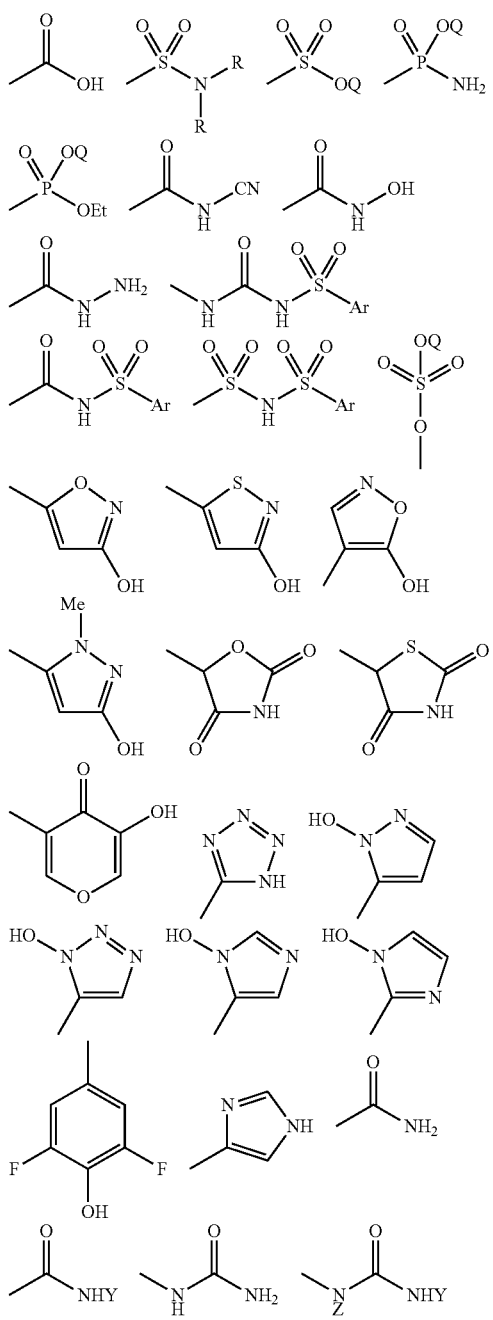

-continued

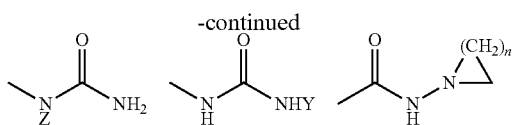

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, n=1-4, Z and Y=$C_1$-$C_8$ alkanyl, $C_rC_8$ alkenyl, $C_rC_8$ alkynyl, halogenated $C_rC_8$ alkanyl, aryl and heteroaryl substituted with Me, OMe, halide, OH; and $R^5$=H, D-mannose, L-galactose, D-arabinose, L-fucose, polyols

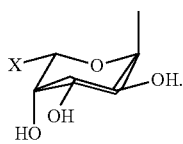

where X=$CF_3$, cyclopropyl or phenyl, or

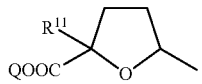

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)$m-aryl or $(CH_2)$m-heteroaryl where m is 1-10, and where $R^{11}$ is aryl, heteroaryl,

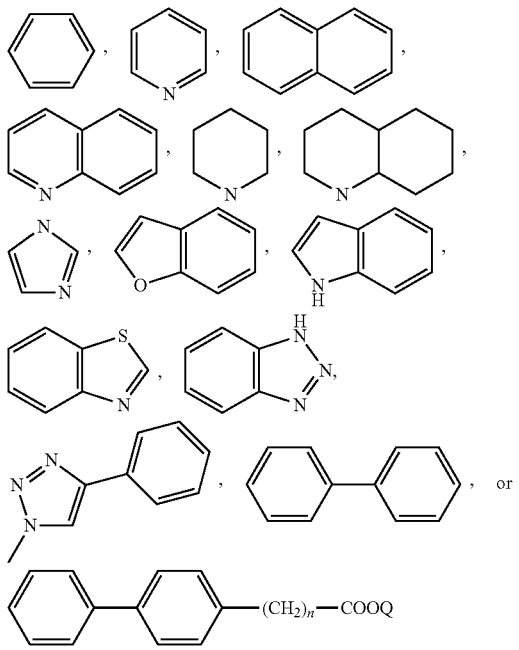

where Q is H or a physiologically acceptable salt, $C_1$-$C_8$ alkanyl, d-$C_8$ alkenyl, d-$C_8$ alkynyl, aryl, heteroaryl, $(CH_2)_m$-aryl or $(CH_2)_m$-heteroaryl where m is 1-10, and where n=0-10, and any one of the above ring compounds may be substituted with one to three independently selected of Cl, F, $C_1$-$C_8$ alkanyl, $C_rC_8$ alkenyl, $C_rC_8$ alkynyl or OY where Y is H, $C_rC_8$ alkanyl, $C_rC_8$ alkenyl or $C_rC_8$ alkynyl.

In some embodiments, the oligosaccharide or glycomimetic compounds are represented by the formula:

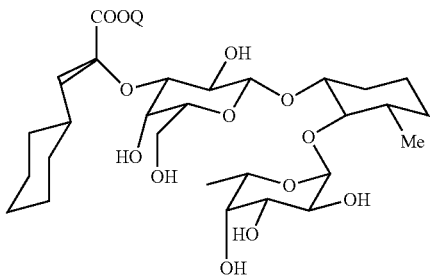

where Q is H or a physiologically acceptable salt, and Me is methyl.

In other embodiments, the oligosaccharide or glycomimetic compounds are represented by the formula:

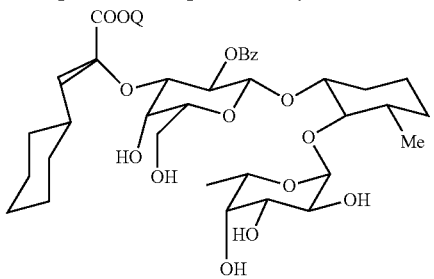

where Q is H or a physiologically acceptable salt, Me is methyl and Bz is benzoyl.

In still other embodiments, the oligosaccharide or glycomimetic compounds are represented by the formula:

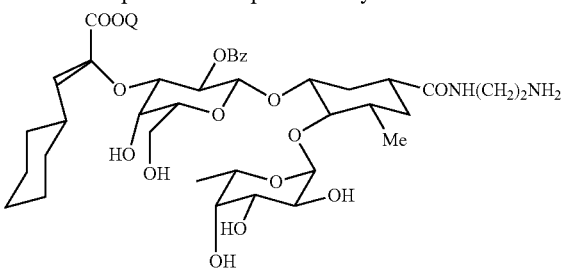

where Q is H or a physiologically acceptable salt, Me is methyl and Bz is benzoyl.

In other embodiments, the oligosaccharide or glycomimetic compounds are represented by the formula:

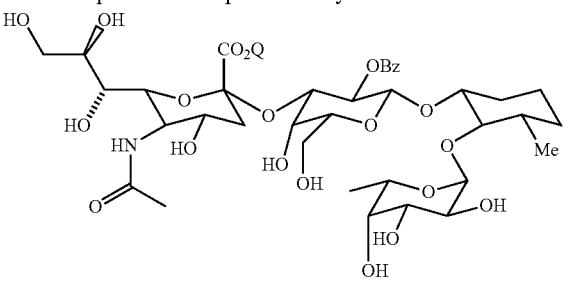

where Q is H or a physiologically acceptable salt, Me is methyl and Bz is benzoyl.

In still other embodiments, the oligosaccharide or glycomimetic compounds are represented by the formula:

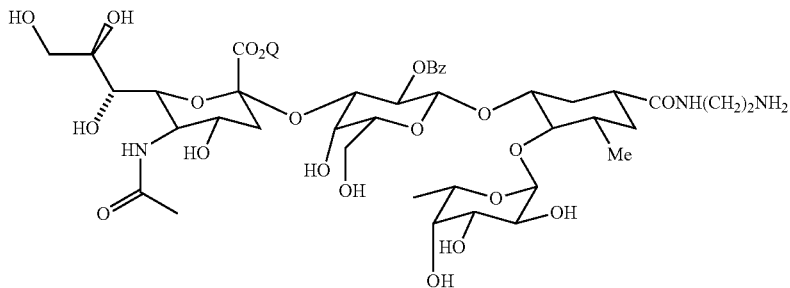

where Q is H or a physiologically acceptable salt and Me is methyl.

In further embodiments, the oligosaccharide or glycomimetic compounds are represented by the formula:

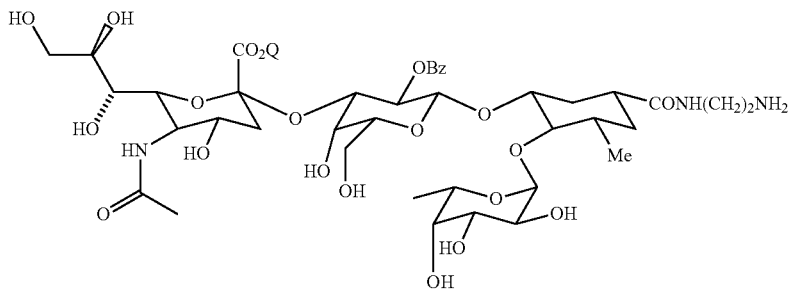

where Q is H or a physiologically acceptable salt, Me is methyl and Bz is benzoyl.

In other embodiments, the oligosaccharide or glycomimetic compounds are represented by the formula:

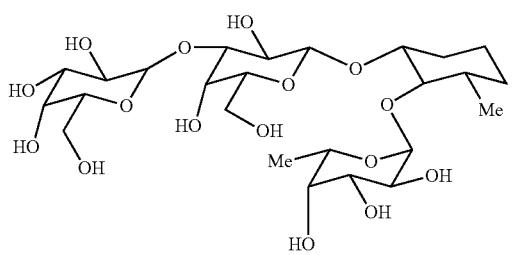

where Me is methyl.

In still other embodiments, the oligosaccharide or glycomimetic compounds are represented by the formula:

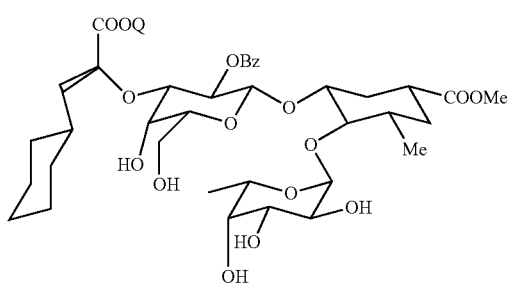

where Q is H or a physiologically acceptable salt, Me is methyl and Bz is benzoyl.

In other embodiments, the oligosaccharide or glycomimetic compounds are represented by the formula:

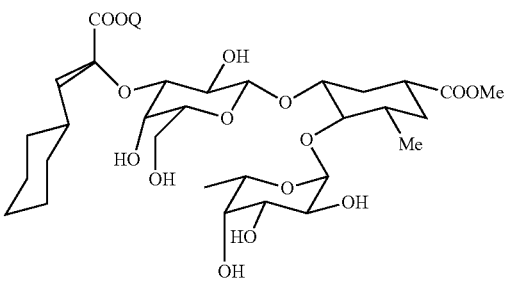

where Q is H or a physiologically acceptable salt, Me is methyl and Bz is benzoyl.

Still other embodiments of the oligosaccharide or glycomimetic compounds are represented by the formula:

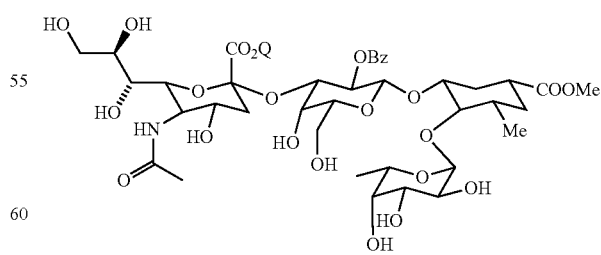

where Q is H or a physiologically acceptable salt, Me is methyl and Bz is benzoyl.

Yet other embodiments of the oligosaccharide or glycomimetic compounds are represented by the formula:

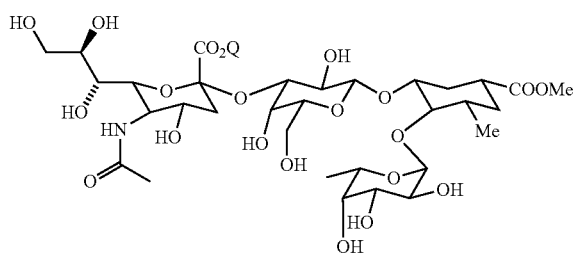

where Q is H or a physiologically acceptable salt and Me is methyl.

Other embodiments of the oligosaccharide or glycomimetic compounds are represented by the formula:

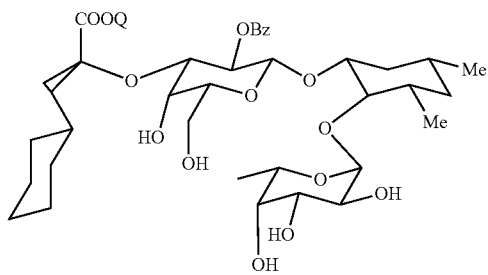

where Q is H or a physiologically acceptable salt, Me is methyl and Bz is benzoyl.

In other embodiments, the oligosaccharide or glycomimetic compounds are represented by the formula:

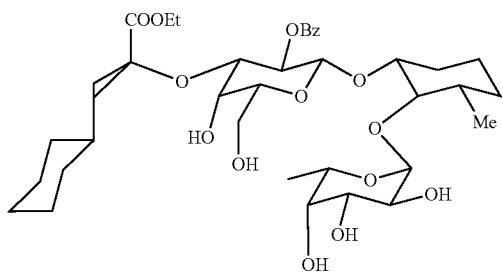

where Me is methyl, Et is ethyl and Bz is benzoyl.

In still other embodiments, the oligosaccharide or glycomimetic compounds are represented by the formula:

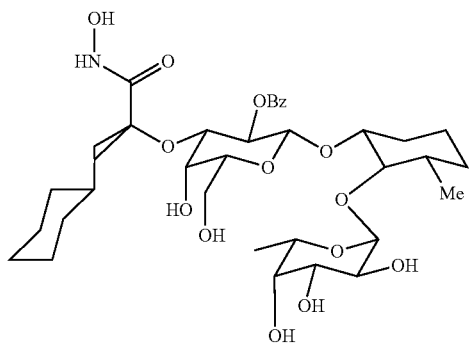

where Me is methyl and Bz is benzoyl.

Other embodiments of the oligosaccharide or glycomimetic compounds are represented by the formula:

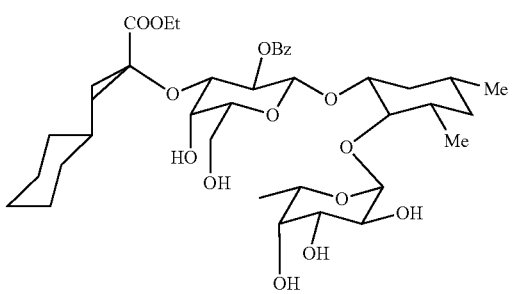

where Me is methyl, Et is ethyl and Bz is benzoyl.

Still other embodiments of the oligosaccharide or glycomimetic compounds are represented by the formula:

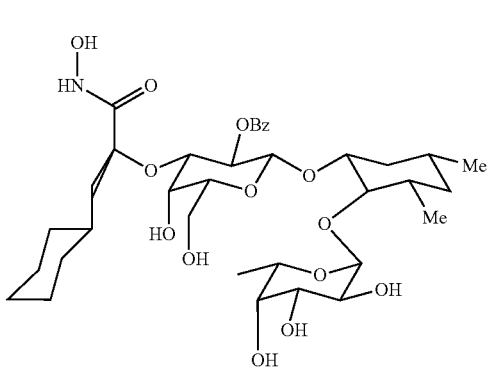

where Me is methyl and Bz is benzoyl.

Alternative carbohydrate inhibitors by Magnani et al. are disclosed in International Publication No. WO 2007/028050, which is expressly incorporated herein by reference in its entirety. These compounds are represented by the formula:

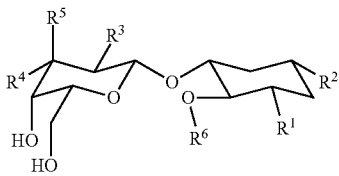

wherein:

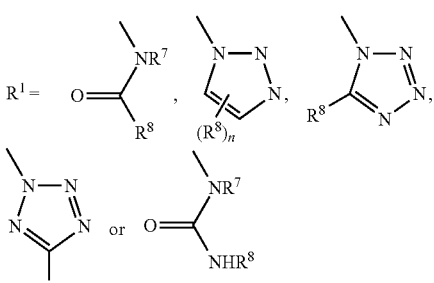

where n=0-2, and $R^8$ are independently selected where n=2;

$R^2$=H, —C(=O)OX where X is $C_1$-$C_8$ alkanyl, $C_1$-$C_8$ alkenyl, $C_1$-$C_8$ alkynyl or $C_1$-$C_{14}$ aryl, —C(=O)NH$(CH_2)_n NH_2$, —[C(=O)NH$(CH_2)_n$NHC(=O)]$_m$(L)$_m$Z, where n=0-30, m=0-1, L is a linker, and Z is a benzyl amino sulfonic acid, a benzyl amino carboxylic acid, a polyethylene glycol, or a second compound or salt thereof having the above formula to form a dimer where $R^2$ of the second compound or salt thereof has m=0, no Z, and is the point of attachment;

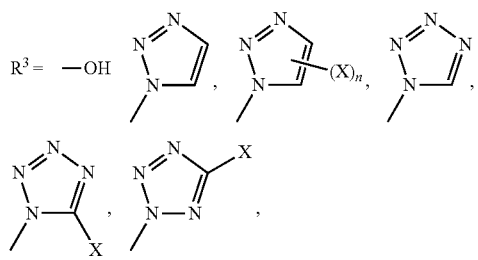

—O—C(=O)—X, —$NH_2$, —NH—C(=O)—NHX, or —NH—C(=O)—X where n=0-2 and X is independently selected from $C_1$-$C_8$ alkanyl, $C_1$-$C_8$ alkenyl; $C_1$-$C_8$ alkynyl,

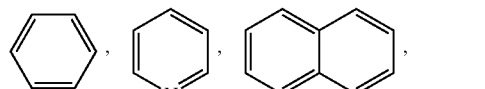

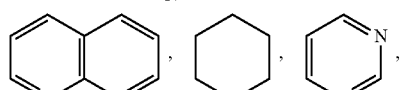

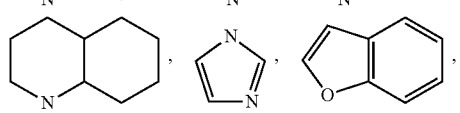

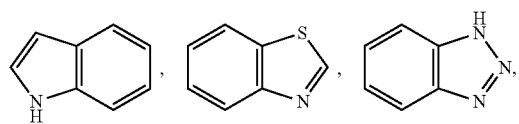

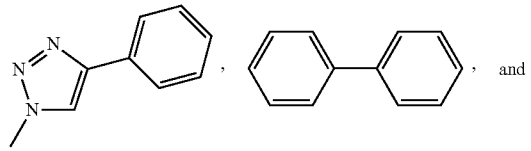

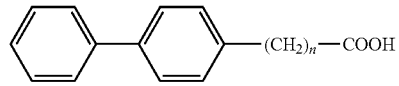

where n = 0-10, and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl, or OY where Y is H, $C_1$-$C_8$ alkanyl, $C_1$-$C_8$ alkenyl, $C_1$-$C_8$ alkynyl, or $C_1$-$C_{14}$ aryl;

$R^4$ = 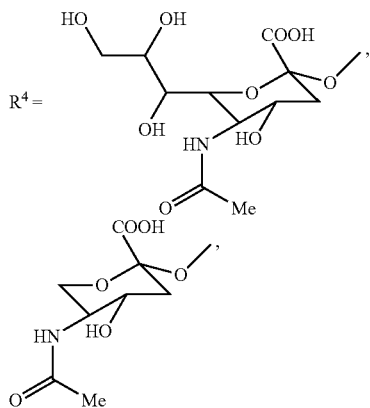

6'sulfated GlcNAc, 6'carboxylated GlcNAc, 6'sulfated GalNAc, 6'sulfated galactose, 6'carboxylated galactose or

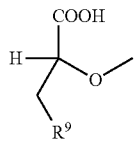

where $R^9$ is aryl, heteroaryl, cyclohexane, t-butane, adamantane, or triazole, and any of $R^9$ may be substituted with one to three independently selected of Cl, F, $C_1$-$C_8$ alkanyl, $CrC_8$ alkenyl, $C_1$-$C_8$ alkynyl or OY where Y is H, $C_1$-$C_8$ alkanyl, $CrC_8$ alkenyl, $CrC_8$ alkynyl or $C_1$-$C_{14}$ aryl;

$R^5$=H, or $R^4$ and R are taken together to form

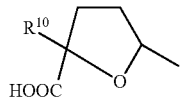

where $R^{10}$ heteroaryl,

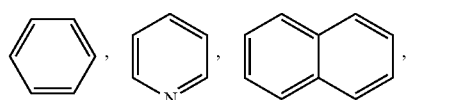

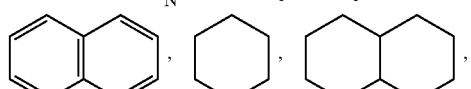

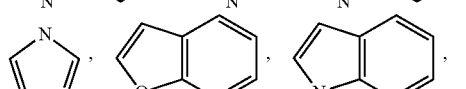

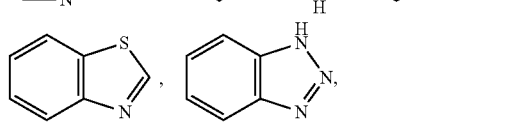

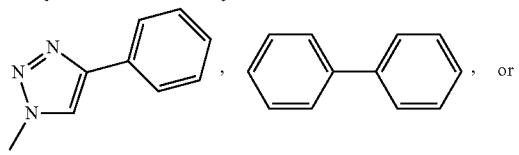

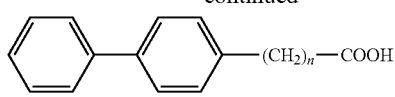

where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl;

$R^6$=H, fucose, mannose, arabinose, galactose or polyols;

$R^7$=H, $C_1$-$C_8$ alkanyl, $C_1$-$C_8$ alkenyl, $C_1$-$C_8$ alkynyl or

$R^8$=H, $C_1$-$C_8$ alkanyl, $C_1$-$C_8$ alkenyl, $C_1$-$C_8$ alkynyl,

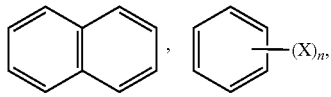

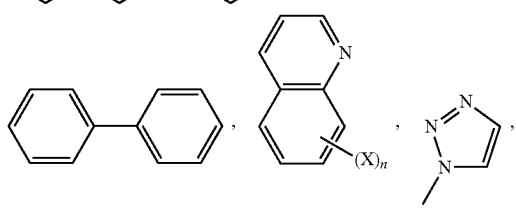

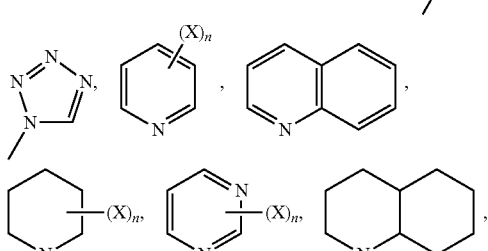

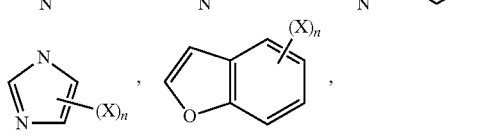

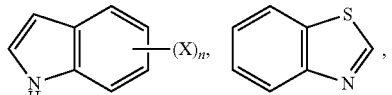

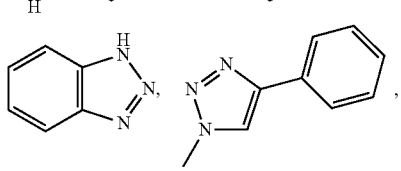

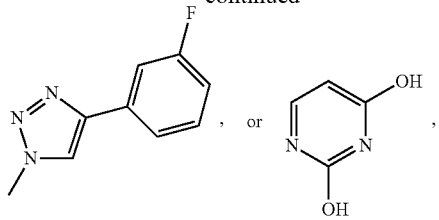

where n=0-3 and X is independently selected from H, OH, Cl, F, $N_3$, $NH_2$, $C_1$-$C_8$ alkanyl, $C_1$-$C_8$ alkenyl, $C_1$-$C_8$ alkynyl, $C_1$-$C_{14}$ aryl, $OC_1$-$C_8$ alkanyl, $OC_1$-$C_8$ alkenyl, $OC_1$-$C_8$ alkynyl, and $OC_1$-$C_{14}$ aryl, and any of the above ring compounds may be substituted with one to three independently selected of Cl, F, $C_1$-$C_8$ alkanyl, $C_1$-$C_8$ alkenyl, $C_1$-$C_8$ alkynyl, $C_1$-$C_{14}$ aryl or OY where Y is H, $C_1$-$C_8$ alkanyl, $C_1$-$C_8$ alkenyl, $C_1$-$C_8$ alkynyl, or $C_1$-$C_{14}$ aryl.

Alternate carbohydrate inhibitors by Magnani et al. are disclosed in US Appl. Pub. No. 2006/0194745, which is expressly incorporated herein by reference in its entirety. These compounds have the formula:

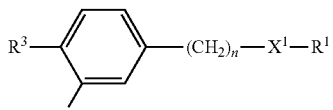

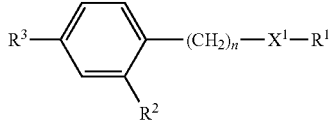

where n is 0 or 1; $X^1$ is —$PO_2M$, —$SO_2M$ or —$CF_2$— wherein M is a pharmaceutically acceptable counterion; $R^1$ is —OH, —F or —$CO_2R^4$ where $R^4$ is —H or —$(CH_2)_m$—$CH_3$ and m is 0 to 3; $R^2$ is —H, —$PO_3M_2$, —$SO_3M_2$, —$CH_2$—$PO_3M_2$, —$CH_2$—$SO_3M_2$, —$CF_3$, —$(CH_2)_m$—$C(R^6)H$—$R^5$ or $R^9$—$N(R^{19})$— wherein M is defined as above; $R^3$ is —H, —$(CH_2)_m$—$C(R^6)H$—$R^5$ or $R^9$—$N(R^{10})$— where $R^5$ and $R^6$ are independently selected from —H, —$CO_2$—$R^7$ and —NH—$R^8$; $R^7$ and $R^8$ are independently selected from hydrogen, an alkyl group, an aromatic group, an amino group and a carboxy group, and $R^9$ and $R^{10}$ are independently selected from —H, —$(CH_2)_m$—$CH_3$; —$CH_2$—Ar, and —CO—Ar, where m is 0 to 3 and Ar is an aromatic group; or

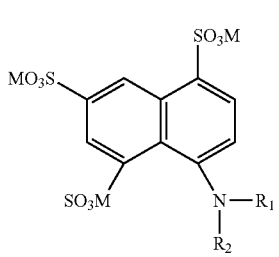

where $R_1$ and $R_2$ are independently selected from hydrogen, an alkyl group, an aromatic group, an amino group or a carboxy group, and —CO—$R_3$ where $R_3$ is as defined above; and M is a pharmaceutically acceptable counterion.

Other carbohydrate inhibitors by Magnani et al. are disclosed in International Publication No. WO 2006/127906, which is expressly incorporated herein by reference in its entirety. These compounds have the formula:

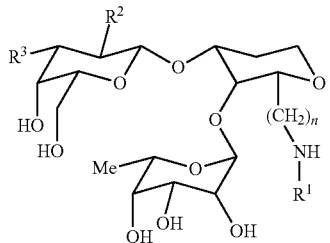

wherein: n=0-20
$R^1$=

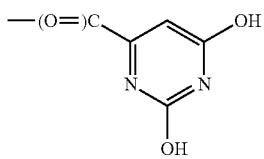

a benzyl amino sulfonic acid, a benzyl amino carboxylic acid, or a second compound or salt thereof having the above formula to form a dimer;

$R^2$=,

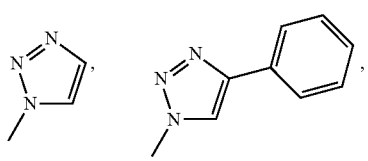

—O—C(=O)—X or —NH—C(=O)—X
where X is

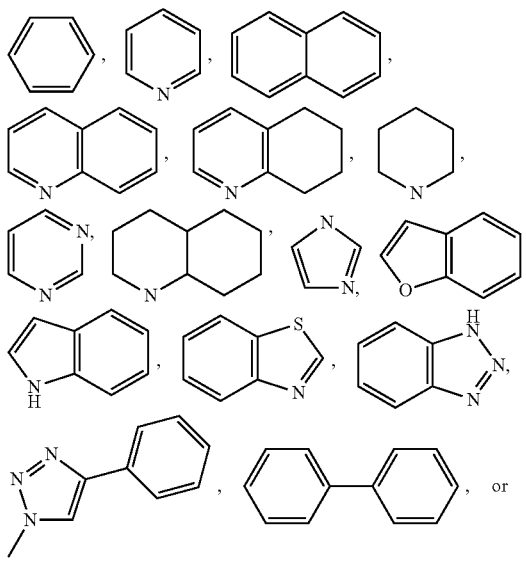

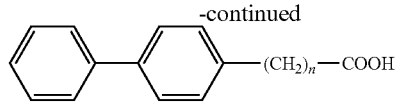

where n=0-10, and any of the above ring compounds may be substituted with one to three of Cl, F, $C_1$-$C_8$ alkanyl or OY where Y is H or $C_1$-$C_8$ alkanyl;
$R^3$=OH,

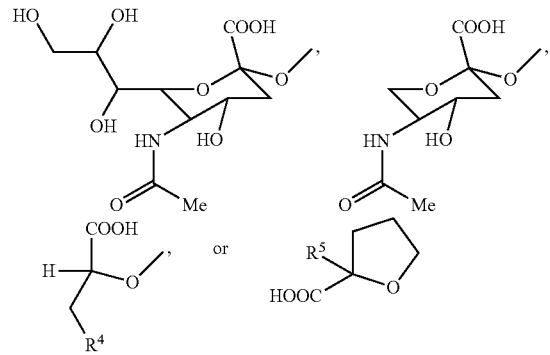

where $R^4$ is cyclohexane, t-butane, adamantane, benzene, triazole, or triazole substituted with one to three of Cl, $F_1C_1$-$C_8$ alkanyl or OY where Y is H or $C_1$-$C_8$ alkanyl, and where $R^5$ is

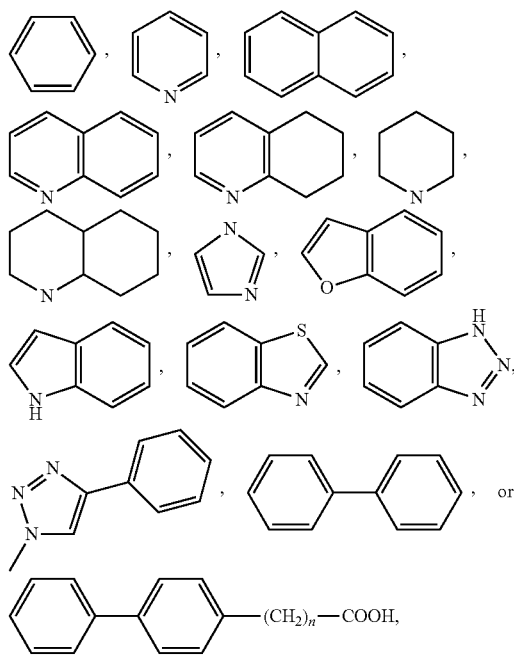

where n=0-10, and any one of the above ring compounds may be substituted with one to three of Cl, F, $C_1$-$C_8$ alkanyl or OY where Y is H or $C_1$-$C_8$ alkanyl; and with the proviso that where $R^1$ is a benzyl amino sulfonic acid and $R^2$ or X of $R^2$ is aromatic, then $R^4$ of $R^3$ is not cyclohexane.

Alternative carbohydrate inhibitors by Magnani et al. are disclosed in International Publication No. WO 2005/054264, which is expressly incorporated herein by reference in its entirety. These compounds are represented by the formula:
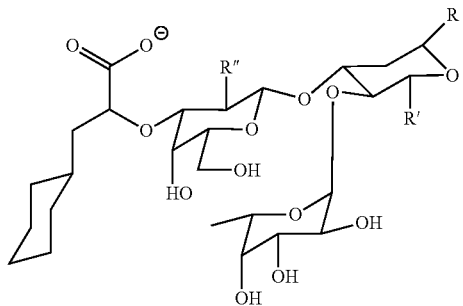
wherein:
R=H or a benzyl amino sulfonic acid;
R'=a benzyl amino sulfonic acid,
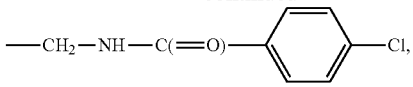
—CH$_2$—NH—C(=O)—NH—CH$_2$—CH$_3$, —CH$_2$—OH, —OH,
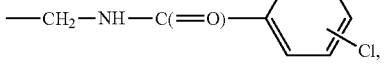
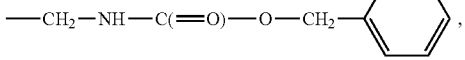
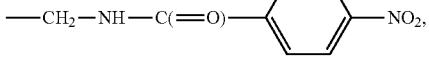
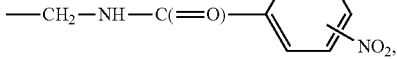
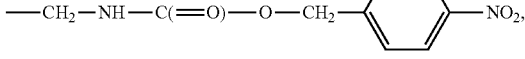
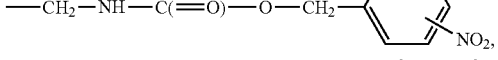
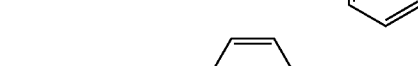
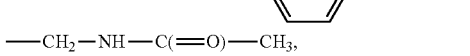
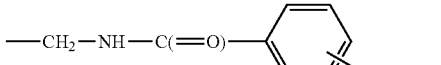
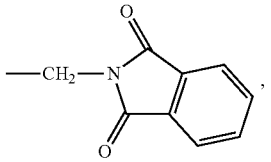
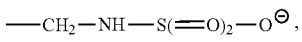
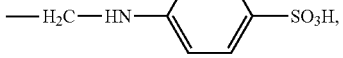
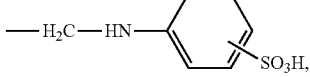
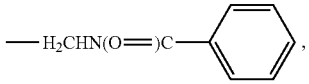

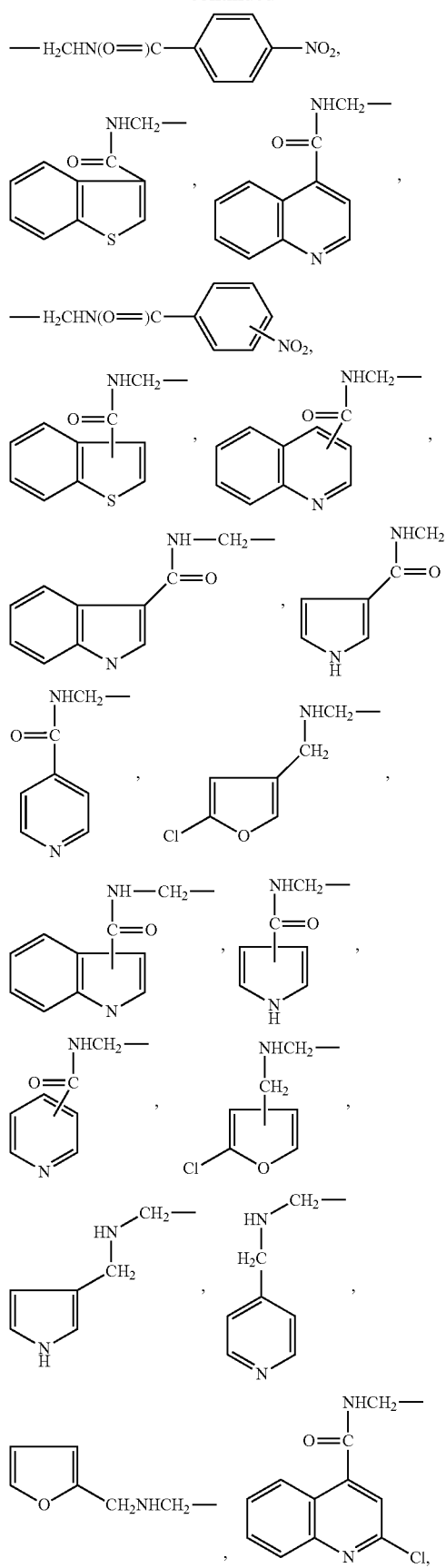
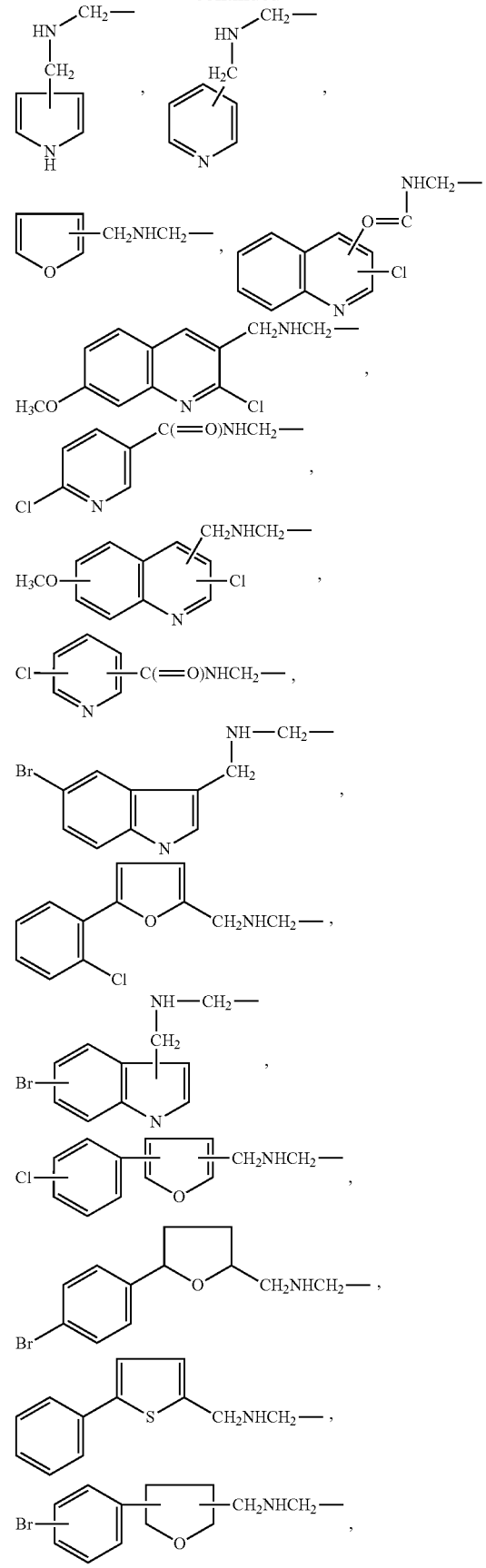

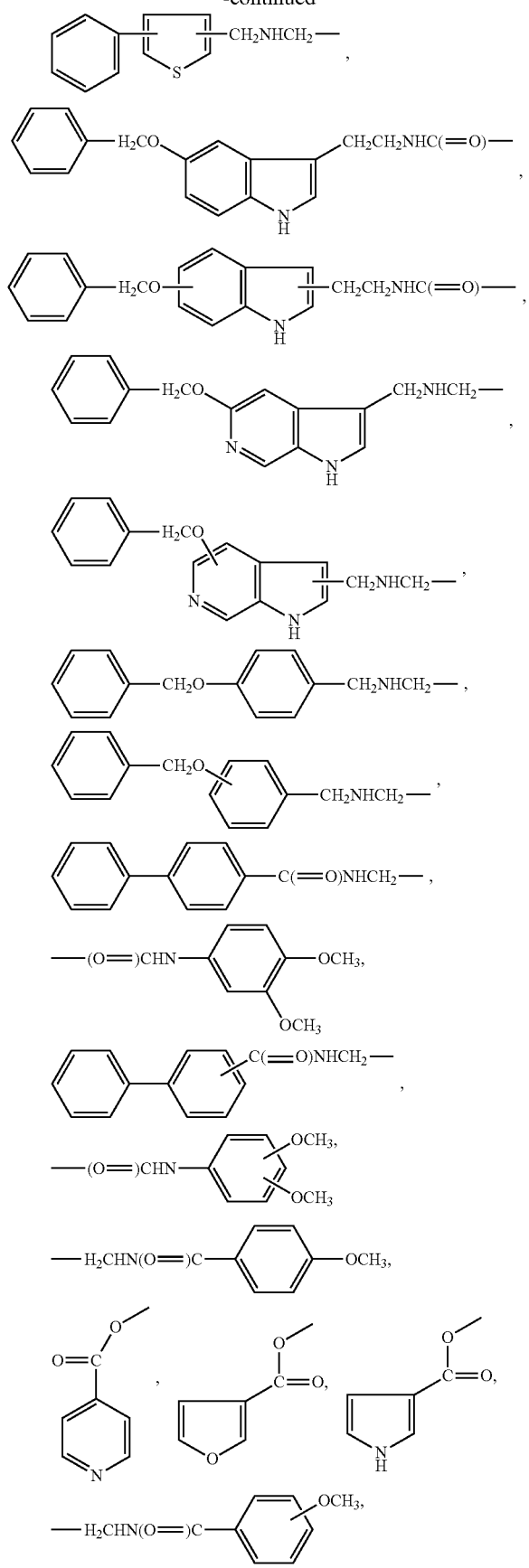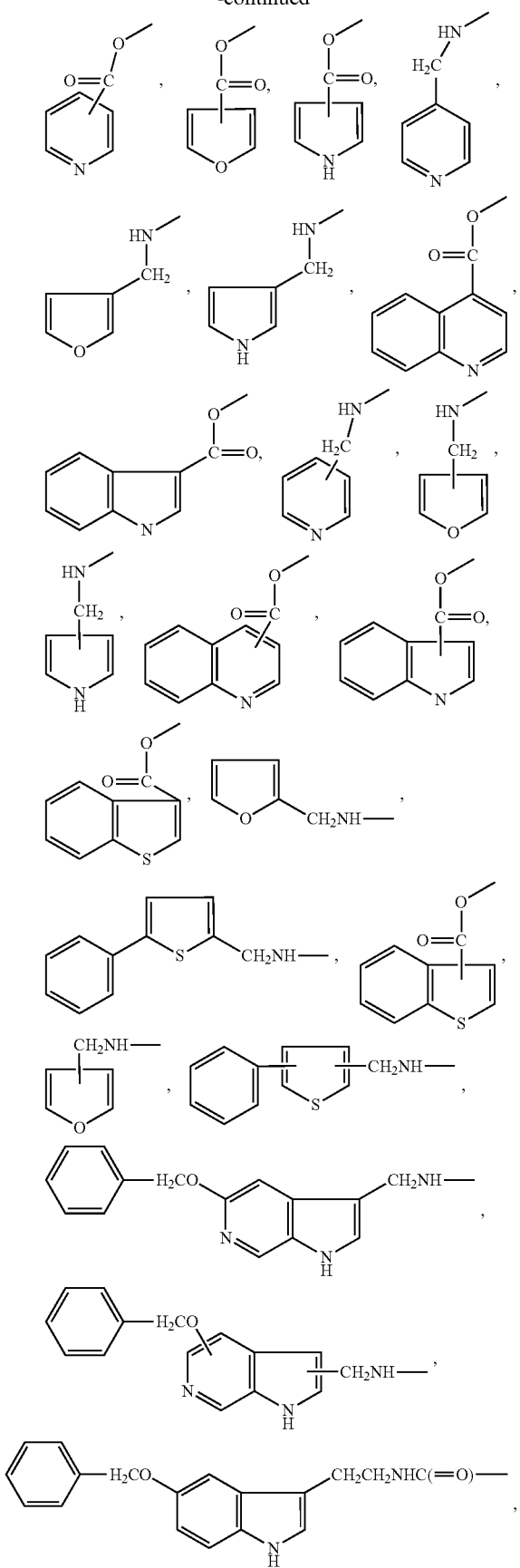

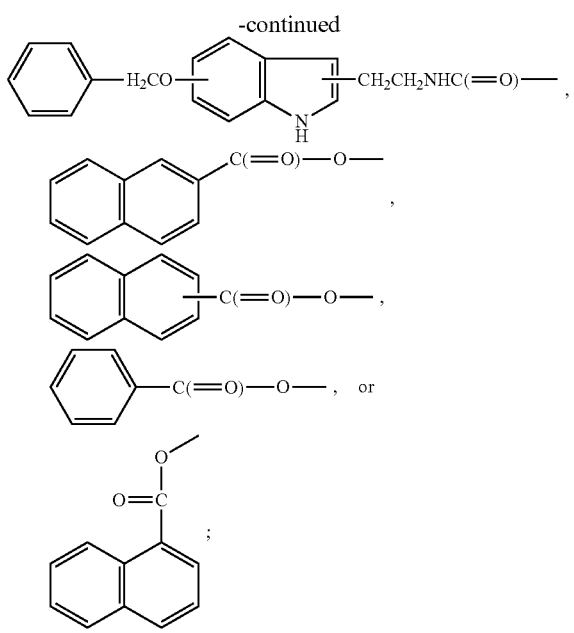
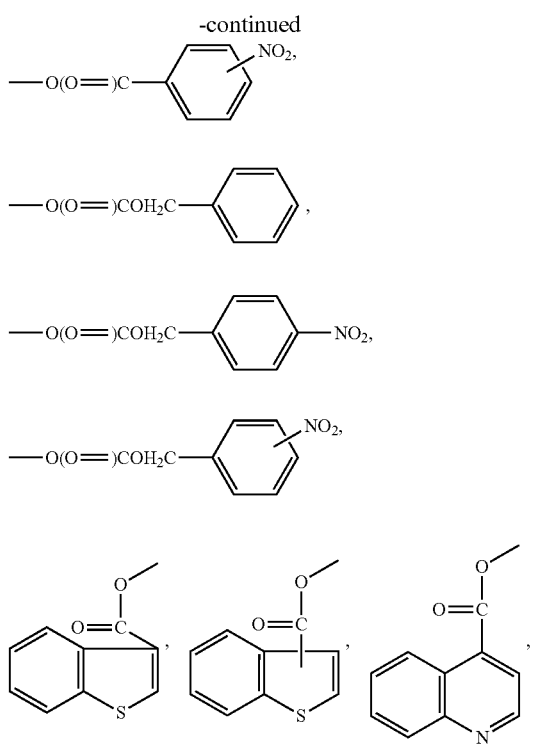
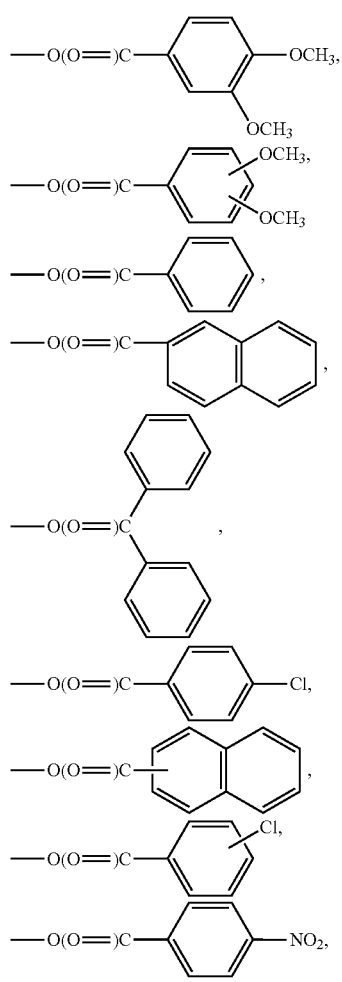

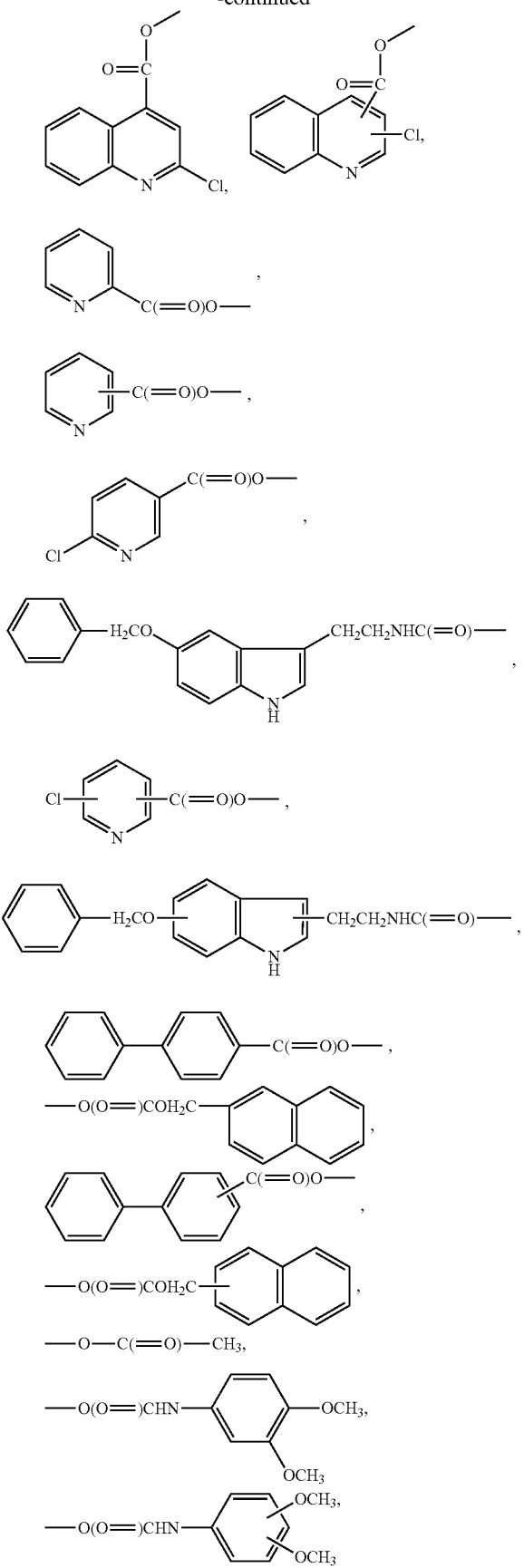
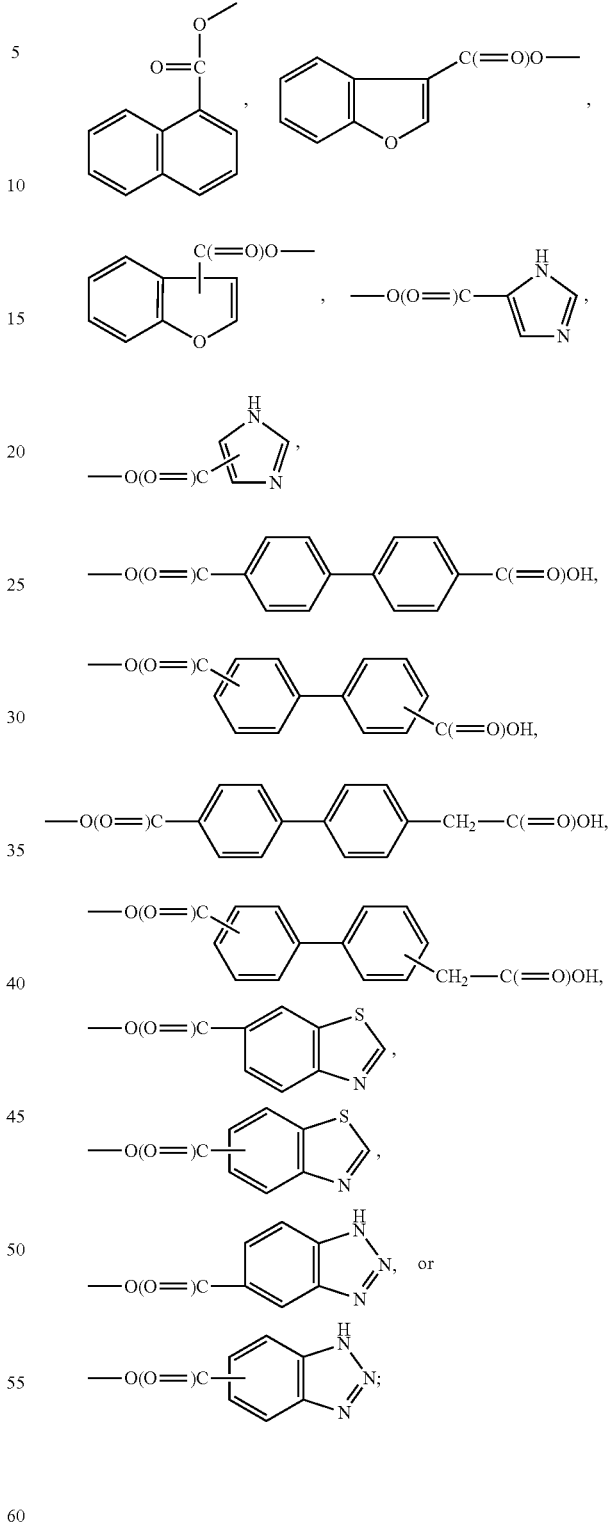
wherein the compound possesses a benzyl amino sulfonic acid at R, R' or R" but not at more than one of R, R' and R".
Still other carbohydrate inhibitors by Magnani et al. are disclosed in International Publication No. WO 2005/051920, which is expressly incorporated herein by reference in its entirety. These compounds are represented by the formula:

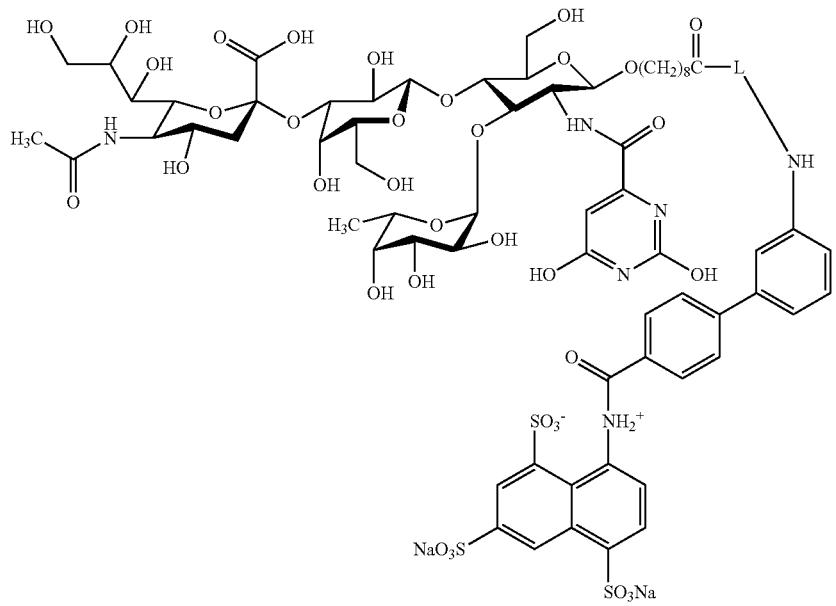

where L is a linker, which is suitably selected from:

In other illustrative examples, the carbohydrate inhibitor is selected from the selective E-selectin antagonist compounds disclosed by Magnani et al. in International Publication No. WO 2004/004636, which is expressly incorporated herein by reference in its entirety. Non-limiting examples of these compounds are selected from:

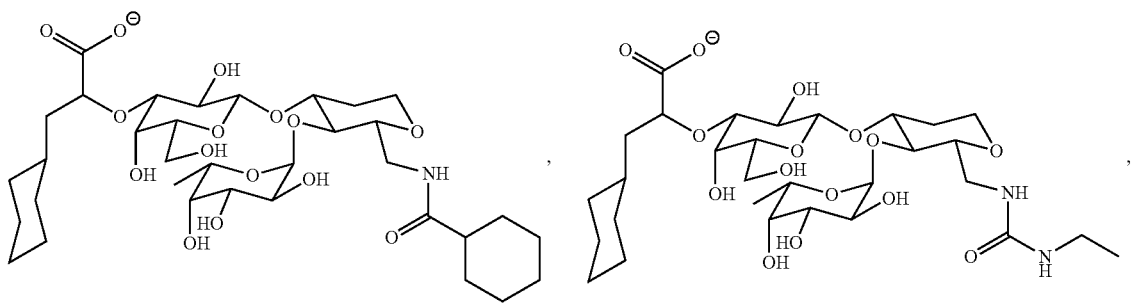

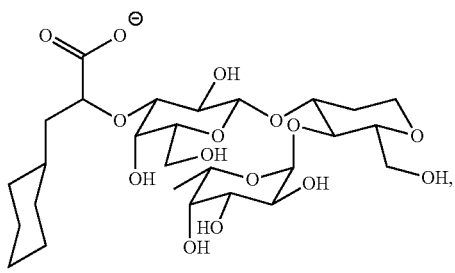
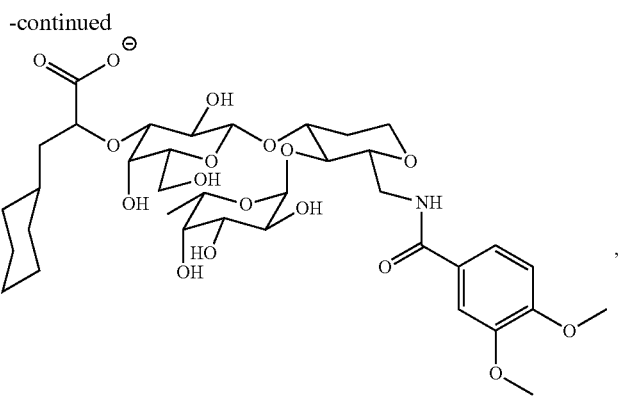
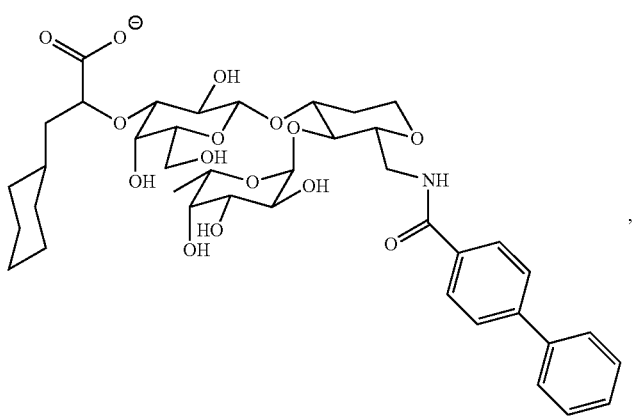
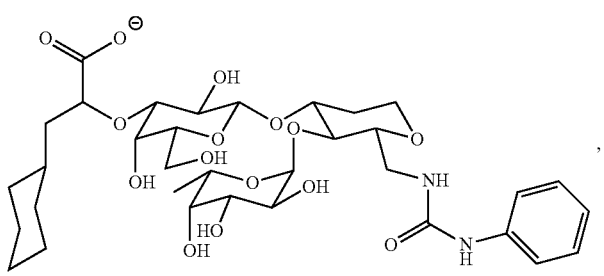
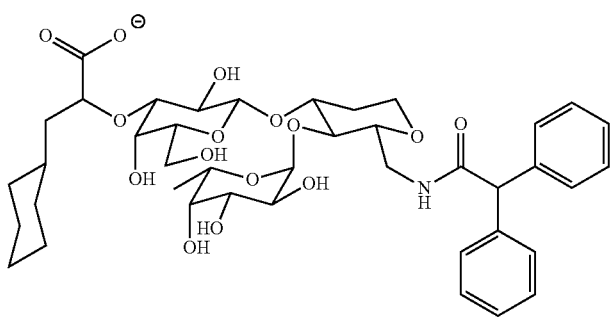

-continued
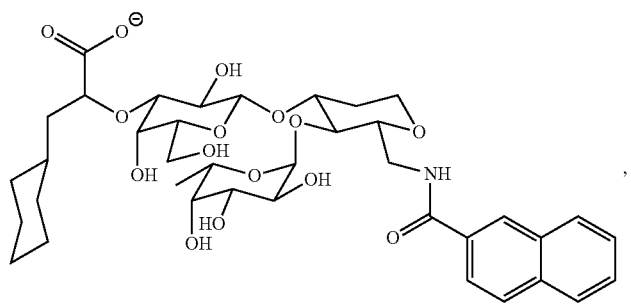
,
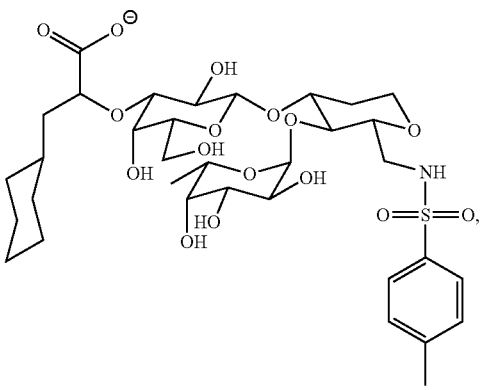
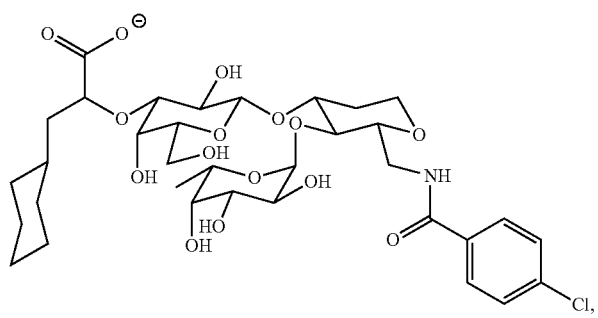
,
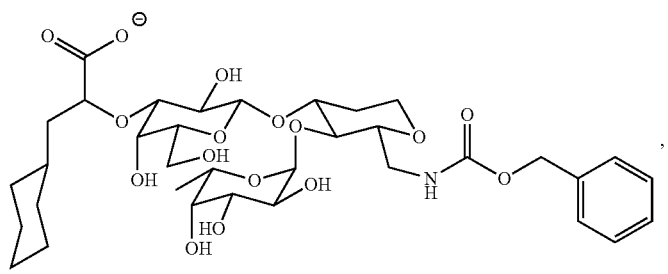
,
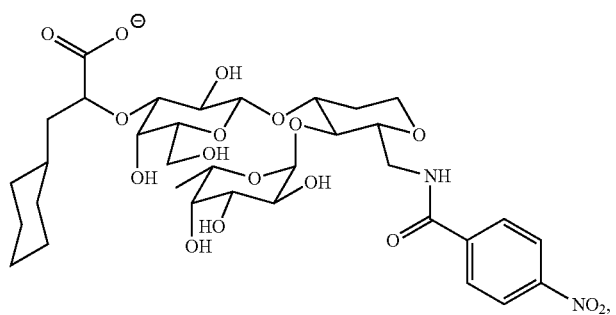
,
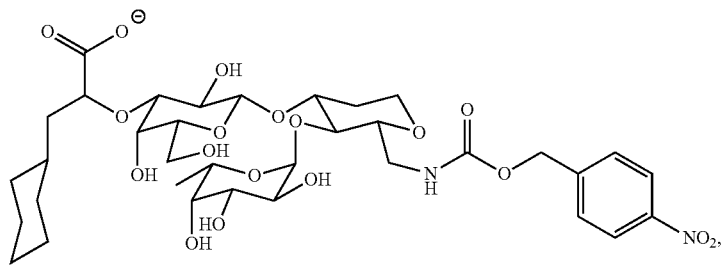
, -continued
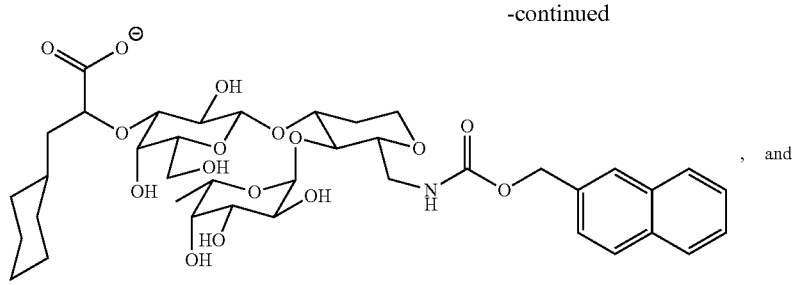, and
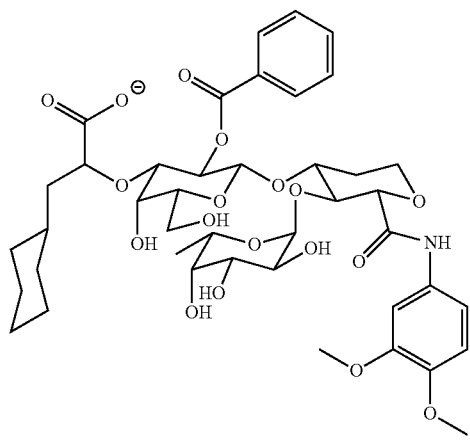
Further carbohydrate inhibitors by Magnani et al. are disclosed in International Publication No. WO 2003/097658, which is expressly incorporated herein by reference in its entirety. These compounds are represented by a formula selected from the group consisting of:
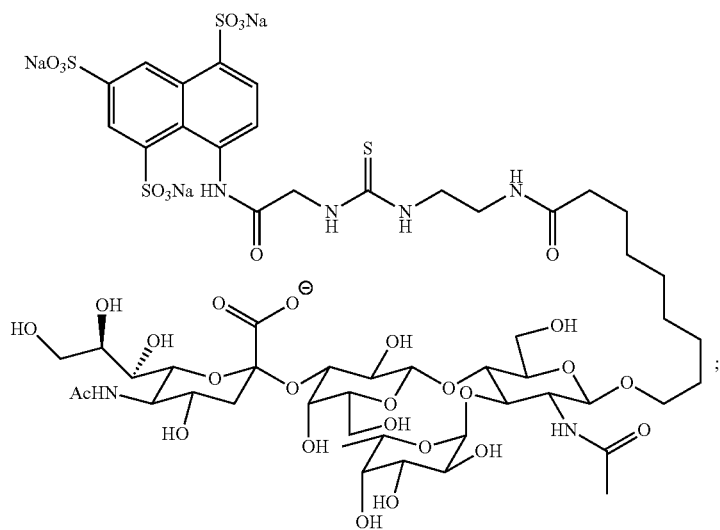

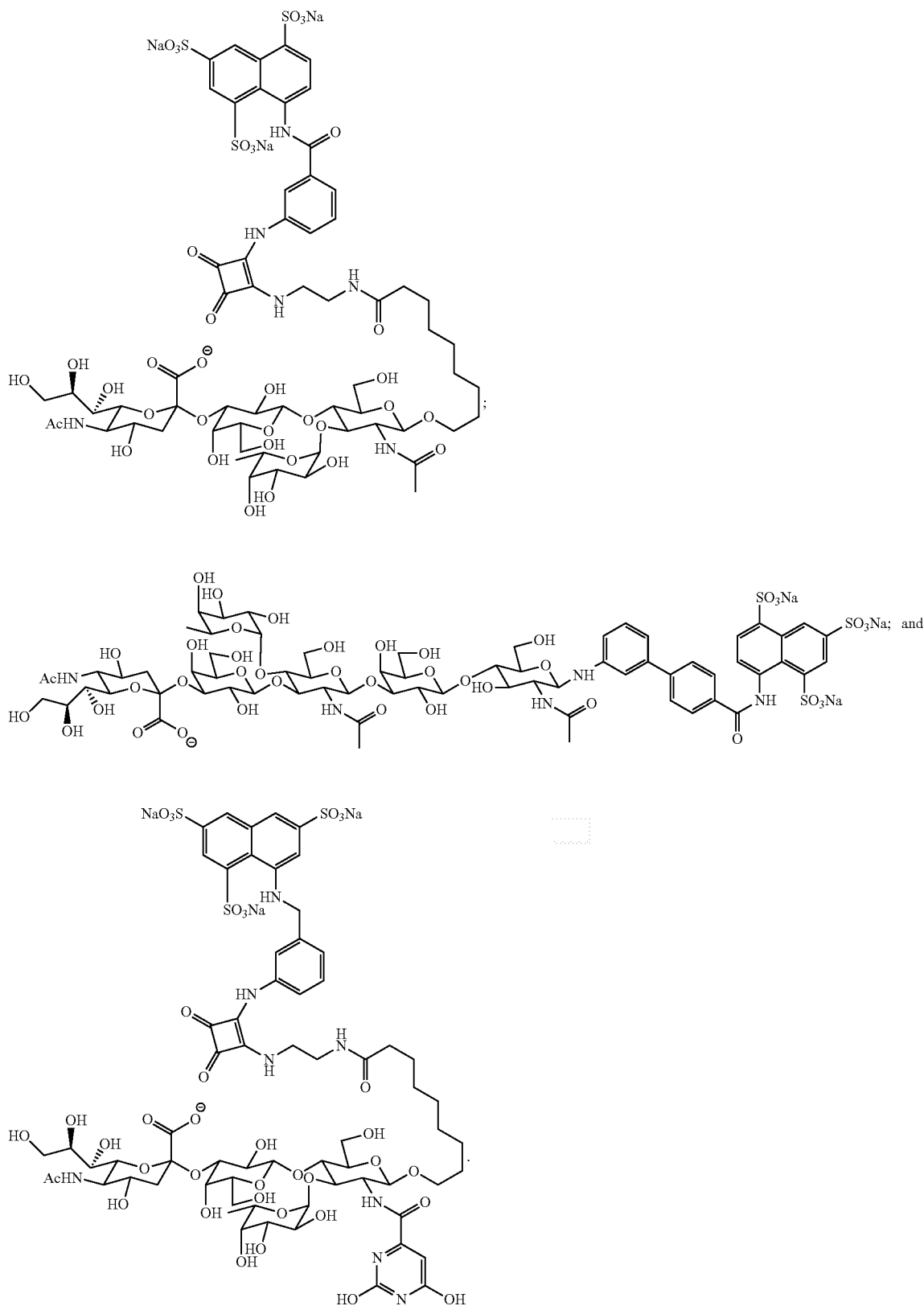
Still other carbohydrate inhibitors by Magnani et al. are disclosed in U.S. Pat. No. 7,361,644, which is expressly incorporated herein by reference in their entirety. These compounds are selected from the following formulas:

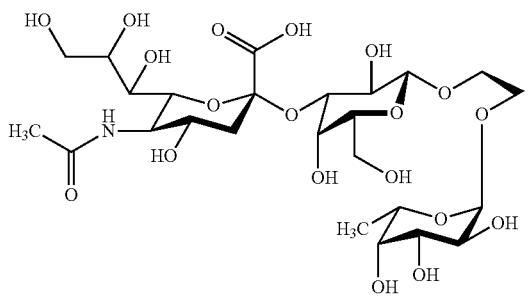

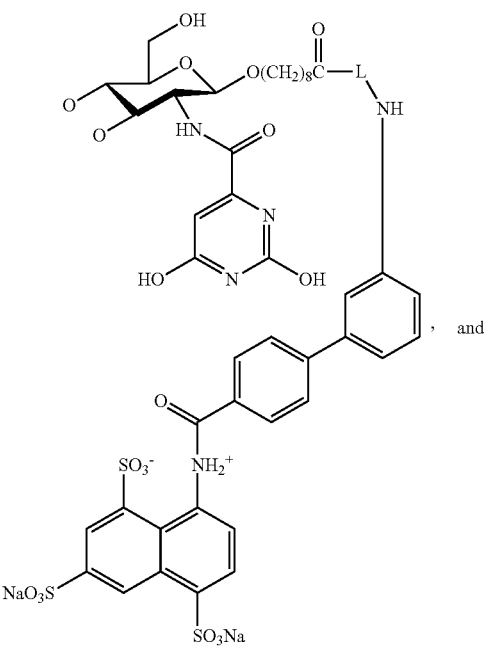

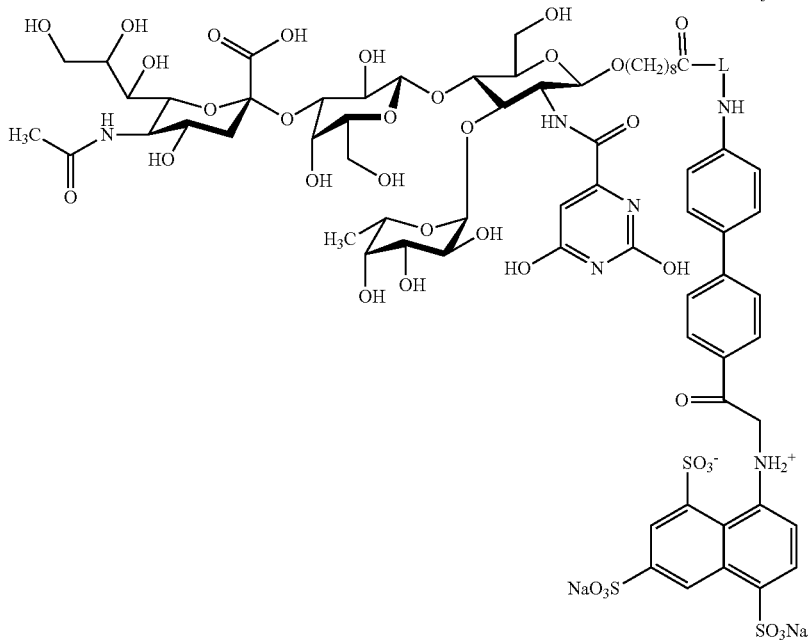

wherein L is a linker.

Representative linkers according to these examples are selected from:

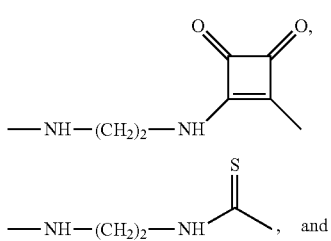

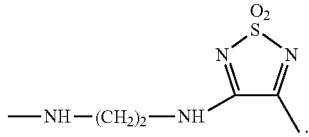

Other carbohydrate inhibitors by Magnani et al. are disclosed in U.S. Pat. No. 7,060,685, which is expressly incorporated herein by reference in their entirety. These compounds consist of a benzyl amino sulfonic acid (BASA) linked to a carbohydrate or a glycomimetic, wherein the carbohydrate or the glycomimetic binds a selectin; wherein the BASA is

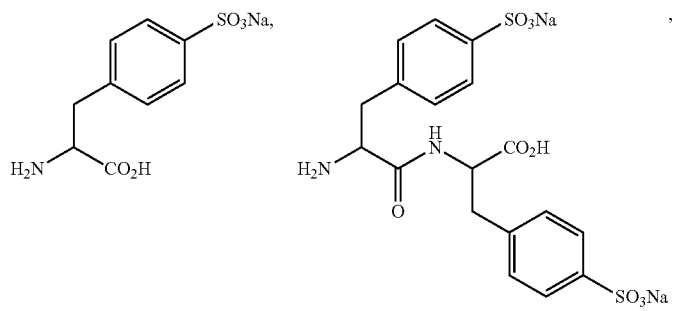
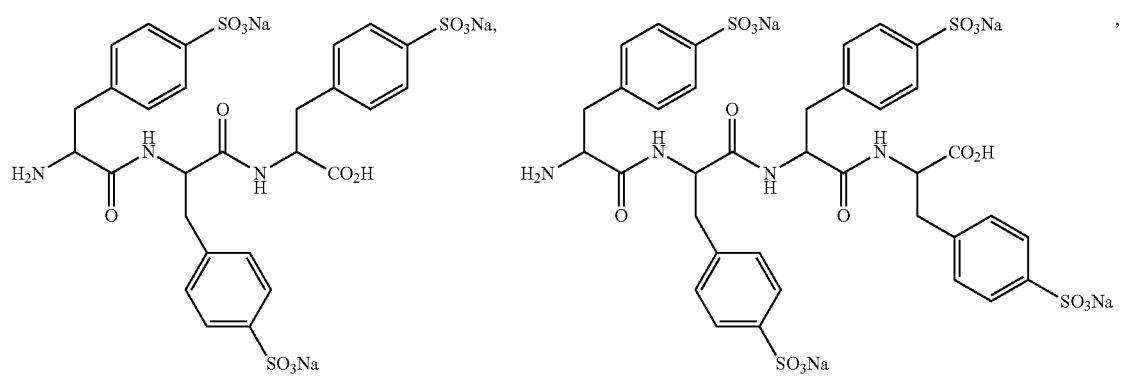
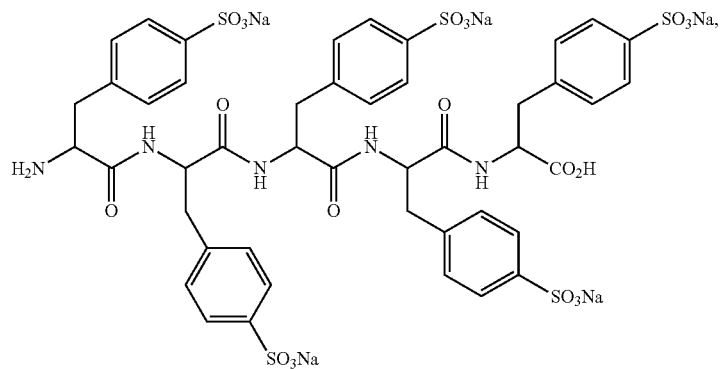
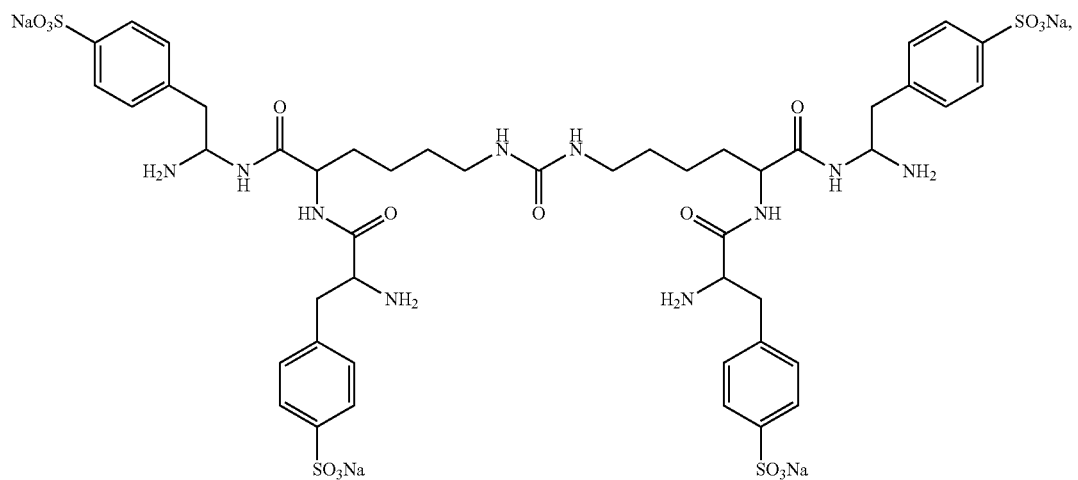

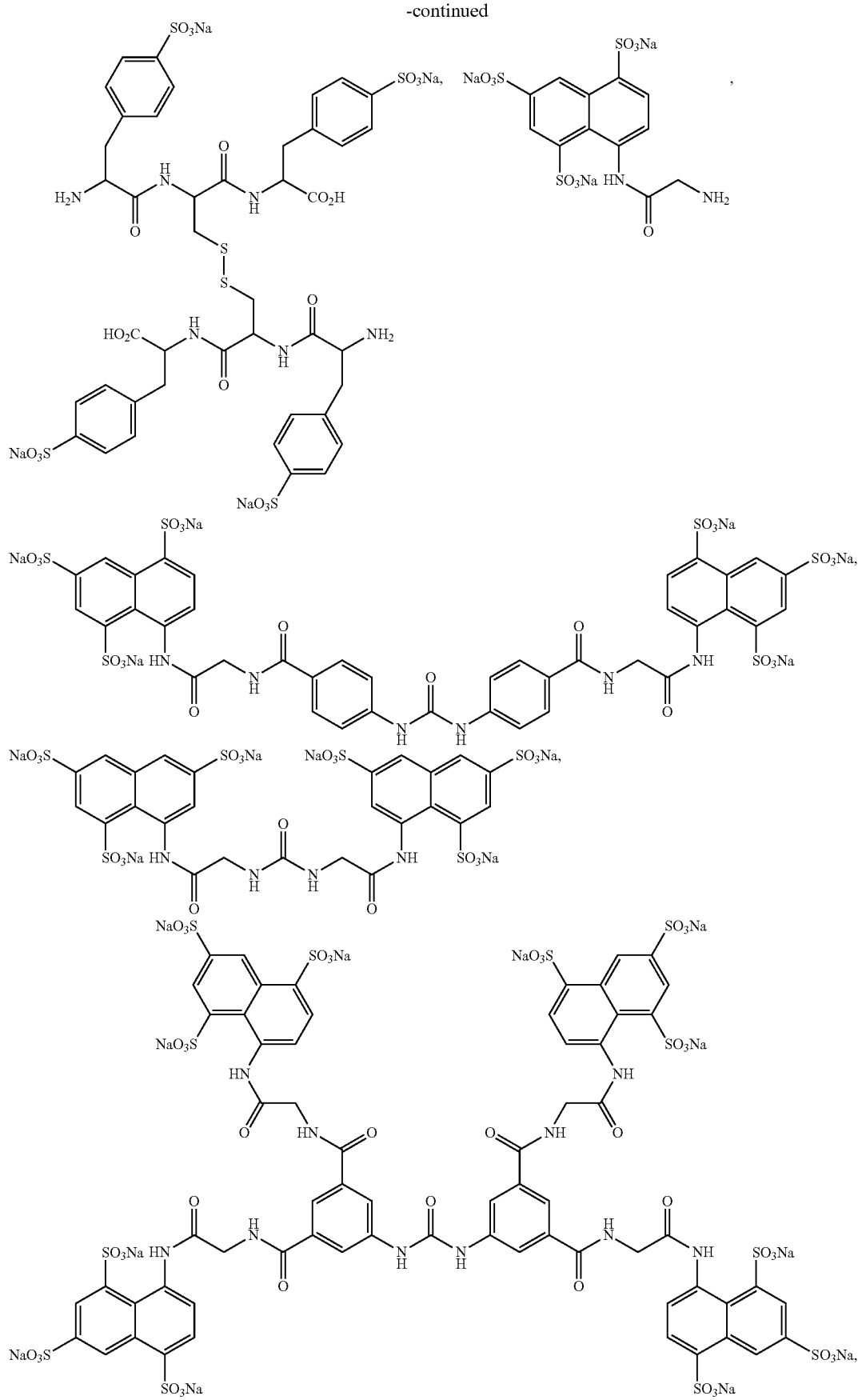

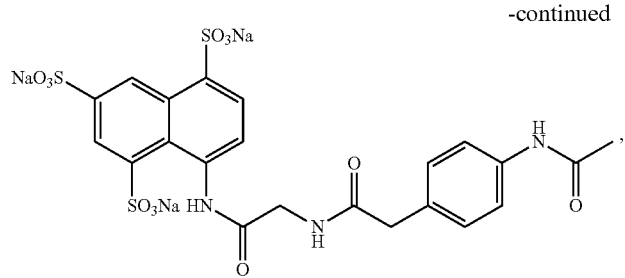
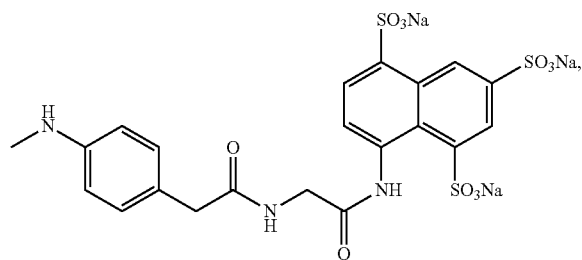
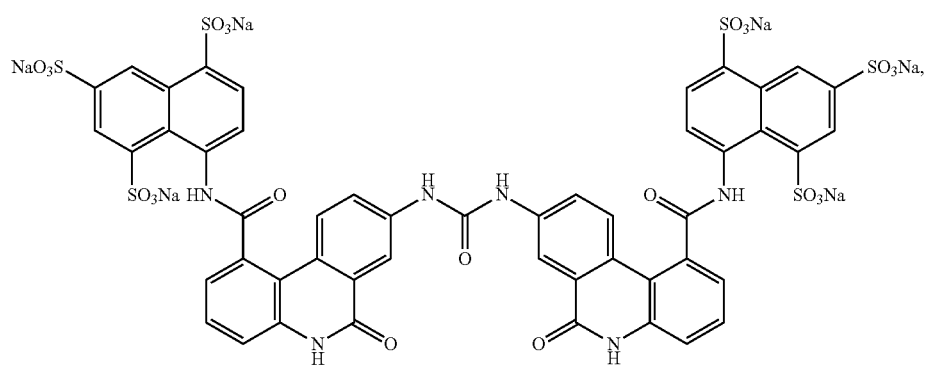
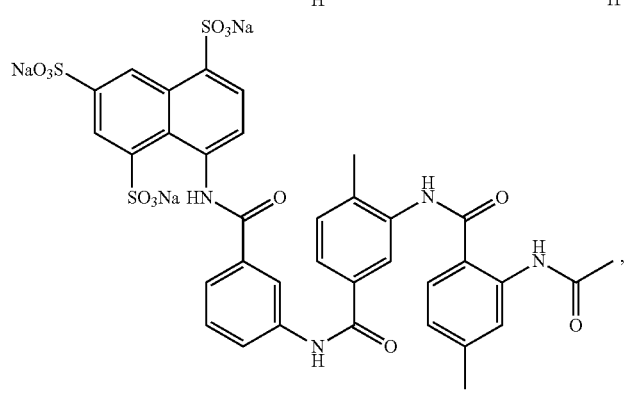
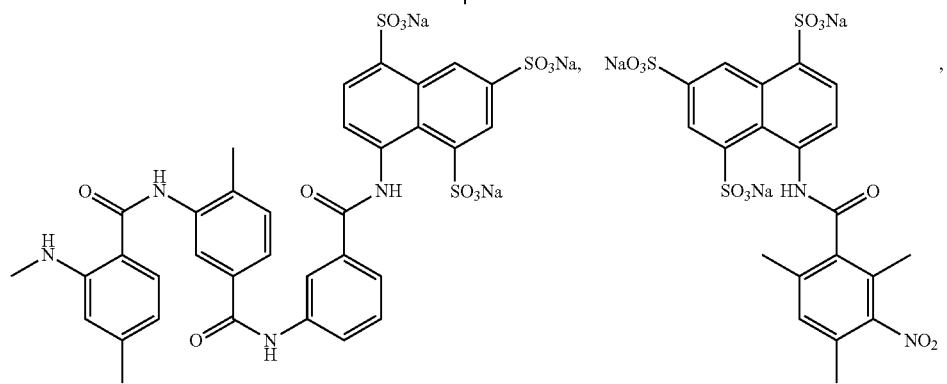
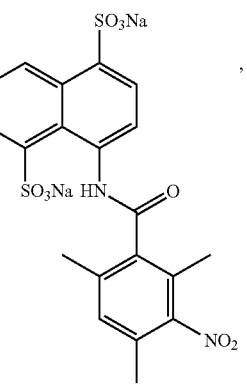

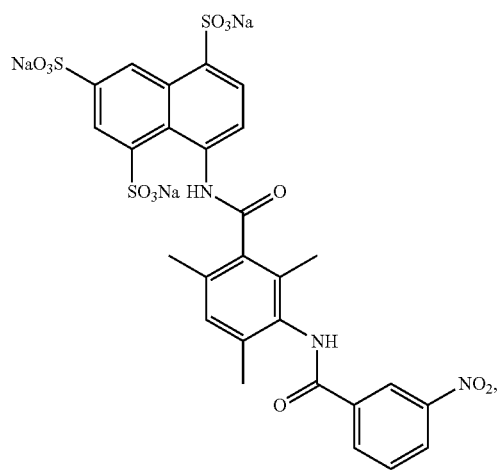
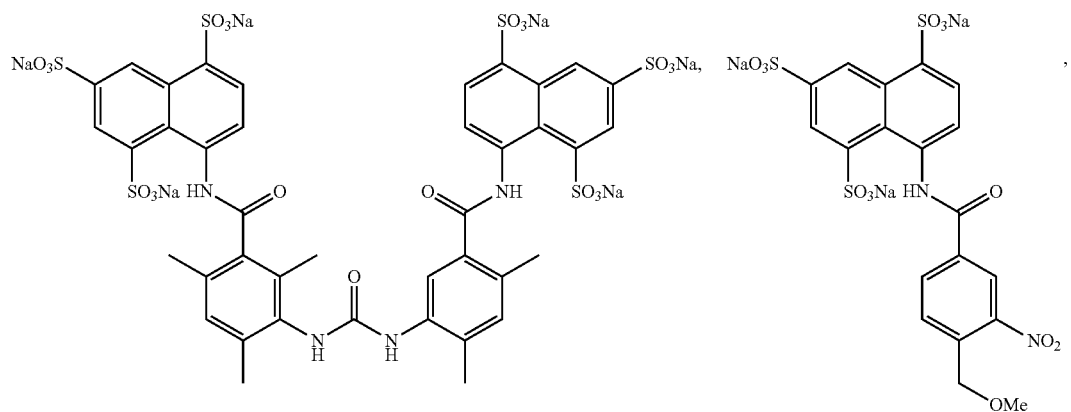
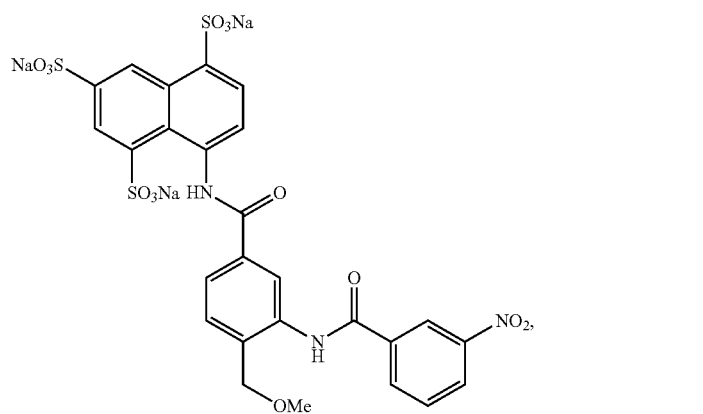
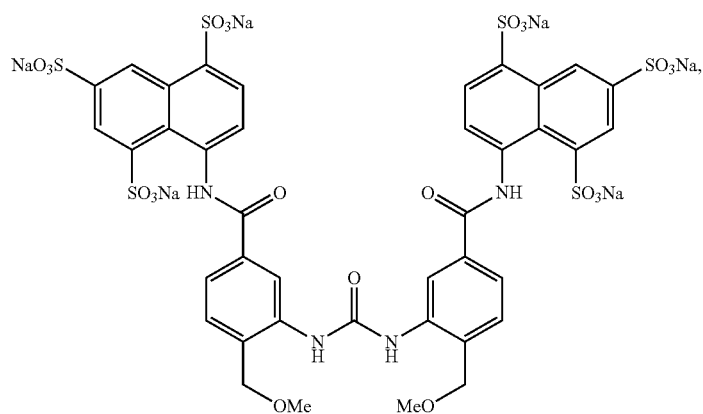

85
86
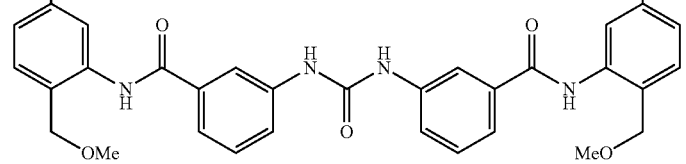
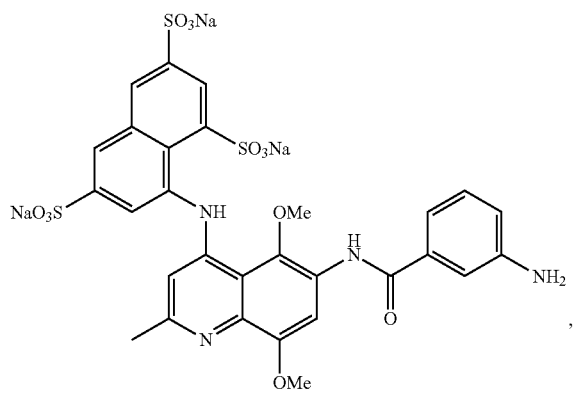
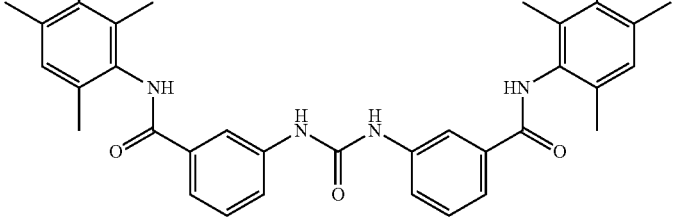

-continued
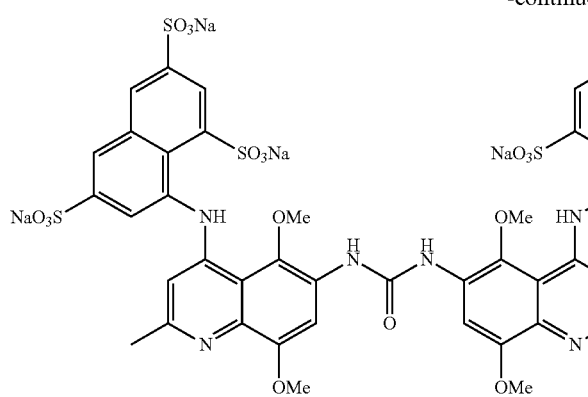
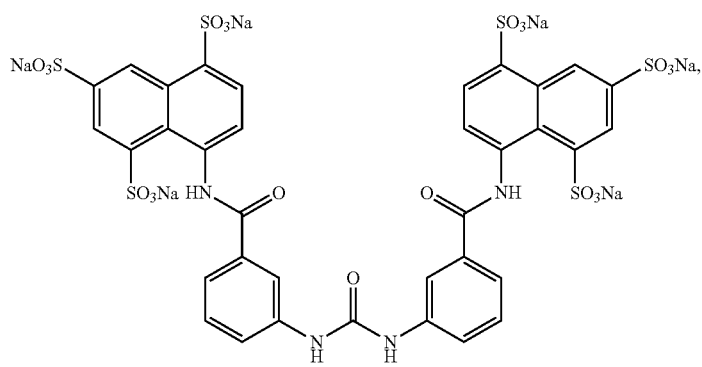
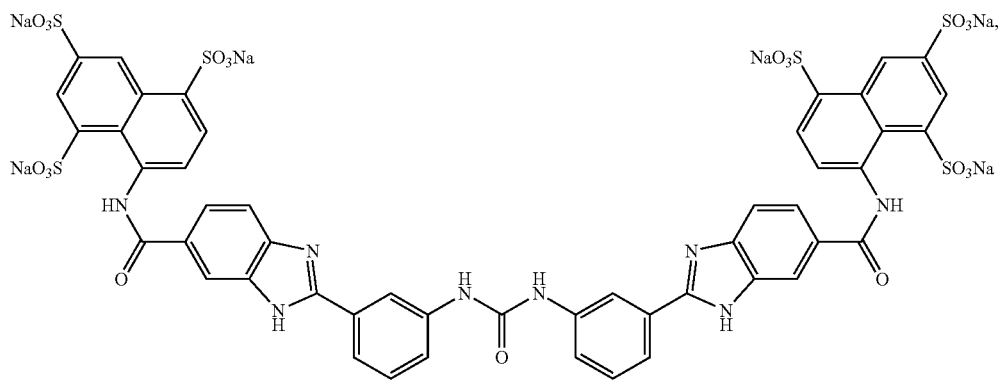
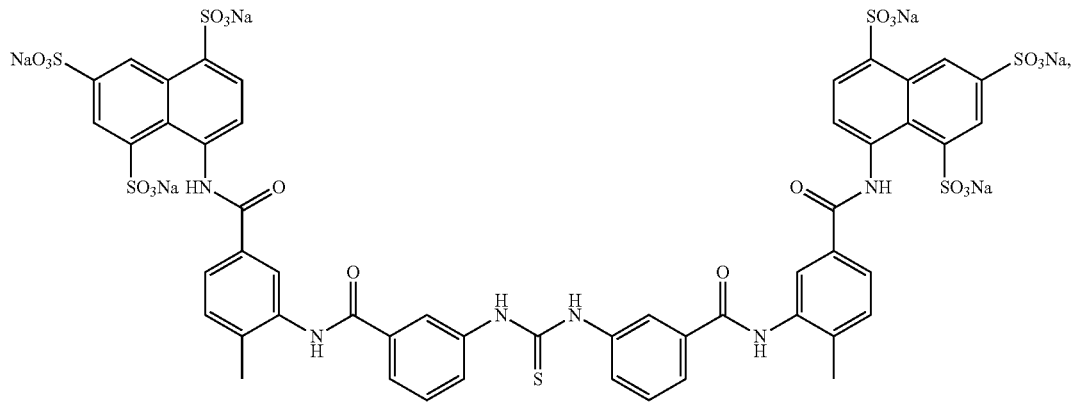

-continued
89
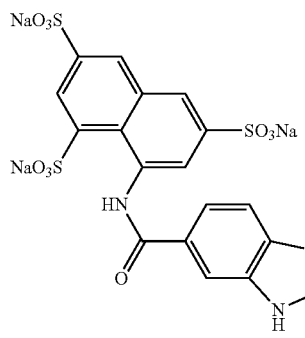
90
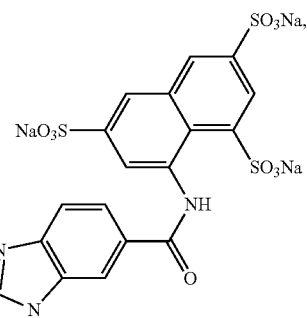
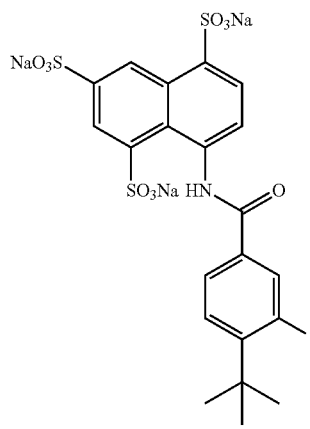
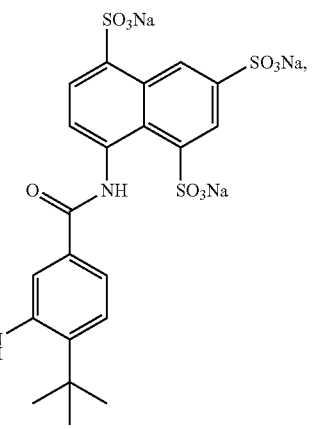
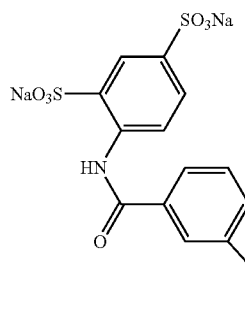
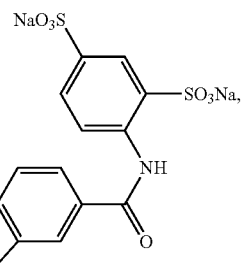
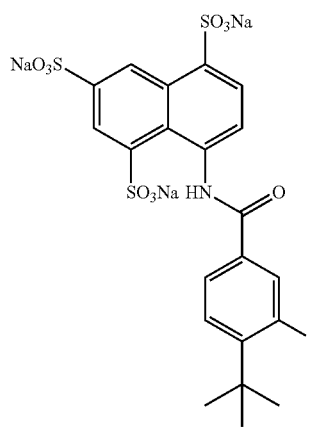
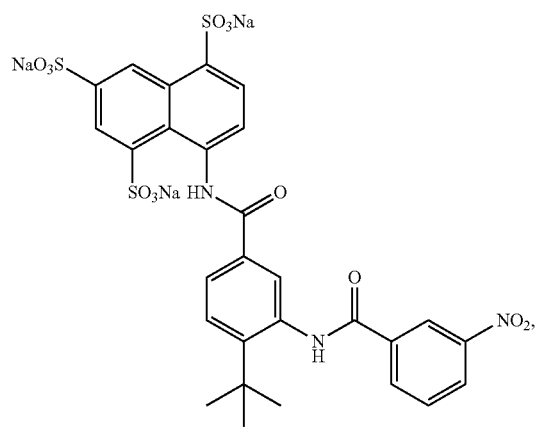

-continued
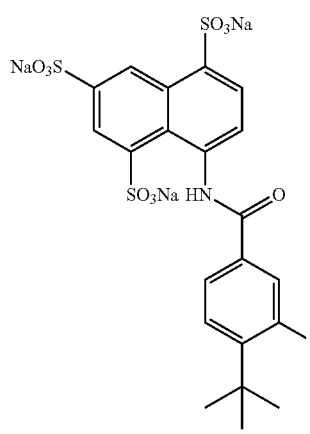
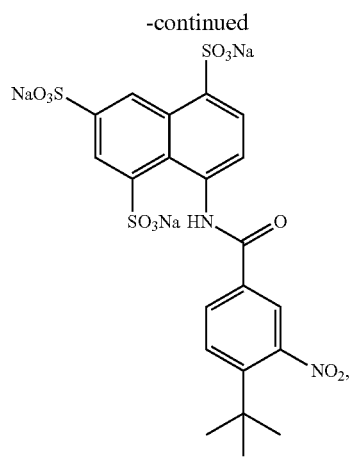
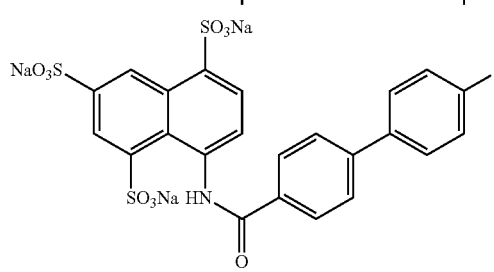
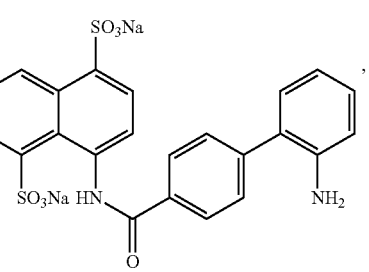
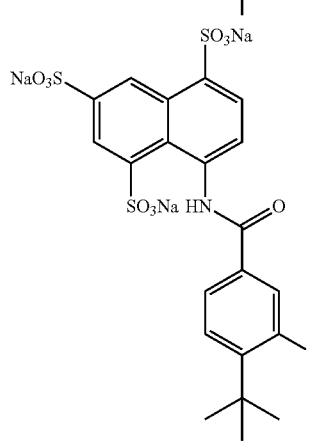
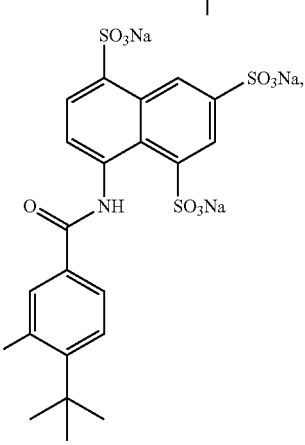
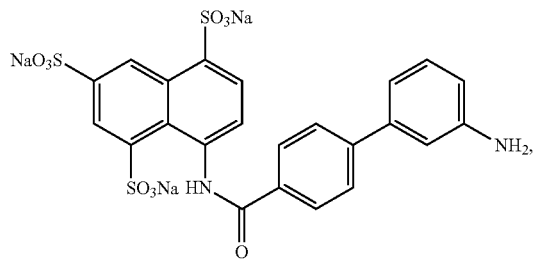
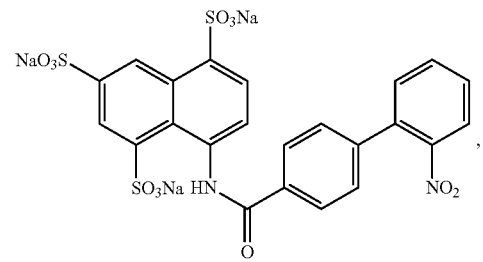
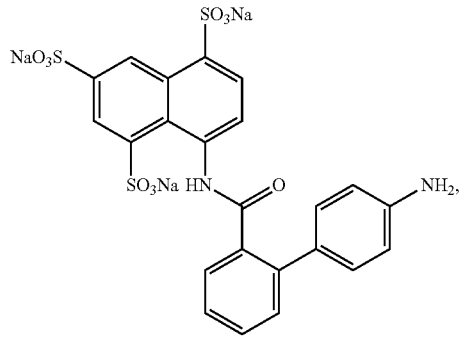
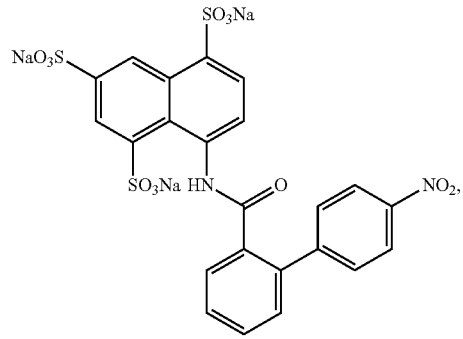

93 94
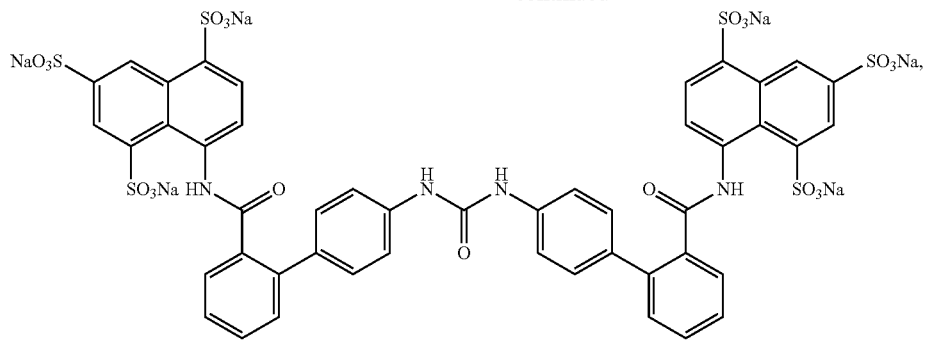
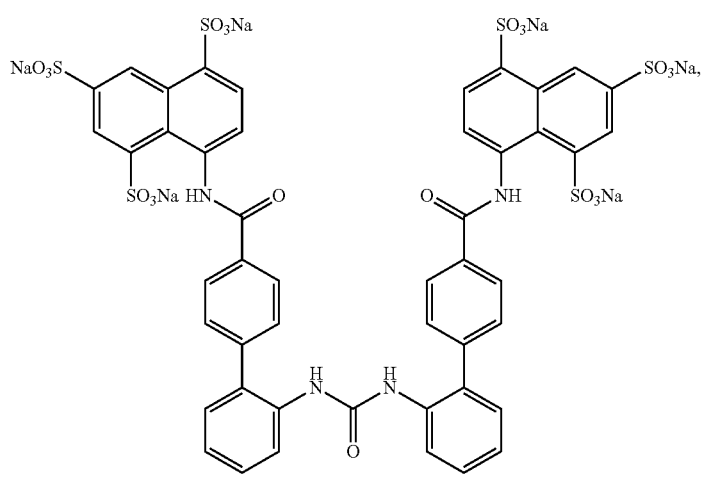
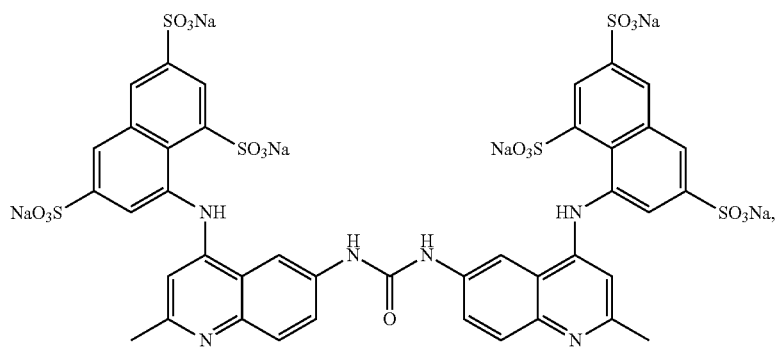
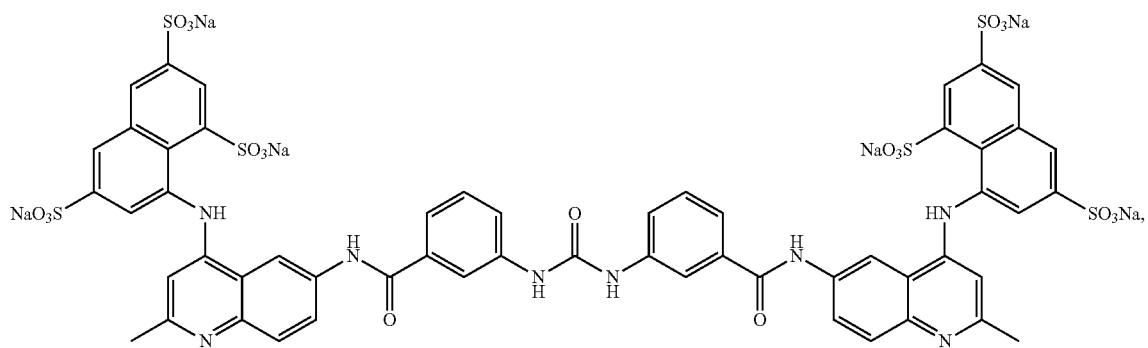

-continued
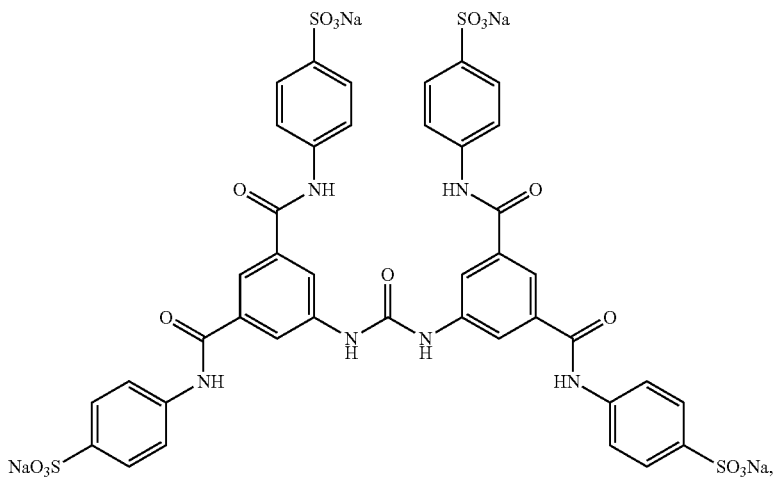
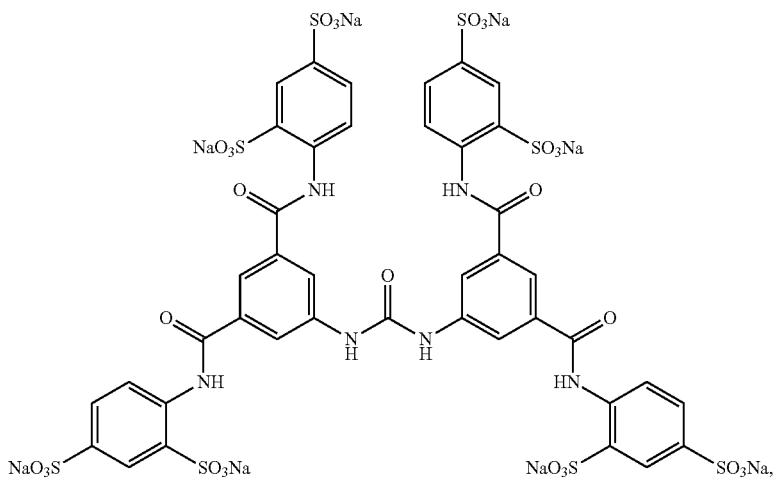
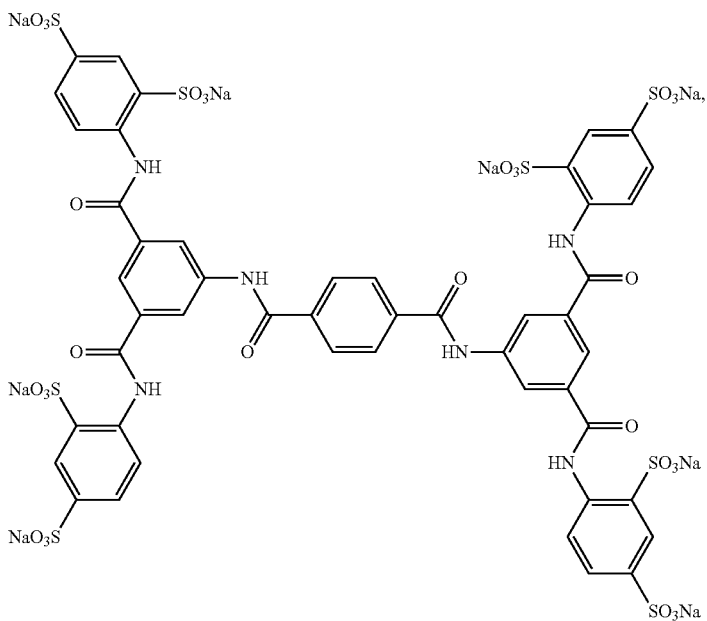

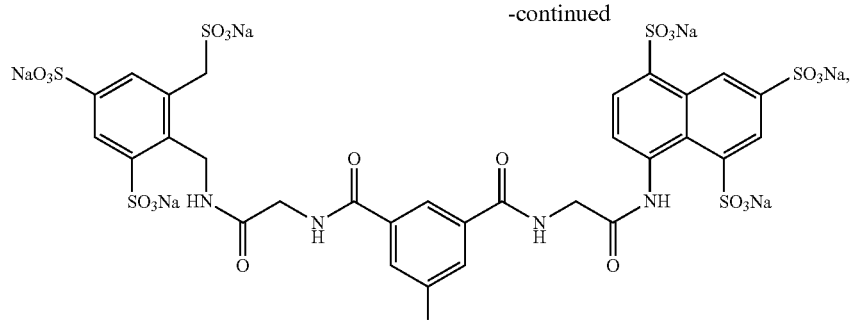
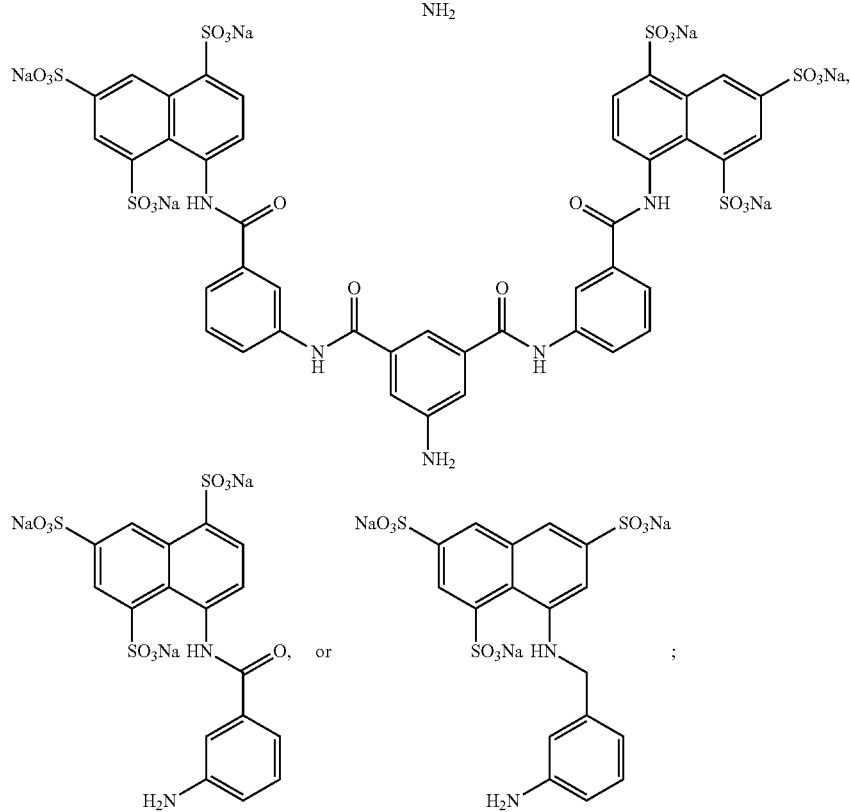
and wherein the carbohydrate or glycomimetic is:
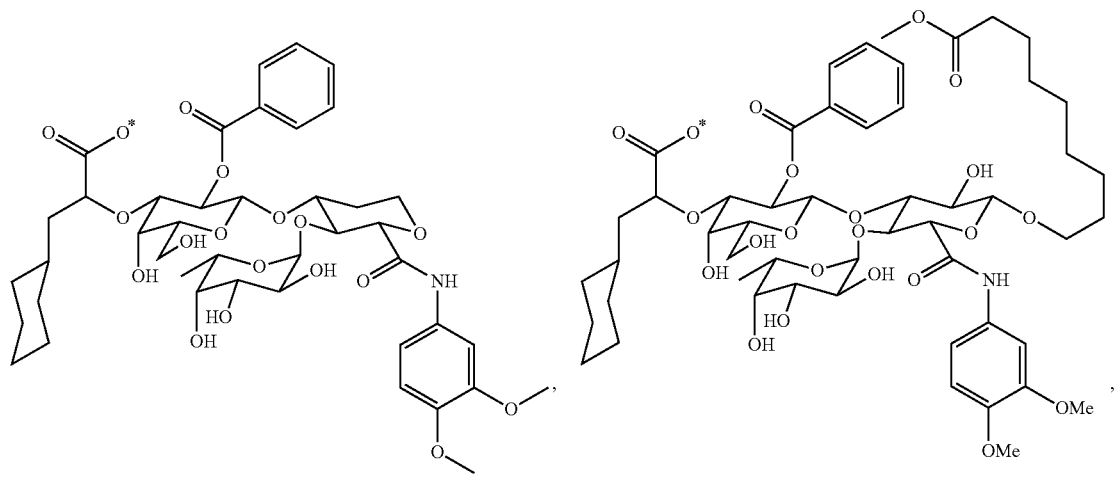

-continued
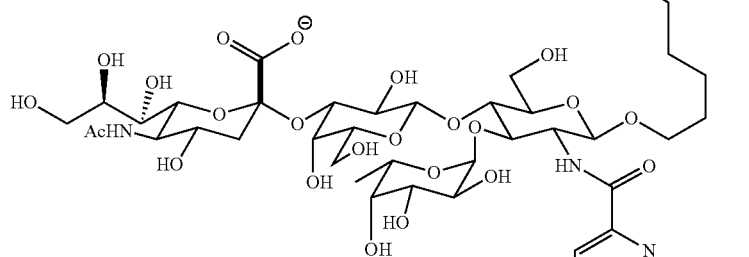
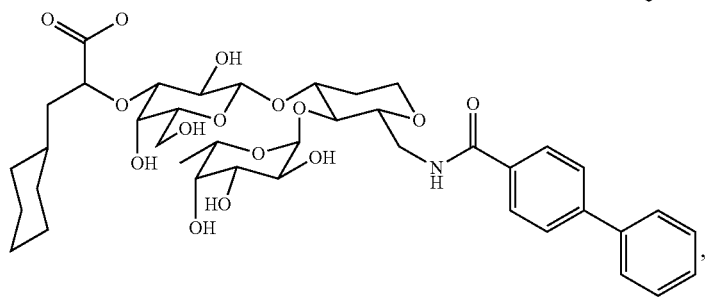
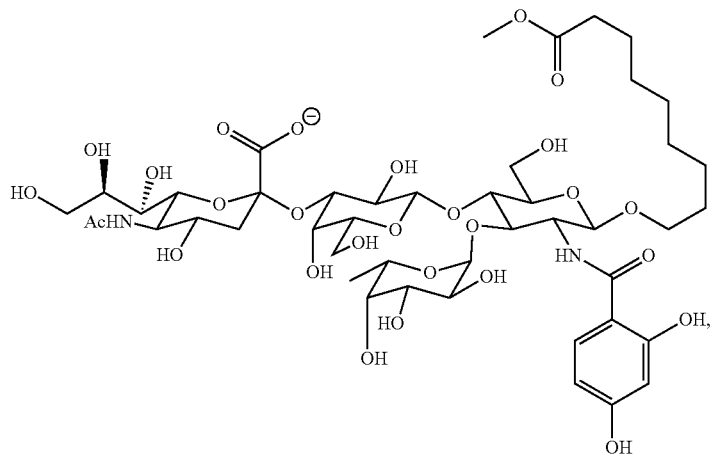
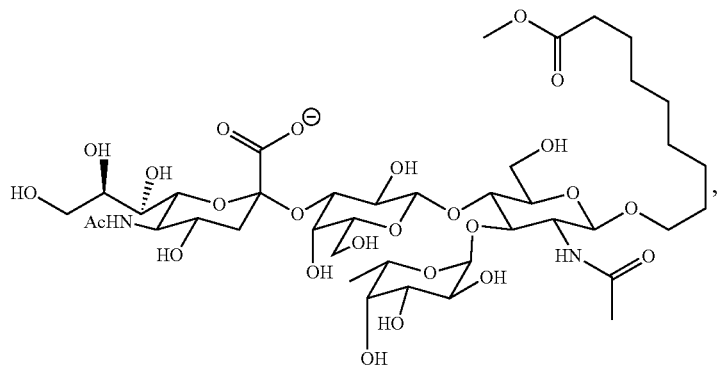

-continued
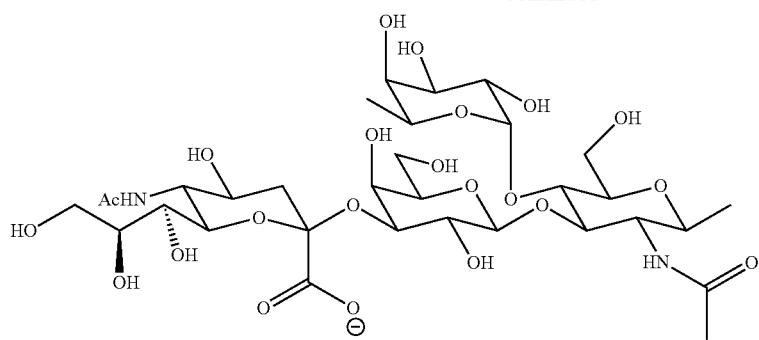
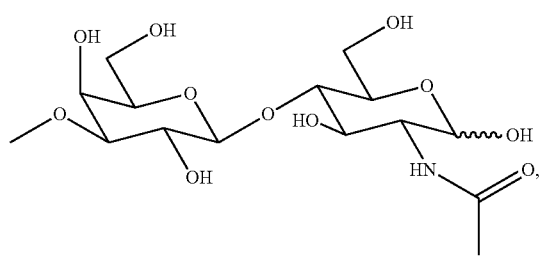
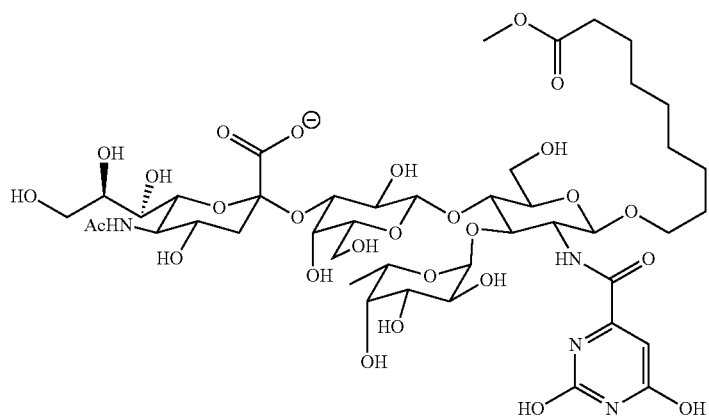
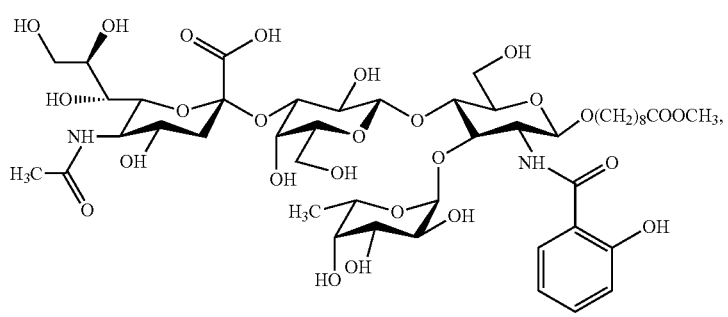
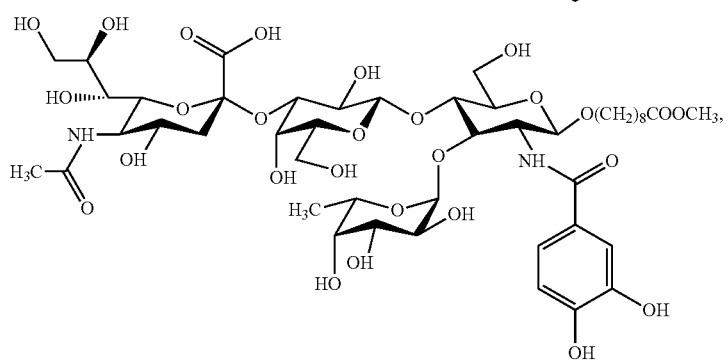

-continued
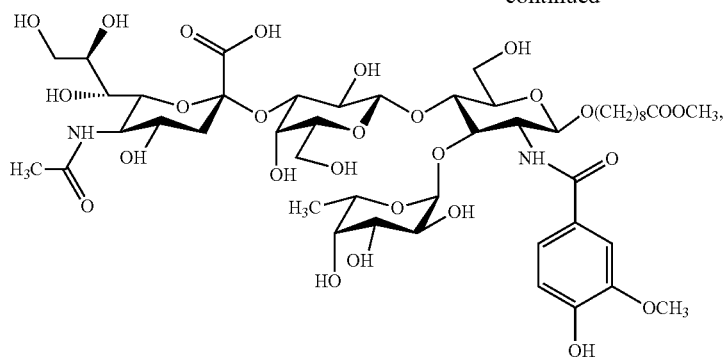
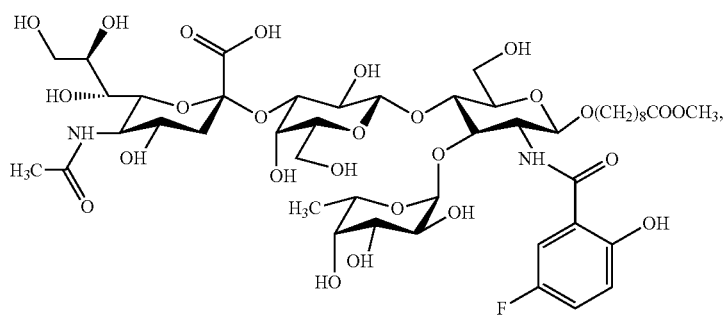
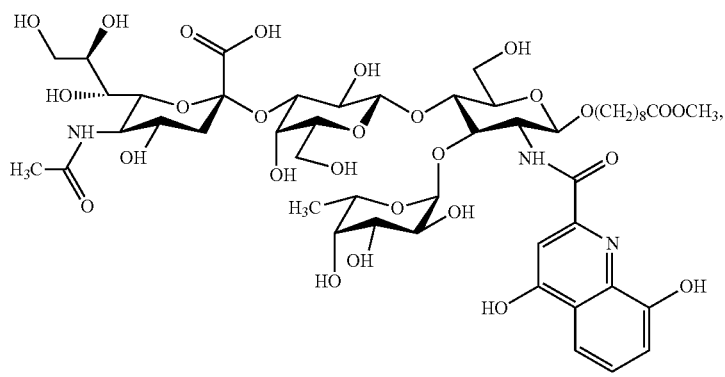
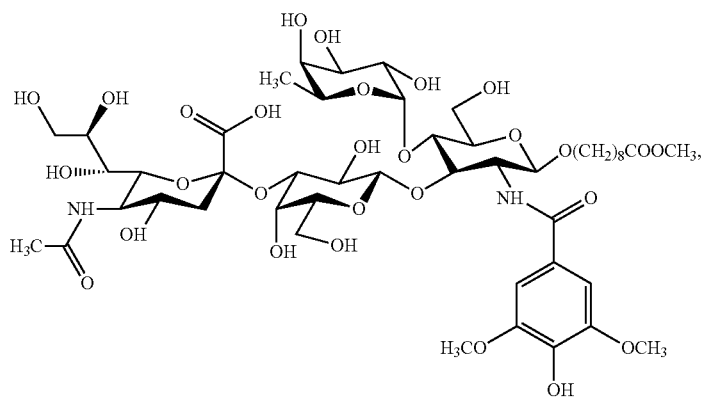

-continued
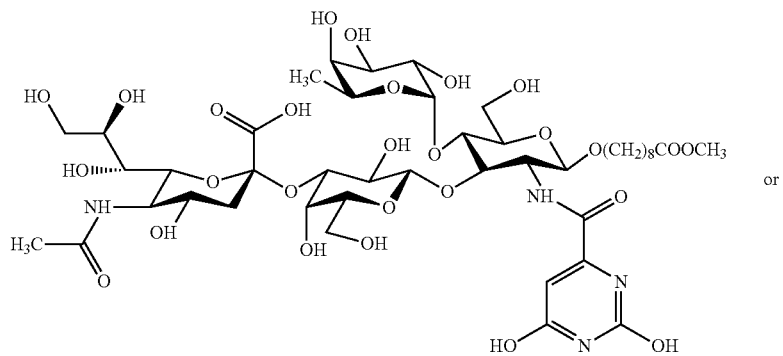
or
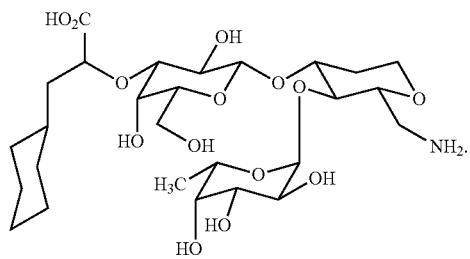
Non-limiting examples of such compounds include:
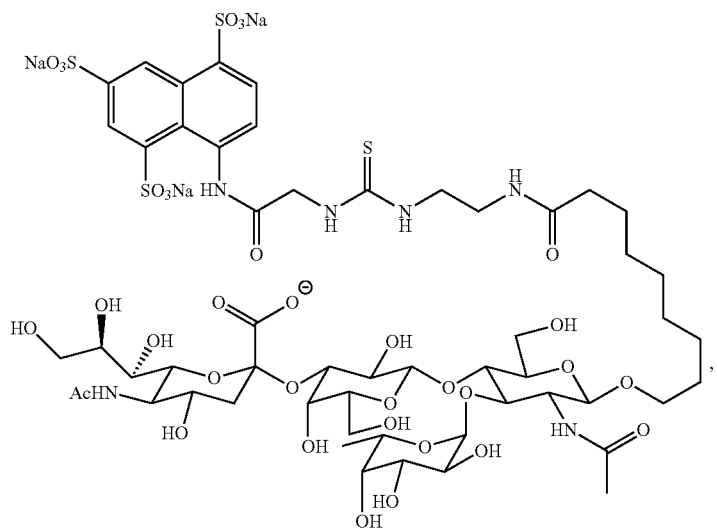

-continued
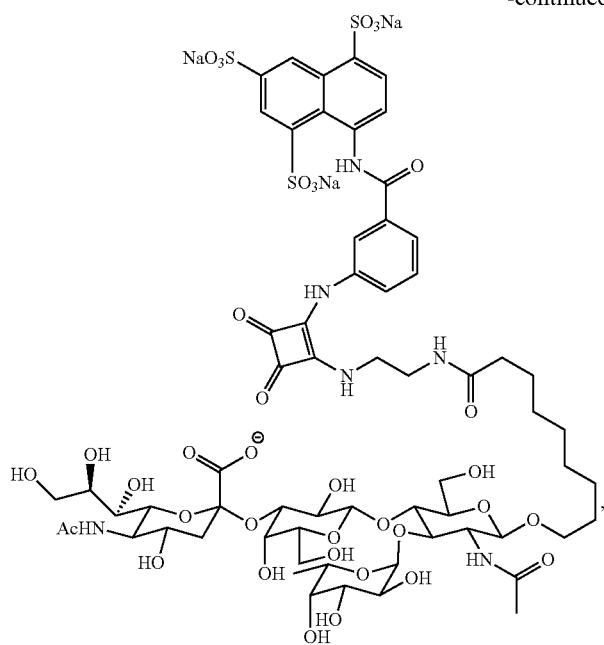
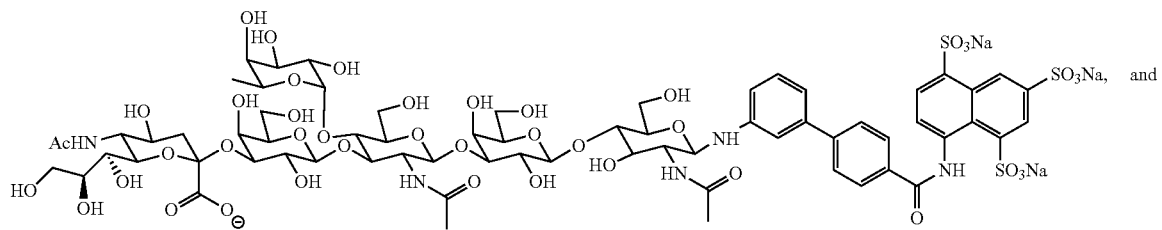
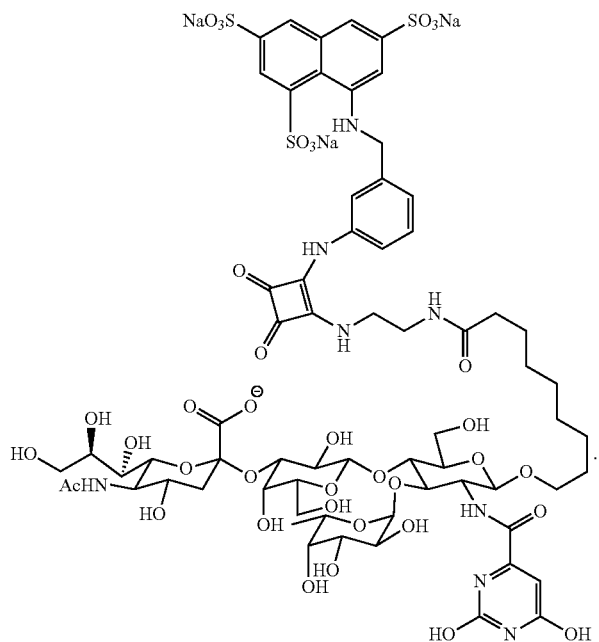

Still other carbohydrate inhibitors by Magnani et al. are disclosed in U.S. Pat. No. 6,121,233, 6,387,884 or 6,391,857, which are expressly incorporated herein by reference in their entirety. These compounds are represented by a formula selected from the group consisting of:

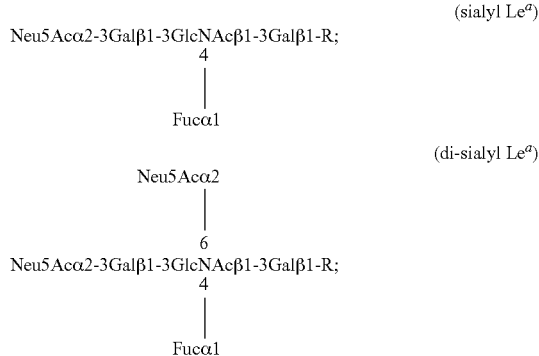

isomers of sialyl Le$^a$ or di-sialyl Le$^a$;

saccharides that include or consist of carbohydrate portions of sialyl Le$^a$ or di-sialyl Le$^a$; and glycoconjugates that include a carbohydrate portion of sialyl Le$^a$ or di-sialyl Le$^a$, wherein:

Neu5Ac represents sialic acid; Gal represents galactose; GlcNAc represents N-acetyl-glucosamine; Fuc represents fucose and R is typically a ceramide (with a glucose residue interposed) or a protein.

Illustrative examples of isomers of the above compounds include sialyl Le$^x$, which is an isomer of sialyl Le$^a$ wherein the Gal-GlcNAc linkage is β1-4 and the Fuc-GlcNAc linkage is α1→3.

Representative saccharides include the carbohydrate portion of sialyl Le$^a$ or di-sialyl Le$^a$ (i.e., the above structures minus R), and derivatives of either, including those which cross-react with both sialyl Le$^a$ and sialyl Le$^x$ Non-limiting examples of glycoconjugates may be represented by the following structures:

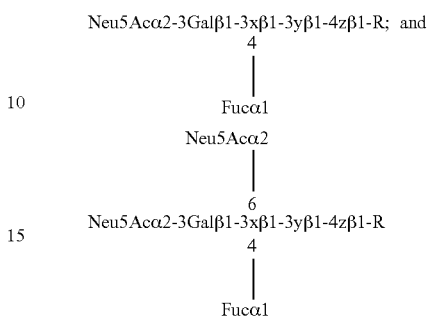

wherein:

R includes H, OH, lipid, ceramide, or one or more amino acids; x, y and z are independently selected from saccharides, or either y or z or both may be absent.

In still other embodiments, the carbohydrate inhibitor is selected from fluorinated glucosamine analogs as disclosed for example by Sackstein et al. in US Pat. Appl. Pub. No. 2006/0281708, which is expressly incorporated herein by reference in its entirety. Representative analogs of this type are fluorinated N-acetylglucosamines, illustrative examples of which include 2-acetamido-2-deoxy-1,3,6-tri-O-acetyl-4-deoxy-4-fluoro-D-glucopyranose and 2-acetamido-2-deoxy-1,4,6-tri-O-acetyl-3-deoxy-3-fluoro-D-glucopyranose.

In other illustrative examples, the carbohydrate inhibitor is selected from the selective E-selectin antagonist compounds described by Thoma et al. (2001, *Bioorg. Med. Chem. Letts.* 11: 923-925), which is expressly incorporated herein by reference in its entirety. These compounds are selected from the following formulas:

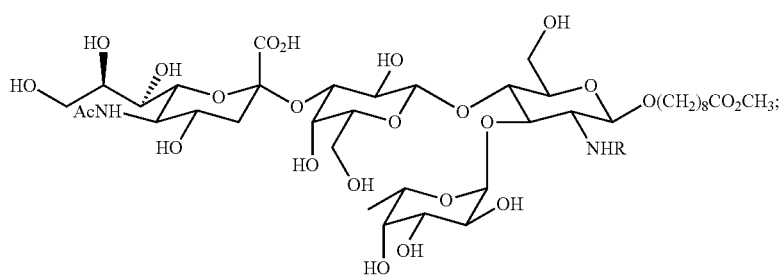

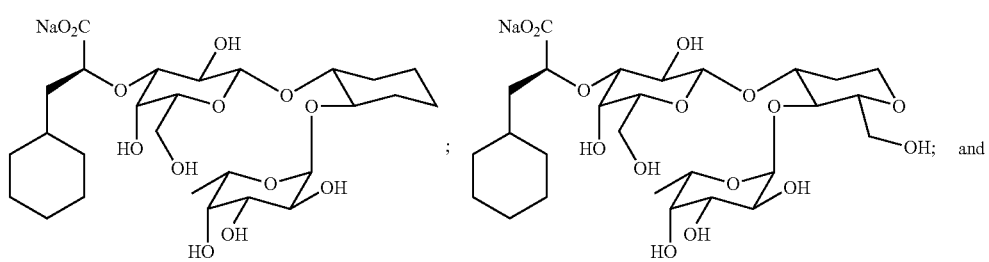

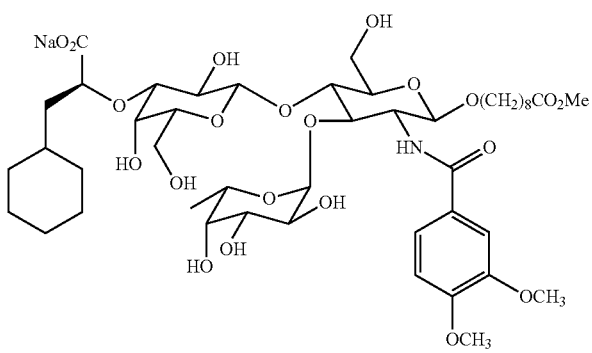

In still other illustrative examples, the carbohydrate inhibitor is selected from the selective E-selectin antagonist compounds described by Ali et al. (FASEB J. 2004 January; 18(1):152-4), which is expressly incorporated herein by reference in its entirety. Non-limiting examples of these compounds include monovalent E-selectin antagonists selected from:

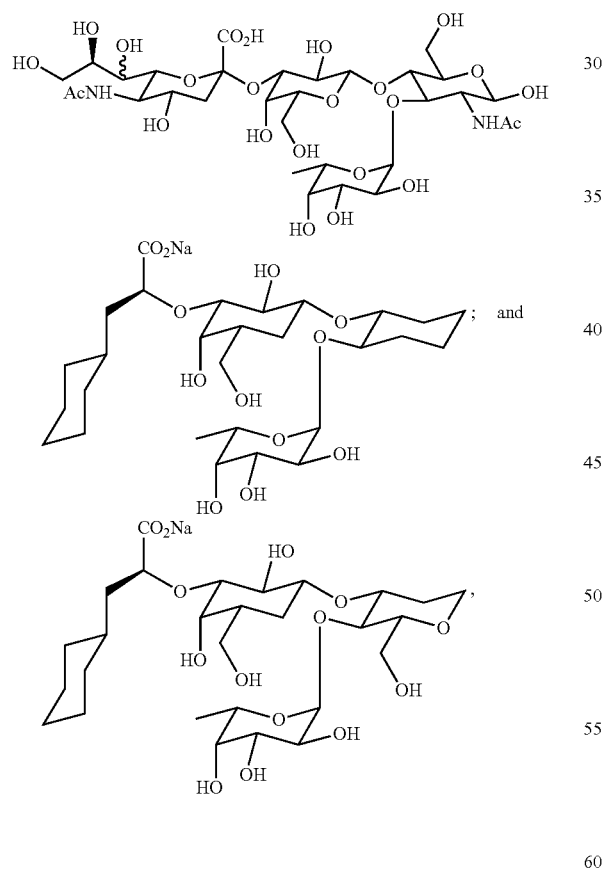

as well as multivalent-selectin antagonists selected from:

polylysine-a sialyl Lewis$^x$ mimetic conjugates as represented by the formula:

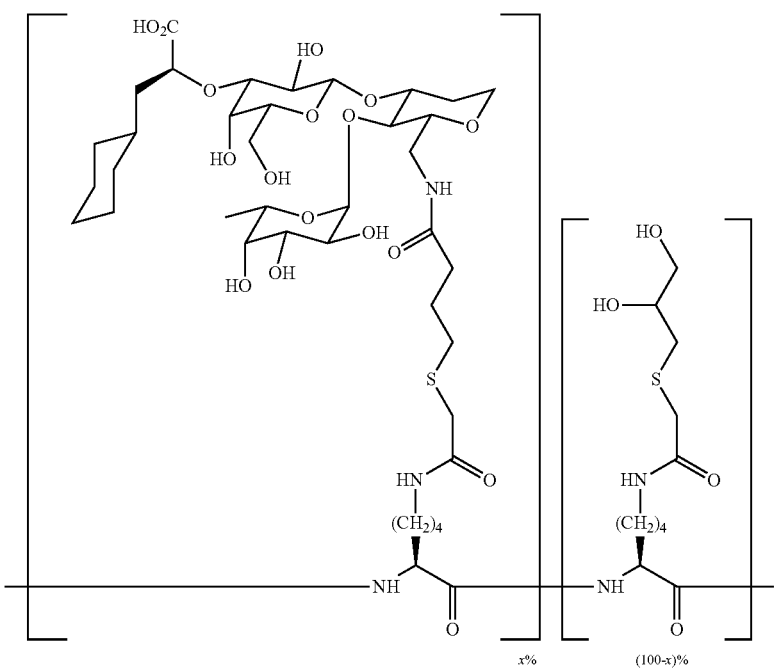

wherein x = 1-100.

The invention not only encompasses known E-selectin antagonists but also antagonists identified by any suitable screening assay. Accordingly, the present invention extends to methods of screening for modulatory agents that reduce the level or functional activity of E-selectin for use in the therapeutic or prophylactic methods and compositions of the present invention. In some embodiments, the methods comprise: (1) contacting a preparation with a test agent, wherein the preparation contains (i) a polypeptide comprising an amino acid sequence corresponding to at least a biologically active fragment of an E-selectin polypeptide, or to a variant or derivative thereof; or (ii) a polynucleotide comprising at least a portion of a genetic sequence that regulates the level or functional activity of the E-selectin polypeptide, which is operably linked to a reporter gene; and (2) detecting a change in the level and/or functional activity of the E-selectin polypeptide, or an expression product of the reporter gene, relative to a normal or reference level and/or functional activity in the absence of the test agent, which indicates that the agent modulates the level or functional activity of the E-selectin.

Modulators falling within the scope of the present invention include antagonists of the level or functional activity of E-selectin, including antagonistic antigen-binding molecules, and inhibitor peptide fragments, antisense molecules, ribozymes, RNAi molecules and co-suppression molecules as well as carbohydrate inhibitors of E-selectin function, as for example described above.

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of a E-selectin polypeptide are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (eg by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc to produce structural analogues.

Screening may also be directed to known pharmacologically active compounds and chemical analogues thereof.

Screening for modulatory agents according to the invention can be achieved by any suitable method. For example, the method may include contacting a cell expressing a polynucleotide corresponding to an E-selectin gene with an agent suspected of having the modulatory activity and screening for the modulation of the level or functional activity of a protein encoded by the polynucleotide, or the modulation of the level of a transcript encoded by the polynucleotide, or the modulation of the activity or expression of a downstream cellular target of the protein or of the transcript (hereafter referred to as target molecules). Detecting such modulation can be achieved utilizing techniques including, but not restricted to, ELISA, cell-based ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

It will be understood that a polynucleotide from which an E-selectin polypeptide is regulated or expressed may be naturally occurring in the cell which is the subject of testing or it may have been introduced into the host cell for the purpose of testing. In addition, the naturally-occurring or introduced polynucleotide may be constitutively expressed—thereby providing a model useful in screening for agents which downregulate expression of an encoded product of the sequence wherein the down regulation can be at the nucleic acid or expression product level. Further, to the extent that a polynucleotide is introduced into a cell, that polynucleotide may comprise the entire coding sequence that codes for an E-selectin polypeptide or it may comprise a portion of that coding sequence (e.g., the ligand-binding domain of an E-selectin polypeptide) or a portion that regulates expression of an E-selectin gene (e.g., an E-selectin promoter). For example, the promoter that is naturally associated with the polynucleotide may be introduced into the cell that is the subject of testing. In this instance, where only the promoter is utilized, detecting modulation of the promoter activity can be achieved, for example, by operably linking the promoter to a suitable reporter polynucleotide including, but not restricted to, green fluorescent protein (GFP), luciferase, β-galactosidase and catecholamine acetyl transferase (CAT). Modulation of expression may be determined by measuring the activity associated with the reporter polynucleotide.

These methods provide a mechanism for performing high throughput screening of putative modulatory agents such as proteinaceous or non-proteinaceous agents comprising synthetic, combinatorial, chemical and natural libraries. These methods will also facilitate the detection of agents which bind either the polynucleotide encoding the target molecule or which modulate the expression of an upstream molecule, which subsequently modulates the expression of the polynucleotide encoding the target molecule. Accordingly, these methods provide a mechanism of detecting agents that either directly or indirectly modulate the expression or activity of a target molecule according to the invention.

In some embodiments, the present invention provides assays for identifying small molecules or other compounds (i.e., modulatory agents) which are capable of inhibiting the level or functional activity of E-selectin. The assays may be performed in vitro using non-transformed cells, immortalized cell lines, or recombinant cell lines. In addition, the assays may detect the presence of increased or decreased expression of genes or production of proteins on the basis of increased or decreased mRNA expression (using, for example, nucleic acid probes that hybridise to an E-selectin gene or coding sequence), increased or decreased levels of E-selectin (using, for example, antigen binding molecules that are immuno-interactive with an E-selectin polypeptide), or increased or decreased levels of expression of a reporter gene (e.g., GFP, β-galactosidase or luciferase) operably linked to an E-selectin regulatory region (e.g., a promoter or enhancer) in a recombinant construct.

Thus, for example, one may culture cells which produce an E-selectin polypeptide and add to the culture medium one or more test compounds. After allowing a sufficient period of time (e.g., 6-72 hours) for the compound to inhibit the level or functional activity of the E-selectin polypeptide, any change in the level from an established baseline may be detected using, for example, any of the techniques described herein or known in the art. In specific embodiments, the cells are hemopoietic stem cells. Using suitable nucleic acid probes or antigen-binding molecules, detection of changes in the level and or functional activity of an E-selectin expression product, and thus identification of the compound as agonist or antagonist of the target molecule, requires only routine experimentation.

In some embodiments, recombinant assays are employed in which a reporter gene encoding, for example, GFP, β-galactosidase or luciferase is operably linked to the 5' regulatory regions of an E-selectin gene. Such regulatory regions may be easily isolated and cloned by one of ordinary skill in the art. The reporter gene and regulatory regions are joined in-frame (or in each of the three possible reading frames) so that transcription and translation of the reporter gene may proceed under the control of the regulatory elements of the E-selectin gene. The recombinant construct may then be introduced into any appropriate cell type although mammalian cells are desirable, and human cells are more desirable. The transformed cells may be grown in culture and, after establishing the baseline level of expression of the reporter gene, test compounds may be added to the medium. The ease of detection of the expression of the reporter gene provides for a rapid, high throughput assay for the identification of E-selectin antagonists of the invention.

Compounds identified by this method will have potential utility in modifying the expression of E-selectin in vivo. These compounds may be further tested in the animal models to identify those compounds having the most potent in vivo effects. In addition, as described above with respect to small molecules having target polypeptide binding activity, these molecules may serve as "lead compounds" for the further development of pharmaceuticals by, for example, subjecting the compounds to sequential modifications, molecular modeling, and other routine procedures employed in rational drug design.

In other embodiments, random peptide libraries consisting of a large number of possible combinations of amino acids attached to a solid phase support may be used to identify peptides that are able to bind to an E-selectin polypeptide or to a functional domain thereof. Identification of molecules that are able to bind to an E-selectin polypeptide may be accomplished by screening a peptide library with a recombinant soluble E-selectin polypeptide. The E-selectin polypeptide may be purified, recombinantly expressed or synthesised by any suitable technique. Such polypeptides may be conveniently prepared by a person skilled in the art using standard protocols as for example described in Sambrook, et al., (1989, supra) in particular Sections 16 and 17; Ausubel et al., ("Current Protocols in Molecular Biology", John Wiley & Sons Inc, 1994-1998), in particular Chapters 10 and 16; and Coligan et al., ("Current Protocols in Immunology", (John Wiley & Sons, Inc, 1995-1997), in particular Chapters 1, 5 and 6. Alternatively, an E-selectin polypeptide or a portion thereof may be synthesised using solution synthesis or solid phase synthesis as described, for example, in Chapter 9 of Atherton and Shephard (supra) and in Roberge et al (1995, *Science* 269: 202).

To identify and isolate the peptide/solid phase support that interacts and forms a complex with the E-selectin polypeptide it may be necessary to label or "tag" the E-selectin polypeptide. In this regard, the E-selectin polypeptide can be conjugated to any suitable reporter molecule, including enzymes such as alkaline phosphatase and horseradish peroxidase and fluorescent reporter molecules such as fluorescein isothiocyanate (FITC), phycoerythrin (PE) and rhodamine. Conjugation of any given reporter molecule, with an E-selectin polypeptide, may be performed using techniques that are routine in the art. Alternatively, E-selectin expression vectors may be engineered to express a chimeric E-selectin polypeptide containing an epitope for which a commercially available antigen-binding molecule exists. The epitope specific antigen-binding molecule may be tagged using methods known in the art including labeling with enzymes, fluorescent dyes or colored or magnetic beads.

For example, the "tagged" E-selectin polypeptide conjugate is incubated with the random peptide library for 30 minutes to one hour at 22° C. to allow complex formation between E-selectin polypeptide and peptide species within the library. The library is then washed to remove any unbound E-selectin polypeptide. If the E-selectin polypeptide has been conjugated to alkaline phosphatase or horseradish peroxidase the whole library is poured into a petri dish containing a substrate for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-E-selectin polypeptide complex changes color, and can be easily identified and isolated physically under a dissecting microscope with a micromanipulator. If a fluorescently tagged E-selectin polypeptide has been used, complexes may be isolated by fluorescent activated sorting. If a chimeric target polypeptide having a heterologous epitope has been used, detection of the peptide/E-selectin polypeptide complex may be accomplished by using a labeled epitope specific antigen-binding molecule. Once isolated, the identity of the peptide attached to the solid phase support may be determined by peptide sequencing.

3.2 Mobilizers of Hematopoietic Stem Cells or Progenitor Cells

Several classes of agents have been shown to increase the circulation of progenitor and stem cells by "mobilizing" them from the marrow into the peripheral blood. These include agents that decrease the expression or function of a chemokine (the function being the binding of the chemokine to its receptor and further signaling), particularly CXCL12, as well as those that block or antagonize the chemokine receptor, CXCR4.

Accordingly, in some embodiments, the mobilization agent may be an agent that decreases the expression or function of a chemokine, more particularly, CXCL12, also known as SDF-1. The human amino acid sequence of SDF-1 comprises the sequence:

MNAKVVVVLVLVLTALCLSDGKPVSL-SYRCPCRFFESHVARANVKHLKILN TPNCALQI-VARLKNNNRQVCIDPKLKWIQEYLEKALNKRFKM [SEQ ID NO: 227], which corresponds to GenBank accession number NP_000600. The alpha isoform has GenBank accession number NP_954637. The beta isoform has GenBank accession number NP_000600. The gamma isoform has GenBank accession number NP_001029058.

Alternatively, the mobilization agent may be an agent that blocks or antagonizes a chemokine receptor, in particular, CXCR4. The human amino acid sequence of CXCR4 comprises the sequence:

MEGISSIPLPLLQIYTSDNYTEEMGS-GDYDSMKEPCFREENANFNKIFLPT IYSIIFLT-GIVGNGLVILVMGYQKKLRSMTDKYR-LHLSVADLLFVITLPFWAVDAVANWYFG NFLCKAVHVIYTVNLYSSVLILAFISLD-RYLAIVHATNSQRPRKLLAEKVVYVGVWIPALLL TIPDFIFANVSEADDRYICDRFYPNDL-WVVVFQFQHIMVGLILPGIVILSCYCIIISKLSHS KGHQKRKALKTTVILILAFFACWLPYYIGI-SIDSFILLEIIKQGCEFENTVHKWISITEALA FFHC-CLNPILYAFLGAKFKTSAQHALTSVS-RGSSLKILSKGKRGGHSSVSTESESSSFHSS [SEQ ID NO: 228], which corresponds to GenBank accession number CAA12166.

Chemokines are a superfamily of chemoattractant proteins. Chemokines regulate a variety of biological responses and they promote the recruitment of multiple lineages of leukocytes and lymphocytes to a body organ tissue. Chemokines may be classified into two families according to the relative position of the first two cysteine residues in the protein. In one family, the first two cysteines are separated by one amino acid residue, the CXC chemokines, and in the other family the first two cysteines are adjacent, the CC chemokines. Two minor subgroups contain only one of the two cysteines (C) or have three amino acids between the cysteines (CX3C). In humans, the genes of the CXC chemokines are clustered on chromosome 4 (with the exception of SDF-1 gene, which has been localized to chromosome 10) and those of the CC chemokines on chromosome 17.

The molecular targets for chemokines are cell surface receptors. One such receptor is CXC chemokine receptor 4 (CXCR4), which is a 7 transmembrane protein, coupled to G1 and was previously called LESTR (Loetscher, M., Geiser, T., O'Reilly, T., Zwahlen, R., Baggionlini, M., and Moser, B., (1994) J. Biol. Chem., 269, 232-237), HUMSTR (Federspiel, B., Duncan, A. M. V., Delaney, A., Schappert, K., Clark-Lewis, I., and Jirik, F. R. (1993) Genomics 16, 707-712) and Fusin (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877). CXCR4 is widely expressed on cells of hematopoietic origin, and is a major co-receptor with CD4 for human immunodeficiency virus 1 (HIV-1) (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877).

Chemokines are thought to mediate their effect by binding to seven transmembrane G protein-coupled receptors, and to attract leukocyte subsets to sites of inflammation (Baglionini et al. (1998) Nature 392: 565-568). Many of the chemokines have been shown to be constitutively expressed in lymphoid tissues, indicating that they may have a homeostatic function in regulating lymphocyte trafficking between and within lymphoid organs (Kim and Broxmeyer (1999) J. Leuk. Biol. 56: 6-15).

Stromal cell derived factor one (SDF=1), also known as CXCL12, is a member of the CXC family of chemokines that has been found to be constitutively secreted from the bone marrow stroma (Tashiro, (1993) Science 261, 600-602). The human and mouse SDF-1 predicted protein sequences are approximately 92% identical. Stromal cell derived factor-1α (SDF-1α) and stromal cell derived factor-1β (SDF-1β) are closely related (together referred to herein as SDF-1). The native amino acid sequences of SDF-1α and SDF-1β are known, as are the genomic sequences encoding these proteins (see U.S. Pat. No. 5,563,048 issued 8 Oct. 1996, and U.S. Pat. No. 5,756,084 issued 26 May 1998). Identification of genomic clones has shown that the alpha and beta isoforms are a consequence of alternative splicing of a single gene. The alpha form is derived from exons 1-3 while the beta form contains an additional sequence from exon 4. The entire human gene is approximately 10 kb. SDF-1 was initially characterized as a pre-B cell-stimulating factor and as a highly efficient chemotactic factor for T cells and monocytes (Bieul et al. (1996) J. Exp. Med. 184:1101-1110).

Biological effects of SDF-1 may be mediated by the chemokine receptor CXCR4 (also known as fusin or LESTR), which is expressed on mononuclear leukocytes including hematopoietic stem cells. SDF-1 is thought to be the natural ligand for CXCR4, and CXCR4 is thought to be the natural receptor for SDF-1 (Nagasawza et al. (1997) Proc. Natl. Acad. Sci. USA 93:726-732). Genetic elimination of SDF-1 is associated with perinatal lethality, including abnormalities in cardiac development, B-cell lymphopoiesis, and bone marrow myelopoiesis (Nagasawa et al. (1996) Nature 382:635-637). SDF-1 is functionally distinct from other chemokines in that it is reported to have a fundamental role in the trafficking, export and homing of bone marrow progenitor cells (Aiuti, A., et al. (1996) J. Exp. Med. 185, 111-120 and Nagasawa, T., et al. (1996) Nature 382, 635-638). SDF-1 is also structurally distinct in that it has only about 22% amino acid sequence identity with other CXC chemokines.

Agents that decrease the expression of CXCL12 or that block or antagonize CXCR4 may be selected from small organic molecules, polypeptides, nucleic acids and carbohydrates. In more particular embodiments, the polypeptides that decrease the expression of CXCL12 may be selected from the group consisting of a cytokine, a colony stimulating factor, a protease or a chemokine other than CXCL12. The cytokine may be selected from the group consisting of interleukin-1 (IL-1), interleukin-3 (IL-3), interleukin-6 (IL-6), interleukin-11 (IL-11), interleukin-7 (IL-7) and interleukin-12 (IL12). The protease may be selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26). The chemokine other than CXCL12 may be selected from the group consisting of IL-8, MIP-1α and Groβ. The colony stimulating factor may be selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof. The nucleic acid may be a DNA or an RNA molecule. The nucleic acid may be a small interfering RNA (siRNA) molecule or an antisense molecule specific for CXCL12 or CXCR4. The carbohydrate may be a sulfated carbohydrate selected from the group consisting of Fucoidan and sulfated dextran.

4. Therapeutic and Prophylactic Uses

In accordance with the present invention, it is proposed that agents that antagonize E-selectin function are useful as actives for enhancing the hemopoietic properties of mobilizers of hematopoietic stem cells and progenitor cells. Thus, an E-selectin antagonist can be administered to an individual in combination (e.g., in the same formulation or in separate formulations) with a mobilizer ("combination therapy") to enhance hematopoiesis including the mobilization of hematopoietic stem cells and progenitor cells and more particularly to increase the number of hematopoietic stem cells, progenitor cells and granulocytes such as neutrophils in a patient. The dosages of E-selectin antagonist and mobilizer to be administered may depend on the subject to be treated inclusive of the age, sex, weight and general health condition thereof. The dosages will also take into consideration the binding affinity of the E-selectin antagonist to its target molecule, the hematopoietic capacity of the mobilizer, their bioavailability and their in vivo and pharmacokinetic properties. In this regard, precise amounts of the agents for administration can also depend on the judgment of the practitioner. In determining the effective amount of the agents to be administered in the treatment of an immunocompromised condition, the physician or veterinarian may evaluate the progression of the disease or condition over time. In any event, those of skill in the art may readily determine suitable dosages of the agents of the invention without undue experimentation. The dosage of the actives administered to a patient should be sufficient to effect a beneficial response in the patient over time such as enhanced hematopoiesis or a reduction in the symptoms associated with the immunocompromised condition, including a reduction in anemia, thrombocytopenia, agranulocytosis and/or neutropenia. The dosages may be administered at suitable intervals to boost hematopoiesis or ameliorating the symptoms of the immunocompromised condition. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

Dosage amount and interval may be adjusted individually to provide plasma levels of the active agent which are sufficient to maintain E-selectin-inhibitory effects and hematopoietic function enhancing effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Thus, the E-selectin antagonist and the mobilizer may be provided in effective amounts to stimulate or enhance hematopoiesis. This process may involve administering the E-selectin antagonist separately, simultaneously or sequentially with the mobilizer. In some embodiments, this may be achieved by administering a single composition or pharmacological formulation that includes both agents, or by administering two separate compositions or formulations at the same time, wherein one composition includes the E-selectin antagonist and the other, the mobilizer. In other embodiments, the treatment with the E-selectin antagonist may precede or follow the treatment with the mobilizer by intervals ranging from minutes to days. In embodiments where the E-selectin antagonist is applied separately to the mobilizer, one would generally ensure that a significant period of time did not expire between the time of each delivery, such that the E-selectin antagonist would still be able to exert an advantageously combined effect on hematopoiesis with the mobilizer, in particular, to maintain or enhance a subject's capacity to mobilize hematopoietic stem cells and progenitor cells and to increase the number of granulocytes such as neutrophils. In such instances, it is contemplated that one would administer both modalities within about 1-12 hours of each other and, more suitably, within about 2-6 hours of each other. In some situations, it may be desirable to extend the time period for treatment significantly, however, where several hours (2, 3, 4, 5, 6 or 7) to several days (1, 2, 3, 4, 5, 6, 7 or 8) lapse between the respective administrations.

It is conceivable that more than one administration of either the E-selectin antagonist or mobilizer will be desired. Various combinations may be employed, where the E-selectin antagonist is "A" and the mobilizer is "B", as exemplified below:

A/B/A B/A/B B/B/A A/A/B B/A/A A/B/B B/B/B/A B/B/ A/B A/A/B/B A/B/A/B A/B/B/A B/B/A/A B/A/B/A B/A/ A/B B/B/B/A A/A/A/B B/A/A/A A/B/A/A A/A/B/A A/B/ B/B B/A/B/B B/B/A/B.

Other combinations are contemplated. Again, both agents are delivered to a subject's immune system in a combined amount effective to enhance hematopoiesis as compared to the administration of the same amount of mobilizer alone.

As note above, the combination therapy of the present invention finds utility inter alia in the treatment or prophylaxis of immunocompromised conditions resulting from medical treatment that target hematopoietic stem cells, such as treatments that target rapidly dividing cells or that disrupt the cell cycle or cell division. The E-selectin antagonist and mobilizer may be used therapeutically after the medical treatment or may be used prophylactically before the treatment is administered or together with the medical treatment. Accordingly, the present invention contemplates further combination therapies which employ both a medical treatment that induces an immunocompromised condition and concurrent administration of an E-selectin antagonist and a mobilizer of hematopoietic stem cells or progenitor cells.

It is well known that chemotherapy and radiation therapy target rapidly dividing cells and/or disrupt the cell cycle or cell division. These treatments are offered as part of the treating several forms of cancer and autoimmune disease, aiming either at slowing their progression or reversing the symptoms of disease by means of a curative treatment. In some embodiments, therefore, the combination therapy or prophylaxis will additionally employ a chemotherapeutic agent, which is suitable selected from cytostatic agents and cytotoxic agents. Non-limiting examples of cytostatic agents are selected from: (1) microtubule-stabilizing agents such as but not limited to taxanes, paclitaxel, docetaxel, epothilones and laulimalides; (2) kinase inhibitors, illustrative examples of which include Iressa®, Gleevec, Tarceva™, (Erlotinib HCl), BAY-43-9006, inhibitors of the split kinase domain receptor tyrosine kinase subgroup (e.g., PTK787/ZK 222584 and SU11248); (3) receptor kinase targeted antibodies, which include, but are not limited to, Trastuzumab (Herceptin®), Cetuximab (Erbitux®), Bevacizumab (Avastin™), Rituximab (Ritusan®), Pertuzumab (Omnitarg™); (4) mTOR pathway inhibitors, illustrative examples of which include rapamycin and CCI-778; (5) Apo2L/Trail, anti-angiogenic agents such as but not limited to endostatin, combrestatin, angiostatin, thrombospondin and vascular endothelial growth inhibitor (VEGI); (6) antineoplastic immunotherapy vaccines, representative examples of which include activated T-cells, non-specific immune boosting agents (i.e., interferons, interleukins); (7) antibiotic cytotoxic agents such as but not limited to doxorubicin, bleomycin, dactinomycin, daunorubicin, epirubicin, mitomycin and mitozantrone; (8) alkylating agents, illustrative examples of which include Melphalan, Carmustine, Lomustine, Cyclophosphamide, Ifosfamide, Chlorambucil, Fotemustine, Busulfan, Temozolomide and Thiotepa; (9) hormonal antineoplastic agents, non-limiting examples of which include Nilutamide, Cyproterone acetate, Anastrozole, Exemestane, Tamoxifen, Raloxifene, Bicalutamide, Aminoglutethimide, Leuprorelin acetate, Toremifene citrate, Letrozole, Flutamide, Megestrol acetate and Goserelin acetate; (10) gonadal hormones such as but not limited to Cyproterone acetate and Medoxyprogesterone acetate; (11) antimetabolites, illustrative examples of which include Cytarabine, Fluorouracil, Gemcitabine, Topotecan, Hydroxyurea, Thioguanine, Methotrexate, Colaspase, Raltitrexed and Capicitabine; (12) anabolic agents, such as but not limited to, Nandrolone; (13) adrenal steroid hormones, illustrative examples of which include Methylprednisolone acetate, Dexamethasone, Hydrocortisone, Prednisolone and Prednisone; (14) neoplastic agents such as but not limited to Irinotecan, Carboplatin, Cisplatin, Oxaliplatin, Etoposide and Dacarbazine; and (15) topoisomerase inhibitors, illustrative examples of which include topotecan and irinotecan.

Illustrative cytotoxic agents can be selected from sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycaminomycin, annamycin, galarubicin, elinafide, MEN10755, 4-demethoxy-3-deamino-3-aziridinyl-4-methylsulphonyl-daunombicin (see International Publication WO 00/50032), methoxtrexate, gemcitabine, and mixture thereof.

In some embodiments, the concurrent administration of the E-selectin antagonist and the mobilizer is used in combination with radiotherapies, such as but not limited to, conformal external beam radiotherapy (10-100 Grey given as fractions over 4-8 weeks), either single shot or fractionated, high dose rate brachytherapy, permanent interstitial brachytherapy, systemic radio-isotopes (e.g., Strontium 89). In illustrative examples of this type, the radiotherapy is administered in combination with a radiosensitizing agent. Illustrative examples of radiosensitizing agents include but are not limited to efaproxiral, etanidazole, fluosol, misonidazole, nimorazole, temoporfin and tirapazamine.

Immunocompromised conditions generally lead to pathogenic infections and thus the present invention also extends to the treatment and/or prophylaxis of infections in individuals suffering from an immunocompromised condition, or to treatment of individuals who are likely to contract such a condition due to treatment known to be associated with the occurrence of an immunocompromised condition. Accordingly, an immunocompromised condition arising from a medical treatment is likely to expose the individual in question to a higher risk of infection. It is possible according to the invention to prophylactically treat an infection in an individual having the immunocompromised condition before or during treatments known to generate such a condition. By prophylactically treating with concurrent administration of the E-selectin antagonist and the mobilizer (also referred to herein as an "E-selectin antagonist/mobilizer combination") before or during a treatment known to generate an immunocompromised condition it is possible to prevent a subsequent infection or to reduce the risk of the individual contracting an infection manifesting from that condition. In some embodiments, therefore, the present invention extends to combination therapies, which employ both the E-selectin antagonist/mobilizer combination and an anti-infective agent that is effective against an infection that develops or that has an increased risk of developing from an immunocompromised condition resulting from a medical treatment as broadly described above.

The anti-infective drugs is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective drugs also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

It is also known that medical treatments that target rapidly dividing cells and/or disrupt the cell cycle or cell division (e.g., chemotherapy and radiation therapy) are immunocompromising since cells of the immune system including hematopoeitic cells are destroyed or substantially reduced in number, thus leading to a state of immunosuppression characterized by neutropenia, agranulocytosis, thrombocytopenia and/or anemia. Accordingly, the present invention finds particular utility in the treatment or prophylaxis of any one or more of these conditions that manifest from a medical treatment as broadly noted above.

Anemia, thrombocytopenia, neutropenia and agranulocytosis are frequently defined in terms of laboratory measurements indicating a reduced hematocrit (volume percent), a reduced platelet count (per $mm^3$), a reduced neutrophil count (per $mm^3$), a reduced total granulocyte (i.e., neutrophils, basophils and eosinophils) or white blood cell count (per $mm^3$), respectively. Methods of determining these values are well known in the art, including automated as well as manual methods. The lower limits of normal for hematocrits and platelet counts in healthy nonpregnant humans is somewhat variable, depending on the age and sex of the subject, method of determination, and the norms for the laboratory performing the measurements. Generally, however, an adult human subject is said to have anemia when the hematocrit is less than about 37-40%. Likewise, generally an adult human subject is said to have thrombocytopenia when the platelet count is below about 100,000 per $mm^3$. Anemia is also frequently reported in terms of a reduced hemoglobin (g/dL) or red blood cell count (per $mm^3$). Typical lower limits of normal values for these in healthy adult humans are 12-13 g/dL and about $4.1\times10^6$ per $mm^3$, respectively. Generally an adult human subject is said to have neutropenia when the neutrophil count falls below 1000 per $mm^3$. Additionally, an adult human is generally said to have agranulocytosis when the total granulocyte cell count falls below 500 cells/$mm^3$. Corresponding values for all these parameters are different for other species.

Hematopoeitic disorders such as anemia, thrombocytopenia, neutropenia and agranulocytosis are also frequently associated with clinical signs and symptoms in relation to their degree of severity. Anemia may be manifested as pallor, generalized fatigue or weakness, reduced exercise tolerance, shortness of breath with exertion, rapid heart rate, irregular heart rhythm, chest pain (angina), congestive heart failure, and headache. Thrombocytopenia is typically manifested in terms of spontaneous or uncontrolled bleeding, petechiae, and easy bruising. Neutropenia is associated with infections, including notably infections from endogenous microbial flora, and lack of inflammation.

Accordingly, the present invention contemplates ancillary combination therapies which employ both the E-selectin antagonist/mobilizer combination and an ancillary treatment that treats a hematopoeitic disorder as broadly described above. In some embodiments, the ancillary combination therapy will employ an E-selectin antagonist/mobilizer combination and a medicament selected from an anemia medicament, a thrombocytopenia medicament, an agranulocytosis medicament or a neutropenia medicament, illustrative examples of which include steroids, inducers of steroids, and immunomodulators.

The steroids include, but are not limited to, systemically administered corticosteroids including methylprednisolone, prednisolone and prednisone, cortisone, and hydrocortisone. Inducers of steroids include, but are not limited to adrenocorticotropic hormone (ACTH).

Corticosteroids inhibit cytokine production, adhesion protein activation, and inflammatory cell migration and activation. The side effects associated with systemic corticosteroids include, for instance, reversible abnormalities in glucose metabolism, increased appetite, fluid retention, weight gain, mood alteration, hypertension, peptic ulcer, and asceptic necrosis of bone. Some side effects associated with longer term use include adrenal axis suppression, growth suppression, dermal thinning, hypertension, diabetes mellitus, Cushing's syndrome, cataracts, muscle weakness, and in rare instances, impaired immune function. It is recommended that these types of compounds be used at their lowest effective dose.

Commonly used anemia drugs which are currently on the market or in development include recombinant human EPO (EPOGEN; PROCRIT), preparations of iron (ferrous and ferric, CHROMAGEN; FEOSOL; INFED; IROSPAN; NEPHRO-FER; NEPHRO-VITE; NIFEREX; NU-IRON; SLOW FE), vitamin B12, vitamin B6, folic acid (CHROMAGEN; FERRO-FOLIC; NEPHRO-FER; NIFEREX), ascorbic acid, certain metabolites of vitamin D (calcitriol and alphacalcidol; CALCIJEX; ROCALTROL), androgens, and anabolic steroids (ANADROL), carnitine. In a specific embodiment the anemia medicament is recombinant EPO.

Drugs in common usage or development for the treatment of thrombocytopenia include glucocorticoids (prednisolone; prednisone; methylprednisolone; SOLUMEDROL), recombinant TPO, recombinant MGDF, pegylated recombinant MGDF, and lisophylline. In a specific embodiment the thrombocytopenia medicament is recombinant TPO.

Drugs in common usage or development for the treatment of neutropenia include glucocorticoids (prednisolone; prednisone; methylprednisolone; SOLUMEDROL), immunoglobulin G (SANDOGLOBULIN, IVEEGAM, GAMMAR-P, GAMIMNE N, GAMMAGARD S/D), androgens, recombinant IFN-γ (ACTIMMUNE), and uteroferrin. Antibiotics are frequently administered in association with neutropenia medicaments to treat or reduce the risk of infection.

As noted above, the present invention encompasses co-administration of an E-selectin antagonist/mobilizer combination in concert with an additional agent. It will be understood that, in embodiments comprising administration of the E-selectin antagonist/mobilizer combination with other agents, the dosages of the actives in the combination may on their own comprise an effective amount and the additional agent(s) may further augment the therapeutic or prophylactic benefit to the patient. Alternatively, the E-selectin antagonist/mobilizer combination and the additional agent(s) may together comprise an effective amount for preventing or treating the immunocompromised condition or infection. It will also be understood that effective amounts may be defined in the context of particular treatment regimens, including, e.g., timing and number of administrations, modes of administrations, formulations, etc.

In other aspects, the present invention also contemplates administering a high dose of the medical treatment that induces the immunocompromised condition, without inducing side effects. Ordinarily, when medical treatments such as chemotherapy and radiotherapy are administered in a high dose, a variety of side effects can occur, including the induction of the immunocompromised condition and infection. As a result of these side effects, the medical treatment is not administered in such high doses. In accordance with the present invention, such high doses of medical treatment (e.g., a higher dose of chemotherapeutic agent or radiation) which ordinarily induce side effects can be administered without inducing the side effects as long as the subject also receives concurrent administration of an E-selectin antagonist and a mobilizer of hematopoietic stem cells or progenitor cells. The type and extent of the side effects ordinarily induced by the medical treatment will depend on the particular treatment used.

Suitably, the E-selectin antagonist/mobilizer combination, and optionally the ancillary treatment, are administered on a routine schedule. Alternatively, the ancillary treatment may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the im E-selectin antagonist on a daily basis, every two days, every three days, every four days, every five days, every six days, a weekly basis, a monthly basis or any set number of days or weeks therebetween, every two months, three months, four months, five months, six months, seven months, eight months, nine months, ten months, eleven months, twelve months, etc. Alternatively, the predetermined routine schedule may involve concurrent administration of the E-selectin antagonist and the mobilizer on a daily basis for the first week, followed by a monthly basis for several months, and then every three months after that. Any particular combination would be covered by the routine schedule as long as it is determined ahead of time that the appropriate schedule involves administration on a certain day.

Additionally, the present invention provides pharmaceutical compositions for treating or preventing an immunocompromised condition that results from a medical treatment as broadly described above. The pharmaceutical compositions include an E-selectin antagonist and a mobilizer of hematopoietic stem cell or progenitor cells, optionally formulated in a pharmaceutically acceptable carrier. The pharmaceutical composition may include an ancillary or additional medicament as broadly described above. In some embodiments, the E-selectin antagonist and the mobilizer will be present in the pharmaceutical composition in an effective amount for preventing or treating an immunocompromised condition (e.g., anemia, thrombocytopenia, or neutropenia). The effective amount for preventing or treating the immunocompromised condition is that amount which completely or partially prevents the development of, prevents the worsening of, or treats the established existence of, the immunocompromised condition. In some instances, the effective amount for preventing or treating immunocompromised condition completely or partially prevents or treats clinical symptoms of that condition.

In addition to clinical outcomes measured in terms of physiology, in vitro assays measuring erythrocyte, platelet, granulocyte and total white blood cell counts may be used in determining a therapeutically effective amount of a particular E-selectin antagonist. These methods are standard medical laboratory techniques that are well known in the art. In common practice such measurements may be made by automated cell counting devices designed for that purpose, or they may be performed manually. Manual counts may be more accurate than automated counts when cell counts are particularly low.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. Depending on the specific conditions being treated, the formulations may be administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the active agents or drugs of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The drugs can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more drugs as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments may be added to the tablets or dragee coatings, for identification or to characterize different combinations of active compound doses.

Pharmaceutical which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the drugs of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes or microspheres.

The drugs of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (e.g., the concentration of an active agent, which achieves a half-maximal inhibition in activity of an E-selectin polypeptide). Such information can be used to more accurately determine useful doses in humans.

Toxicity and therapeutic efficacy of such drugs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See for example Fingl et al., 1975, in "The Pharmacological Basis of Therapeutics", Ch. 1 p1).

Alternately, one may administer the compound in a local rather than systemic manner, for example, via injection of the compound directly into a tissue, which is preferably subcutaneous or omental tissue, often in a depot or sustained release formulation.

Furthermore, one may administer the drug in a targeted drug delivery system, for example, in a liposome coated with tissue-specific antibody. The liposomes will be targeted to and taken up selectively by the tissue.

In cases of local administration or selective uptake, the effective local concentration of the agent may not be related to plasma concentration.

In order that the invention may be readily understood and put into practical effect, particular preferred embodiments will now be described by way of the following non-limiting examples.

EXAMPLES

Example 1

Hematopoietic Stem Cell Turnover is Delayed 2.7-Fold In Vivo in the Bone Marrow of Mice Lacking the E-Selectin Gene Using C57BL/6 mice knocked-out for either or both the P- or E-selectin genes, it was shown that deletion of E-selectin, but not P-selectin, delays hematopoietic stem cell turn-over in the bone marrow in vivo. Mice were fed with BrdU in their drinking water for up to 14 days and sacrificed on days 3, 5, 7 and 14 to sort LSK34-hematopoietic stem cells. Following antibody staining with an anti-BrdU monoclonal antibody, 50% of LSK34-cells from the bone marrow of wild-type (WT) and P-sel−/− mice incorporated BrdU in 3.6 days whereas 50% of LSK34-cells from E-sel−/− and P/E-selectin double KO mice incorporated BrdU in 9.5 days (see FIG. 1). Thus, the cycling time of hematopoietic stem cell is 2.7 fold slower in the absence of E-selectin.

Figure 5:
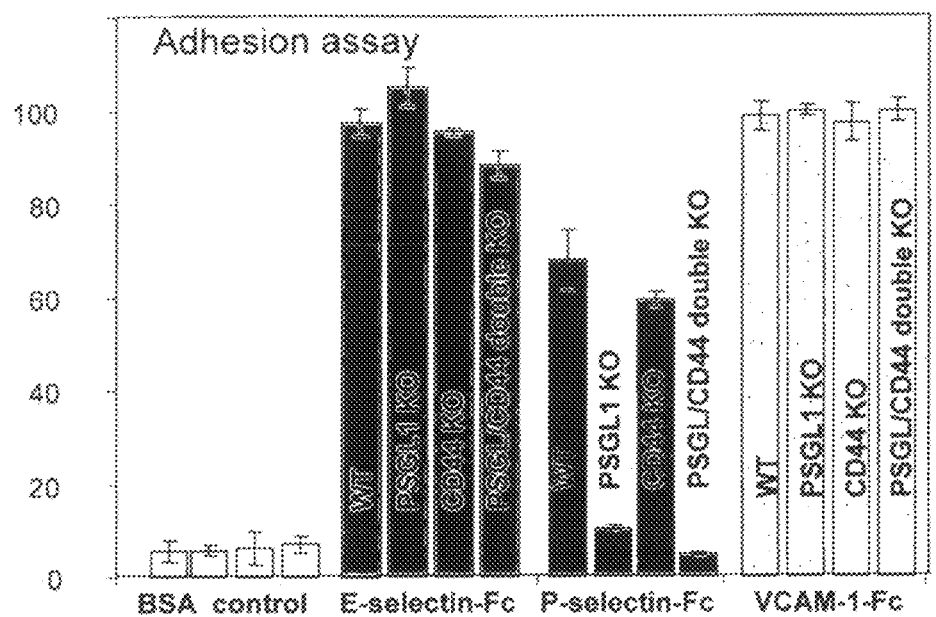
FIG. 5 is a graphical representation showing that deletion of the PSGL1 and CD44 genes has no effect on adhesion of hematopoietic progenitor cells to recombinant mouse E-selectin immobilised to plastic. Recombinant muE-selectin-IgG1Fc, muP-selectin-IgG1Fc and muVCAM1-IgG1Fc were adsorbed to the bottom of 96-well polystyrene tissue culture plates overnight, then the wells thoroughly washed and blocked before the addition of 30,000 calcein-labelled Lineage-negative CD117-positive cells from sorted from the bone marrow of wild-type, PSGL-1−/−, CD44−/−, or CD44−/−/PSGL−/− double KO mice. Data are expressed as a percentage of adherent cells and a means+/−standard deviation of triplicates.
Figure 6:
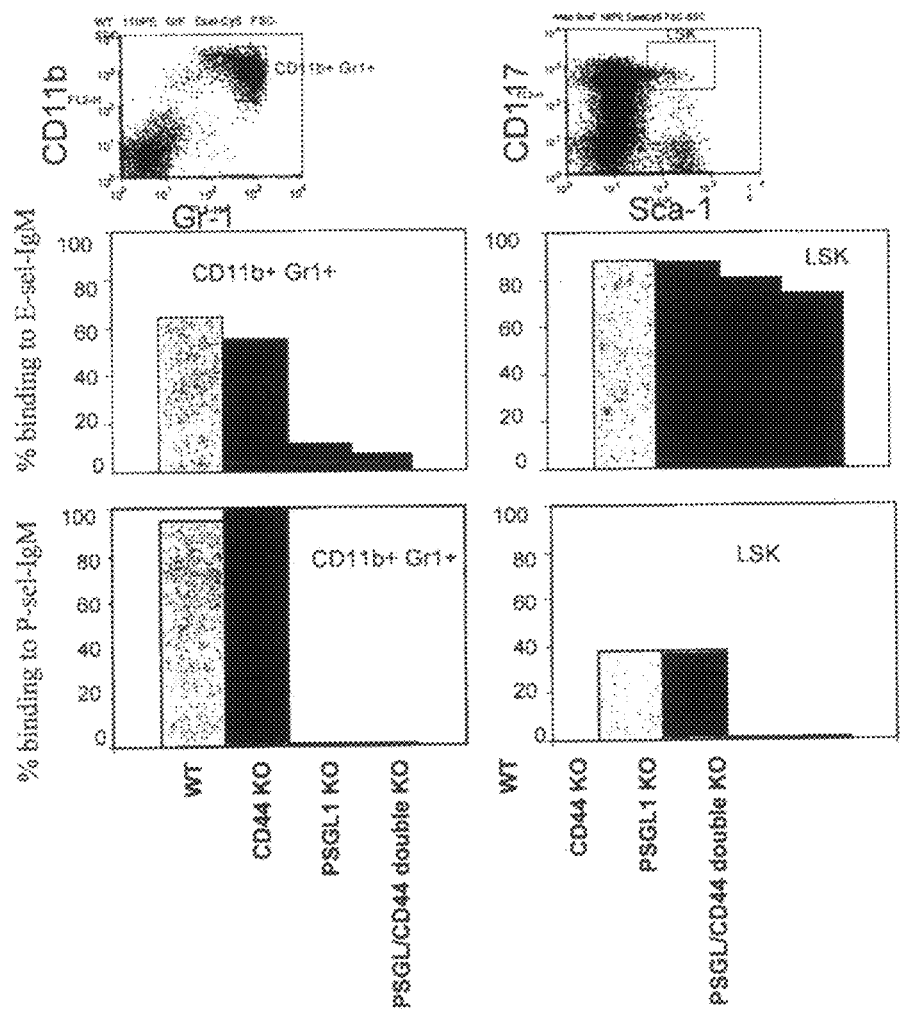
FIG. 6 is a graphical representation showing that deletion of CD44 and PSGL1 genes does not perturb binding of soluble recombinant E-selectin-IgMFc fusion protein to the surface of LSK hematopoietic stem cells. Top panels show the gating strategy to measure selectin-IgM binding at the surface of bone marrow CD11b-positive Gr1-positive granulocytes and lineage-negative Sca1-positive CD117-positive (LSK) hematopoietic stem cells. The bottom panels show the proportion of these binding either the recombinant E-selectin-IgMFc or P-selectin-IgMFc fusion proteins.

To determine whether this effect was mediated by the two previously identified E-selectin receptors PSGL-1 and CD44, BrdU incorporation experiments were repeated with mice knocked-out for both the PSGL-1 and CD44 genes. LSK34-cell turnover in these mice was identical to that of wild-type suggesting that the effect is mediated by distinct unknown receptor(s). FIGS. 5 and 6 Confirm that BM HSPC can adhere to E-selectin independent of PSGL-1 and CD44.

Example 2

In the Absence of E-Selectin, Bone Marrow Hematopoietic Stem Cells are Metabolically Less Active To support findings on hematopoietic stem cell turnover with BrdU, lineage-negative Sca1-positive CD117-positive (LSK) hematopoietic stem cells were isolated from the bone marrow and stained with Rhodamine-123, a viable dye that binds to mitochondrial membranes and is retained by metabolically active respirating cells.

Figure 2:
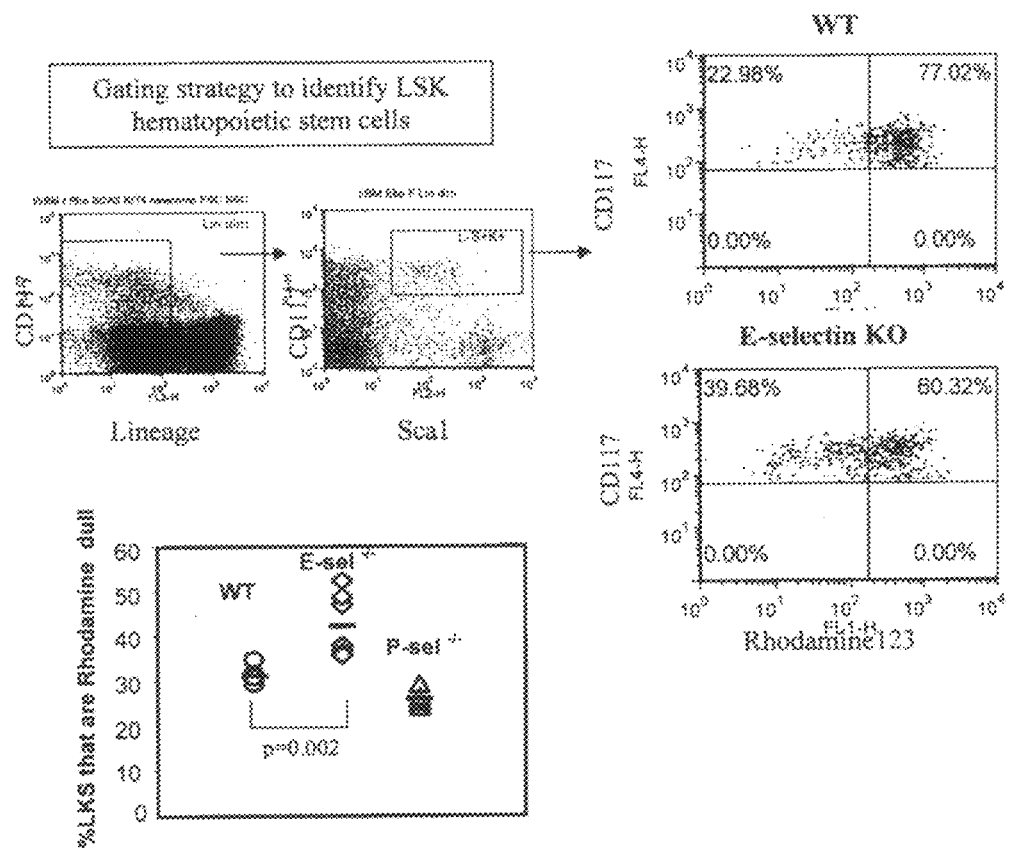
FIG. 2 is a graphical representation showing that LSK hematopoietic stem cells are less metabolically active in E-selectin KO mice than wild-type mice. Upper panels show the gating strategy to measure rhodamine123 incorporation into LSK hematopoietic stem cells. The bottom panel shows the percentage of bone marrow LSK hematopoietic stem cells that incorporate low levels of Rhodamine123.

A higher proportion of LKS cells from E-selectin−/− mice were rhodamine dull (43±3%) compared to LKS cells from wild-type mice (30-12%; p=0.002) confirming that a greater proportion of hematopoietic stem cells from E-selectin knock-out mice are quiescent (FIG. 2).

To confirm that metabolically active Rhodamine123 dull cells cycle and incorporate BrdU less rapidly, Rhodamine bright and Rhodamine dull LKS cells were sorted from the same bone marrows as shown in FIG. 2. Rhodamine dull LKS cells incorporated BrdU 7 times less than Rhodamine bright LSK cells after 2 days of BrdU feeding to the mice, showing that less metabolically active Rhodamine dull stem cells are 7 times less likely to have cycled (and be BrdU-positive) during the two day period of BrdU feeding.

Rho bright LKS+→35% BrdU+ (2 days)
Rho dull LKS+→5% BrdU+ (2 days)

Taken together, these results confirm that in the absence of the E-selectin gene, hematopoietic stem cells residing in the bone marrow are less metabolically active and divide slower than in wild-type mice.

Example 3

Figure 3:
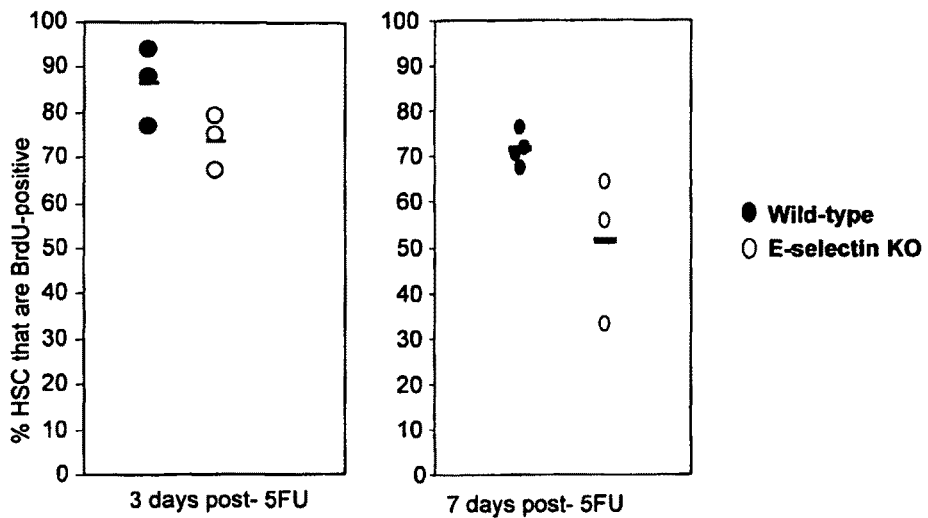
FIG. 3 is a graphical representation showing lower HSC turn-over in bone marrow of E-selectin KO mice following chemotherapy with the cytotoxic drug 5FU. These data represent the percentage of cycling lineage-negative Sca1-positive CD41-negative CD48-negative CD150-positive long-term reconstituting hematopoietic stem cells that incorporated BrdU over a period of 17 hours of continuous administration of BrdU prior sacrifice at days 3 (left panel) and day 7 (right panel) following administration of a single dose of 150 mg/kg of 5FU. Each dot represents result from an individual mouse. The horizontal bar is the average of the group.

Hematopoietic Stem Cell Turnover is Lower in E-Selectin KO Mice Following Cytotoxic Insult with 5-Fluorouracil To determine the effect of E-selectin gene deletion on hematopoietic stem cell recovery following cytotoxic stress, E-selectin KO and wild-type mice were injected with a single dose of 5-fluorouracil (5FU 150 mg/kg). As CD117 is strongly down-regulated in the bone marrow of 5FU-treated mice, the proportion of lineage-negative Sca1-positive CD41-negative CD48-negative CD150-positive long-term reconstituting hematopoietic stem cells[6] that incorporate BrdU was measured. For this propose, mice were sacrificed prior to and at day 3 or day 7 following 5-FU injection and BrdU was given continuously through drinking water in the last 17 hours before sacrificed. BrdU incorporation remained significantly lower in hematopoietic stem cells from E-selectin knock-out mice on days 3 and 7 post-5FU suggesting that the observed decreased HSC turn-over in the absence of E-selectin may protects them from the cytotoxic effect of 5FU (FIG. 3).

Figure 4:
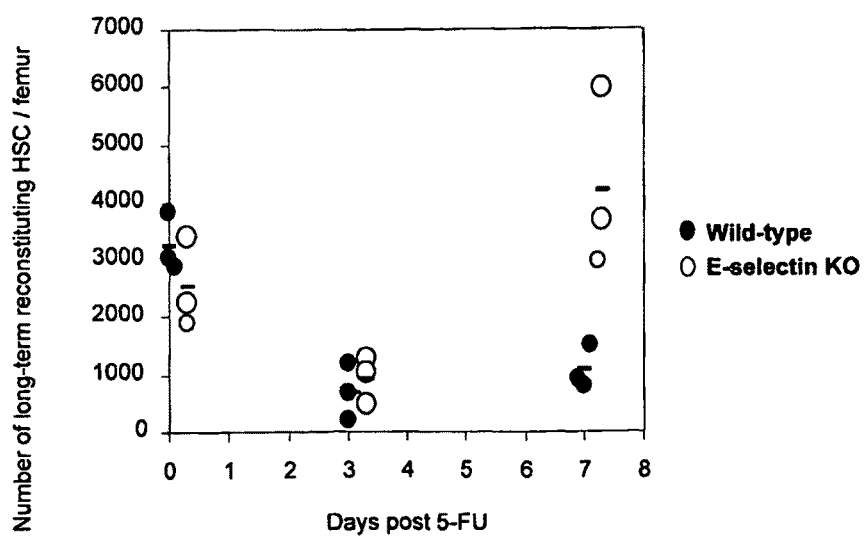
FIG. 4 is a graphical representation showing higher number of long-term reconstituting hematopoietic stem cells in E-selectin KO bone marrow following chemotherapy with the cytotoxic drug 5-FU. These data represent the total number of lineage-negative Sca1-positive CD41-negative CD48-negative CD150-positive long-term reconstituting hematopoietic stem cells per femur at the indicated time-points following administration of a single dose of 150 mg/kg of 5FU. Each dot represents result from an individual mouse. The horizontal bar is the average of the group.

The recovery of long-term reconstituting hematopoietic stem cells was also enhanced in E-selectin−/− mice at day 7 post-5FU with a 5-fold increase in HSC numbers per femur compared to WT mice (FIG. 4).

The fact that the proliferation of hematopoietic stem cells was lower with increased absolute number of stem cells per femur at day 7 following chemotherapy with 5-FU shows that hematopoietic stem cells were more resistant to the cytotoxic effect of 5FU in E-selectin knock-out mice. Thus deletion of the E-selectin results in enhanced resistance of hematopoietic stem cells to the cytotoxic effect of chemotherapy.

Example 4

The Effect of E-Selectin on the Turn-Over of Hematopoietic Stem Cells is not Mediated by the Two Previously Described E-Selectin Ligands P-Selectin Glycoprotein Ligand-1 (PSGL-1 or CD162) and CD44

BrdU incorporation data from FIG. 1 show that LSK34-hematopoietic stem cells isolated from the bone marrow of mice lacking both the PSGL-1 and CD44 genes incorporate BrdU and cycle at the same rate as hematopoietic stem cells isolated from wild-type mice. Thus, this suggests that the delayed cell cycling observed in hematopoietic cells from E-selectin KO mice is not mediated by the two previously described E-selectin receptors PSGL-1 and CD44[10].

To confirm this further, the inventors measured interaction of hematopoietic stem cells isolated from mice lacking both PSGL-1 and CD44 with recombinant E-selectin. In adhesion assays in 96-well polystyrene plates coated with recombinant proteins made of the entire extracellular domain of mouse E-selectin, P-selectin or VCAM-1/CD106 fused to the Fc fragment of human IgG1 (muEsel-IgG1Fc, muPsel-IgG1Fc, or muVCAM1-IgG1Fc), deletion of the PSGL1 gene completely abrogated adhesion of bone marrow linage-negative CD117-positive hematopoietic progenitor cells to P-selectin, demonstrating that PSGL1 is the sole P-selectin receptor on bone marrow hematopoietic progenitor cells. In sharp contrast, the deletion of either or both the PSGL1 and CD44 genes, did not alter adhesion of bone marrow hematopoietic progenitor cells to E-selectin or to VCAM-1, an unrelated cell adhesion molecule whose cellular receptors are $\alpha 4$ integrins/CD49d (FIG. 5).

In a second assay, binding of recombinant E-selectin and P-selectin was directly measured in solution by flow cytometry. For this purpose, recombinant human P-selectin or E-selectin extracellular domains fused with the Fc portion of human IgM were used as selectins required prior clustering to bind to their cellular receptors. As IgM are decameric proteins, each fusion recombinant protein is a decamer or either P-selectin or E-selectin. The clustering resulting from decamerization of selectin enables them to directly interact in solution with their cellular receptors. The inventors therefore measured the binding of recombinant selectin-IgM Fc fusion proteins to bone marrow cells isolated from wild-type, PSGL1−/−, CD44−/− or PSGL1−/− CD44−/− double KO mice. Detection by flow cytometry was performed by pre-complexing the selectin-IgMFc fusion proteins with a Cy5-conjubated donkey anti-human IgM antibody. FIG. 6 shows that while deletion of both PSGL1 and CD44 genes markedly reduced binding of recombinant E-selectin-IgMFc to bone marrow granulocytes, the deletion of these two genes did not decrease the binding of recombinant E-selectin-IgMFc to bone marrow LSK hematopoietic stem cells. Thus these experiments confirm that PSGL1 and CD44 are necessary and sufficient for E-selectin binding to mature granulocytes, hematopoietic stem cells can bind and adhere to E-selectin via alternative receptors which are not encoded by the PSGL1 and C44 genes.

Example 5

Enhanced Mobilization of Hematopoietic Stem and Progenitors Cells in Response to G-CSF in Mice Lacking the E-Selectin Gene Mobilization is the forced movement of HSC from the bone marrow into the blood where they can be easily collected. Mobilized blood is now the preferred source of HSC for transplantation having surpassed the more traditional bone marrow aspirates.

Currently, the main use of mobilized HSC is to transplant into patients who have undergone repeated rounds of chemotherapy to treat cancers (a side-effect of chemotherapy is bone marrow/HSC damage), or to treat some genetic diseases of the hematopoietic and immune system in order to reconstitute normal disease-free hematopoiesis in these patients.

The main limitation to the success of HSC transplantation however, is obtaining sufficient numbers of HSC from a donor to ensure rapid engraftment and hematopoietic/immune reconstitution. This is particularly true in the case of autologous transplantation from patients who have undergone many rounds of chemotherapy. Up to 50% of patients who have undergone repeated rounds of high dose chemotherapy/radio therapy are unable to mobilize sufficient HSC into the blood for a successful transplant (in human patients, usually >2×10$^6$ CD34$^+$ phenotypic cells/kg body weight). In addition, up to 5% of normal healthy allogeneic donors fail to mobilise sufficient numbers of HSC in response to G-CSF in order to ensure rapid and safe haematopoietic reconstitution of transplant recipient.

Figure 7:
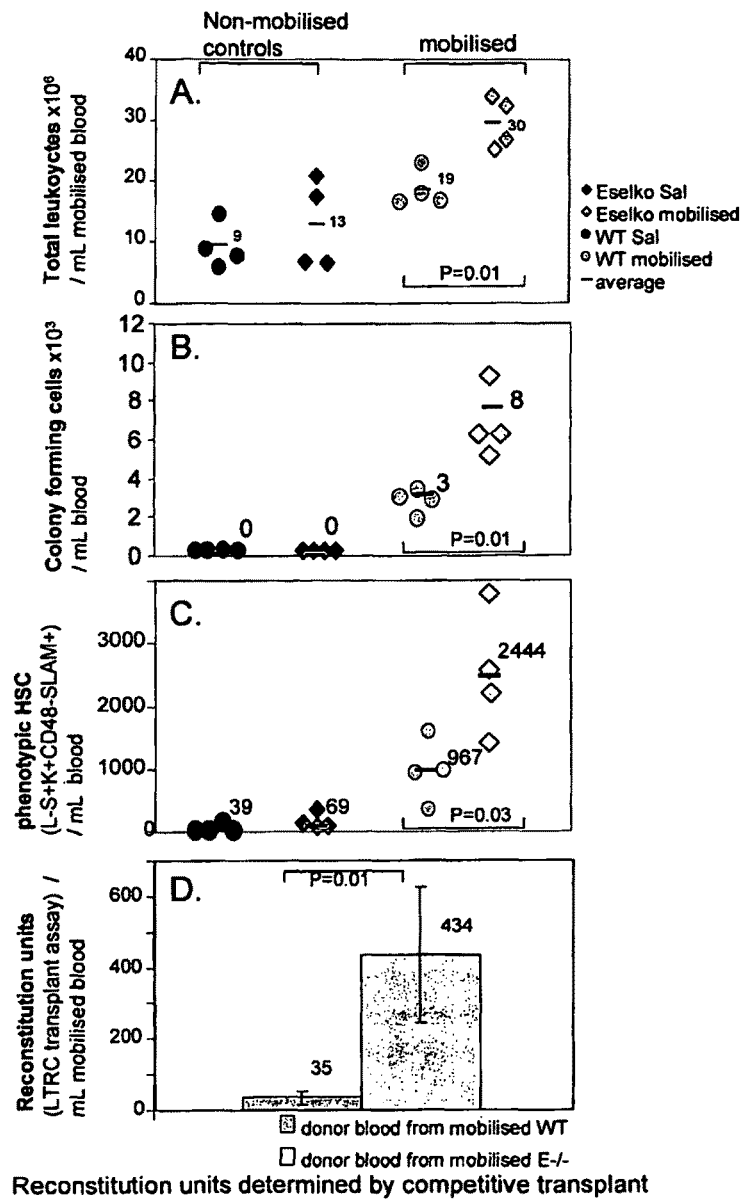
FIG. 7 is a graphical representation showing increased mobilization of CFC, phenotypic HSC and functional HSC in E-selectin KO mice in response to G-CSF. Groups of mice, either wild-type C57BL/6 or E-selectin knockout on a C57BL/6 background were mobilized according to the protocol described in the Materials and Methods section below (administration of a total 1 mg/kg pegylated recombinant human G-CSF) and blood collected 3 days later for analysis of mobilized HSC content. A second cohort of mice received saline injections and are designated as non-mobilized controls. Blood was analyzed for total leukocyte count (7A), colony forming cells (7B), phenotypic HSC (7C) and a portion injected into lethally irradiated recipient mice to determine the number of repopulating units (RU) in a long-term competitive reconstitution assay (7D). Significant levels are indicated ($p<0.05$) and were calculated using the non-parametric Mann-Whitney test.
Figure 8:
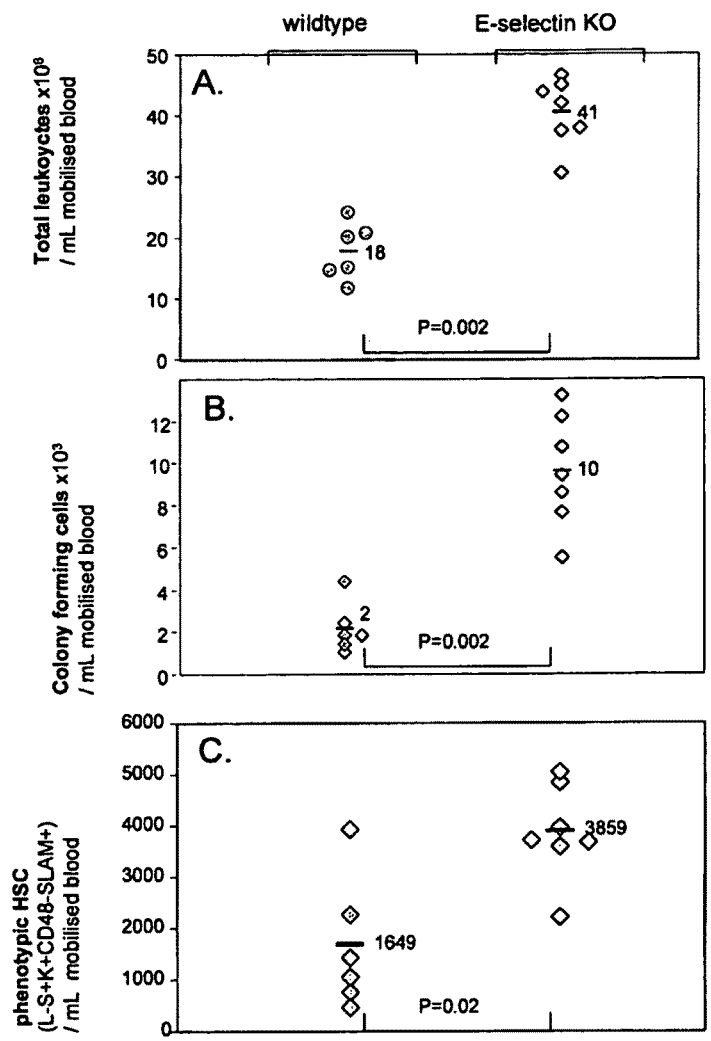
FIG. 8 is a graphical representation showing increased mobilization of CFC and phenotypic HSC in E-selectin KO mice which underwent 8 cycles of chemotherapy with cyclophosphamide prior to mobilization with G-CSF. Wild-type and E-selectin KO mice were first administered fortnightly rounds of the chemotherapeutic agent cyclophosphamide at 200 mg/kg for 8 rounds, then allowed to rest for 6 weeks prior to administration of G-CSF (total 1 mg/kg as above) and blood collected 3 days when HSC are mobilised. Blood was analyzed for total leukocyte count (8A), Colony forming cells (8B) and phenotypic HSC (8C).

In accordance with the present invention, the results presented in FIGS. 7 and 8 show that mobilization of HSC can be enhanced significantly following deletion of the cell adhesion molecule E-selectin (CD62E).

In particular, FIG. 7 shows that in steady-state conditions, saline injected wild-type and E-selectin KO mice have equivalent numbers of blood leukocytes, no detectable number of CFC and very low levels of phenotypic Lin-Sca-1+CD117+CD48-CD50$^+$ HSC in the peripheral blood. After a 3-day course of pegylated G-CSF administration, mobilization is higher in E-selectin KO than in wild-type mice with a 2.5-fold high number of CFC (FIG. 7B), 2.5-fold high number of phenotypic HSC (FIG. 7 C) and a 12-fold higher number of functional long-term reconstituting HSC per mL of mobilized blood.

In order to mimic the clinical setting of autologous transplantation where cancer patients are heavily treated with chemotherapy prior to mobilization of their own HSC and transplantation, two cohorts of wild-type and E-selectin KO mice were injected fortnightly with a single dose of cyclophosphamide for 8 rounds. After the 8$^{th}$ round, mice rested 6 weeks prior to mobilization following injection of pegylated G-CSF. FIG. 8 shows that E-selectin KO mice pre-treated with chemotherapy mobilized 5-fold more CFC and 2.5-fold more phenotypic HSC per mL of peripheral blood, as compared to wild-type mice pre-treated with chemotherapy.

Materials and Methods

Incorporation of 6-Bromodeoxyurine (BrdU) to Measure Hematopoietic Stem Cell Turnover In Vivo The aim of this method is to measure the proportion of hematopoietic stem cells that incorporate the nucleotide analog BrdU into their genomic DNA during a given period of time in vivo. Since BrdU can only integrate into genomic DNA during the S phase of the cell cycle, the proportion of cells that have incorporated BrdU is equal to the proportion of cells that have divided or are dividing during the period of animal feeding with BrdU[5].

Adult mice (10-14 week-old) with homologous deletion of the E-selectin gene (Sele), the P-selectin gene (Selp), both the E-selectin and P-selectin genes, or both the CD162/PSGL1 (Selplg) and CD44 (Cd44) genes were given 1 mg/mL BrdU solubilised in their drinking water for a continuous period of up to 14 days.

At various time-points, mice were sacrificed and femurs, tibias and iliac crest harvested. One cleaned, bones were crushed with a mortar and pestle in phosphate-buffered saline containing 2% new-born calf serum to extract bone marrow cells. Mononucleated bone marrow cells were isolated by centrifugation at 500×g on a density gradient made with 62.5% Percoll.

Cells expressing c-KIT/CD117 were next enriched by magnetic cell sorting (MACS) using mouse CD117 magnetic microbeads (Miltenyi Biotec). For this purpose, mononucleated cells at the Percoll interface were washed in phosphate-buffered saline containing 0.5% bovine serum albumin and 2 mM ethylene diamine tetraacetate (MACS washing buffer), resuspended at 10$^8$ cells/mL and subsequently incubated with 1.54 mouse CD117 microbeads per 10$^7$ cells. Cells were incubated for 15 minutes on ice with magnetic beads, washed once in MACS washing buffer, pelleted at 440×g, resuspended at $10^8$ cells/mL in MACS washing buffer. Cells expressing CD117 were then enriched by separation on an autoMACS Separator (Miltenyi Biotec) using the cell depletion program.

Hematopoietic stem cells were further isolated from this CD117 MACS-enriched population by fluorescence-activated cell sorting (FACS) using the following panel of antibodies: a) biotinylated antibodies against lineage-specific antigens CD3, CD5, B220/CD45R, CD11b, Gr-1/Ly-6G, Ter119 together with streptavidin conjugated to PercP-Cy5.5; b) fluorescein isothiocyanate (FITC) conjugated anti-CD34; c) phycoerythrin (PE) conjugated anti-Sca-1/Ly-6A/E; d) allophycocyanin (APC) conjugated anti-CD117 antibodies. Hematopoietic stem cells with the phenotype Lineage-negative, Sca-1-positive, CD117-positive and CD34-negative (LSK34-), were sorted on a FACS Aria cell sorter (BD Biosciences), collected in phosphate-buffered saline containing 2% newborn calf serum and cytospun on positively charged glass slides. Once cytospun on glass slides, LSK34-cells were air dried and fixed with the fixative provided in the BD Pharmingen BrdU detection kit (catalog#551321). Staining with a monoclonal antibody specific for BrdU was then performed exactly following the kit instructions. Following counterstaining with dilute hematoxylin and mounting with Aquamount, the proportion of cells staining for BrdU was manually counted using a microscope.

In additional experiments, BrdU incorporation was measured in a purer population of hematopoietic stem cells. This population has the phenotype Lineage-negative, Sca1-positive, CD117-positive, CD41-negative, CD48-negative, CD150-positive. This very rare population (0.05% of the bone marrow) has been described to be homogenous with high reconstituting activity. Specifically, 50% of lethally irradiated mice transplanted with a single cell exhibiting this phenotype can reconstitute a full hematopoietic/immune system from this single cell[6]. The combination of antibodies to sort these cells is as follows: a) biotinylated antibodies against lineage-specific antigens CD3, CD5, B220/CD45R, CD11b, Gr-1/Ly-6G, CD41, Ter119 together with streptavidin conjugated to PercP-Cy5.5; b) fluorescein isothiocyanate (FITC) conjugated anti-CD48; c) phycoerythrin (PE) conjugated anti-CD150; d) PECy7 conjugated anti-Sca-1/Ly-6A/E; f) allophycocyanin (APC) conjugated anti-CD117 antibodies Determination of Hematopoietic Stem Cell Metabolic Activity by Flow Cytometry Using Rhodamine123 Fluorescent Dye Rhodamine-123 is a vital fluorescent dye that incorporates preferentially in mitochondria. It has been previously described that most quiescent hematopoietic stem cells with highest reconstituting potential following transplant incorporate low levels of rhodamine-123 whereas metabolically active stem cells incorporate high levels of rhodamine 123[5,7].

For this purpose, bone marrow cells extracted as above were resuspended at $10^6$/mL in PBS with 2% fetal calf serum and incubated with Rhodamine123 (0.1 µg/mL) at 37° C. for 20 min then washed in PBS with 2% fetal calf serum and incubated at $10^6$/mL in PBS+2% serum for another 15 min at 37° C. to efflux excess dye incorporated in cells. Following Rho123 efflux, cells were kept on ice and subsequently stained with biotinylated lineage antibodies (CD3, CD5, B220, Gr-1, F4/80, Ter119), CD117-APC, Sca-1-PE then washed and incubated with strepatvidin-PerCPCy5.

Lineage-negative, CD117-positive, Sca1-positive cells were analysed by flow cytometry for Rhodamine-123 fluorescence on a BD Biosciences FACS Calibur flow cytometer Measurement of HSC Cycling and Number In Vivo Following Cytotoxic Insult with the Chemotherapeutic Drug 5-Fluorouracil (5-FU)

Adult mice (10-14 week-old) with homologous deletion of the E-selectin gene were administered intravenously a single dose of 5-FU at 150 mg/kg. At days 2 and 6 following 5-FU, mice were injected intraperitoneally BrdU 100 mg/kg followed by a continuous dose of 1 mg/mL in their drinking water at a concentration of 1 mg/mL. 18 hours following the injection of BrdU. Mice were sacrificed, their bone marrow cells collected as described above and stained with the following combination of antibodies: a) biotinylated antibodies against lineage-specific antigens CD3, CD5, B220/CD45R, CD11b, Gr-1/Ly-6C/G, CD41, Ter119 together with streptavidin conjugated to PercP-Cy5.5; b) fluorescein isothiocyanate (FITC) conjugated anti-CD48; c) phycoerythrin (PE) conjugated anti-CD150; d) PECy7 conjugated anti-Sca-1/Ly-6A/E; f) allophycocyanin (APC) conjugated anti-CD117 antibodies. True hematopoietic stem cells with the phenotype Lineage-negative, Sca1-positive, CD117-positive, CD41-negative, CD48-negative, CD150-positive were counted and sorted as described above. Sorted cells were cytospun on glass slides and stained with anti-BrdU antibodies as described above.

Cell Adhesion Assay of Hematopoietic Progenitor Cells on Immobilised Recombinant Mouse E-Selectin and P-Selectin Fusion Proteins 96-well polystyrene cell culture plates were coated overnight at 4°C with 50 µL per well of phosphate buffered saline containing 3 µg/ml of recombinant proteins made of the entire extracellular domain of mouse E-selectin, P-selectin or VCAM-1/CD106 fused to the Fc fragment of human IgG1 (muEsel-IgG1Fc, muPsel-IgG1Fc, or muVCAM1-IgG1Fc respectively, from R&D Systems)) as previously described 8. Prior to the experiment, plates were flicked to remove excess coating solution and filled with Hepes buffered saline supplemented with 2% bovine serum albumin to block non-specific adhesion to plastic surfaces. Following 1 hour incubation at 37° C., coated wells were washes twice with cell adhesion buffer (Iscove's modified Dulbecco medium supplemented with 0.2% bovine serum albumin and 1 mM CaCl2).

Bone marrow cells from CD44 KO, PSGL1 KO and CD44-PSGL1 double KO mice were stained with FITC-conjugated biotinylated rat monoclonal antibodies specific for CD3, CD5, B220/CD45R, CD11b, Gr1 and Ter119 lineage-specific antigens and PE-conjugated anti-CD117 antibody. Lineage-negative CD117-positive hematopoietic progenitor cells were then sorted by fluorescence activated cell sorting on an Aria cell sorter (BD Biosciences).

Sorted Lineage-negative CD117-positive hematopoietic progenitor cells when then washed and resuspended in cell adhesion buffer and labelled with the intracellular fluorescent dye calcein-AM (Molecular Probes) for 40 minutes at 37° C. 8. Following labelling with calcein-AM, cells were washed in cell adhesion buffer and resuspended at $10^5$ cells/mL. 100 µL (104 cells) were deposited in each well coated with muEsel-IgG1Fc, muPsel-IgG1Fc, muVCAM1-IgG1Fc, or serum albumin alone, centrifuged at 200×g for 5 minutes to sediments cells at the bottom of coated wells and further incubated for 40 minutes on ice. Following this incubations, non-adherent cells were removed by 4 gentle washes with cell adhesion buffer. The fluorescence contained in the remaining adherent cells was measured on a Fluorostar plate fluorometer following exciting at 488 nm using a 530 nm filter.

Measurement of the Binding of Recombinant E-Selectin and P-Selectin on Haematopoietic Stem Cells in Suspension Recombinant human E-selectin and P-selectin extracellular domains fused with the Fc fragment of human IgM (selectin-IgMFc) were produced as supernatants following transfection of COS7 cell line with pCDM8 plasmids containing the corresponding cDNA[9]. Following transfection, COS7 medium was replaced by serum-free X-VIVO10 medium and conditioned for three days post transfection. Saturating doses of selectin-containing supernatants were determined by flow cytometry using the human myeloid cell line KG1a.

Prior to the experiment, recombinant selectin-IgMFc fusion proteins were complexed with Cy5-conjugated donkey IgG F(ab)'2 fragments anti-human IgM. For this purpose, serum-free supernatants were incubated with an equal volume of cell adhesion buffer (Iscove's modified Dulbecco medium supplemented with 0.2% bovine serum albumin and 1 mM $CaCl_2$) containing a 1/50 dilution of Cy5-conjugated donkey IgG F(ab)'2 fragments anti-human IgM (Jackson ImmunoResearch) for 2 hours at 4° C.

Bone marrow cells from CD44 KO, PSGL1 KO and CD44-PSGL1 double KO mice were depleted of lineage-positive cells on an autoMACS Separator using biotinylated rat monoclonal antibodies specific for CD3, CD5, B220/CD45R, CD11b, Gr1 and Ter119 lineage-specific antigens and streptavidin-coated magnetic immunobeads (Miltenyi Biotec). Following depletion, lineage-negative bone marrow cells were stained on ice for 40 minutes with FITC-conjugated anti-Sca1/Ly6A-E and PE-conjugated anti-CD117 rat monoclonal antibodies. Following washing with cell adhesion buffer described above, $10^6$ labelled lineage-depleted bone marrow cells were resuspended in a volume of 25 µL of cell adhesion buffer. Twenty-five µL of selectin-IgMFc pre-complexed with Cy5-conjugated donkey anti-human IgM was then added to the cells and further incubated for 40 minutes at 4° C. Negative controls were performed by adding the calcium chelator ethylene diamine tetraacetic acid (5 mM) in the cell adhesion buffer as selectin-mediated interactions are strictly calcium-dependant. Binding of selectin-IgMFc fusion proteins was measured by flow cytometry on a FACS Calibur flow cytometer (BD Biosciences).

Mobilization of HSC with Recombinant Human G-CSF

Mobilization was induced in wild-type C57BL/6 mice and in C57BL/6 mice carrying homologous deletion of the E-selectin gene (E-selectin KO mice), using recombinant human G-CSF following a mobilization dosing and protocol similar to that used for human patients.

Adult mice (10- to 14-week old males) were administered recombinant human pegylated G-CSF (granulocyte colony stimulating factor) subcutaneously. Two doses were given 36 hours apart, each at 0.5 mg/kg. The G-CSF used was Neulasta, from Amgen. Neulasta was diluted to 0.1 mg/mL in sterile saline for injection and 100 µL used per injection into 20 g mice. In some experiments, a cohort of 'control' mice received saline injections alone.

Blood containing the mobilized HSC, was collected 3 days following the initial G-CSF injection using heparin as anti-coagulant (13 units of sodium heparin/mL blood). Four different assays were performed on the blood to determine the extent of HSC mobilization. Some of these assays are surrogate measures of mobilization that are commonly used in the clinical setting; that is they measure associated changes, not HSC content directly. These are total blood leukocyte counts and numbers colony forming cells (CFC) in the blood. The third assay based on phenotypic analysis (expression of a panel of surface markers which define long-term reconstituting HSC), while directly measuring HSC, also detect some progenitor cell populations. Phenotypic enumeration is commonly used to determine HSC mobilization in human patients (a different array of cell-surface markers are used in mice). However the only assay that will truly determine the level of HSC mobilization into the blood remains transplantation of mobilized blood into lethally irradiated recipients, and following reconstitution, analyse whether these transplanted blood cells have indeed contributed to the bone marrow and blood reconstitution in the lethally irradiated host.

These four assays were performed on the mobilized blood collected from these mice as follows:

A) Blood leukocyte counts were measured on a Sysmex KX21 automated haematology analyser (Roche).

B) Colony forming cell assay. A portion of the blood was subject to red cell lysis (blood was incubated in 150 mM $NH_4CL$, 10 mM $NaCO_2$, 1 mM EDTA for 10 minutes on ice, then red cell remnants removed by washing twice in PBS with 2% newborn calf serum). Remaining nucleated blood leukocytes (exactly 50,000) were then added to 1 mL colony assay counting media in duplicate, and incubated at 37° C. in 5% $CO_2$ to allow cell division into clonogenic colonies. Following 7 days incubation, the number of leukocyte colonies were enumerated manually using an inverted microscope. Each colony (defined as >50 cells) is derived from a single haematopoietic progenitor cell. The number of colony forming cells (CFC) per mL of blood can then been calculated. The colony assay counting media contains: Iscove's modified Dulbeccos medium (1×IMDM), 35% foetal calf serum, Penicillin 125 µg/mL, Genamycin 16 µg/mL, L-glutamine 2 mM, recombinant mouse Interleukin 3 at 10 ng/mL, recombinant mouse Interleukin 6 at 50 ng/mL, recombinant mouse Stem cell factor at 50 ng/mL.

C. Phenotypic HSC analysis. A portion of lysed blood (red blood cell lysis method above) was stained using the following panel of directly conjugated monoclonal antibodies at a concentration of 2.5 µg/$10^8$ cells/mL; a) biotinylated antibodies against lineage-specific antigens CD3, CD5, B220/CD45R, CD11b, Gr-1 or Ly-6C/G, CD41, Ter119 together with streptavidin conjugated to Pacific blue; b) fluorescein isothiocyanate (FITC) conjugated anti-CD48; c) phycoerythrin (PE) conjugated anti-SLAM/CD150; d) allophycocyanin (APC) conjugated anti-CD117/KIT and e) PECy7 conjugated anti-Sca-1. HSC are cells with the phenotype Lineage-negative, Sca-1-positive, CD117-positive, CD48-negative and CD150-positive[11].

D. Competitive Long-term reconstitution assay following transplant of mobilized blood. These experiments use two strains of mice congenic for CD45 isoforms: The C57BL/6 strain which expresses CD45.2 isoform on all hematopoietic cells, and the B6.SJL strain which expresses the CD45.1 isoform on all hematopoietic cells. This enables donor test cells to be distinguished from host cells and competitive cells based on the expression of either CD45.1 or CD45.2 antigens. Recipient mice for the transplant (8-week old congenic B6.SJL females CD45.1$^+$, 6 mice/group) received a lethal dose of irradiation on the day before the experiment (total 11.0 Gy given as two doses of 5.5 Gy; 4 hours apart—to minimize gut toxicity). Next day, each irradiated mouse was transplanted with 25 µL of whole heparinized mobilized blood (pooled from either wild-type or E-selectin knockout donors, both are in the C57BL/6 background with CD45.2$^+$ phenotype), mixed together with 200,000 competing healthy bone marrow cells from the congenic B6.SJL strain (CD45.1$^+$). Cells are injected via the retro-orbital route, engraft and reconstitute the lethally-irradiated bone marrow and promote survival of the recipient mice. At 16 weeks post transplant, blood is collected from the recipient mice. Blood leukocytes will either be CD45.2$^+$ (hence derived from the mobilized blood) or CD45.1$^+$ (derived from the transplanted healthy competing bone marrow). To determine the phenotype of the blood, following red cell lysis, blood is stained with the following antibodies for phenotypic analysis: CD45.1-PE, CD45.2-FITC, CD11b-apc, B220-peCY7. The percentage of CD45.2$^+$ blood reconstitution in recipient mice is directly proportional to the number of CD45.2$^+$ HSC that were initially present in the volume of mobilized blood transplanted. For ease of interpretation, these data have been converted into the number of 'reconstitution units' (RU) measured per mL of blood[12]. One reconstitution unit is arbitrarily defined as the constant number of HSC present in 100,000 BM cells from healthy untreated mice. The number of RU in mobilized donor blood is calculated as follows: donor RU=% donor cells×C/(100−% donor cells) where C is the number of competing RU given together with the mobilized blood[12,13]. For example, if 25 µL of mobilized blood from a CD45.2$^+$ mouse injected in competition with 200,000 healthy CD45.1$^+$ bone marrow cells (2 competing RU) into a lethally-irradiated recipient resulted in a 50:50 reconstitution of CD45.2$^+$ and CD45.1$^+$ blood cells, then the number of reconstitution units in the original mobilized blood was 2. This method is standard for calculating the true HSC content in a donor sample. The number of actual long-term reconstituting HSC within 100, 000 healthy bone marrow cells (1 RU) is between 2-3 HSC.

Repeated Rounds of Cyclophosphamide Chemotherapy

Wild-type and E-selectin KO mice were first administered 8 consecutive rounds of chemotherapy. The chemotherapeutic agent used was the alkylating agent cyclophosphamide administered as a single intraperitoneal injection at 200 mg/kg. Mice were given 8 rounds of cyclophosphamide chemotherapy at fortnightly intervals, then left to recover for 6 weeks before administration of G-CSF (total 1 mg/kg as above) and blood collected 3 days later at HSC mobilization. Blood was analyzed for total leukocyte count, Colony forming cells and phenotypic HSC as described above.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

1. Alousi A, de Lima M. Reduced-intensity conditioning allogeneic hematopoietic stem cell transplantation. Clin Adv Hematol Oncol. 2007; 5:560-570.
2. Fruehauf S, Wermann K, Buss E C, et al. Protection of hematopoietic stem cells from chemotherapy-induced toxicity by multidrug-resistance 1 gene transfer. Recent Results Cancer Res. 1998; 144:93-115.
3. Bogden A E, Carde P, de Paillette E D, Moreau J P, Tubiana M, Frindel E. Amelioration of chemotherapy-induced toxicity by cotreatment with AcSDKP, a tetrapeptide inhibitor of hematopoietic stem cell proliferation. Ann N Y Acad Sci. 1991; 628:126-139.
4. Mauch P, Constine L, Greenberger J, et al. Hematopoietic stem cell compartment: acute and late effects of radiation therapy and chemotherapy. Int J Radiat Oncol Biol Phys. 1995; 31:1319-1339.
5. Bradford G B, Williams B, Rossi R, Bertoncello I. Quiescence, cycling, and turnover in the primitive hematopoietic stem cell compartment. Exp Hematol. 1997; 25:445-453.
6. Kiel M J, Yilmaz O H, Iwashita T, Yilmaz O H, Terhorst C, Morrison S J. SLAM family receptors distinguish hematopoietic stem and progenitor cells and reveal endothelial niches for stem cells. Cell. 2005; 121:1109-1121.
7. McKenzie J L, Takenaka K, Gan O I, Doedens M, Dick J E. Low rhodamine 123 retention identifies long-term human hematopoietic stem cells within the Lin-CD34+CD38- population
10.1182/blood-2006-06-030270. Blood. 2007; 109:543-545.
8. Winkler I G, Snapp K R, Simmons P J, Levesque J-P. Adhesion to E-selectin promotes growth inhibition and apoptosis of human and murine hematopoietic progenitor cells independent of PSGL-1. Blood. 2004; 103:1685-1692.
9. Maly P, Thall A, Petryniak B, et al. The alpha(1,3)fucosyltransferase Fuc-TVII controls leukocyte trafficking through an essential role in L-, E-, and P-selectin ligand biosynthesis. Cell. 1996; 86:643-653.
10. Katayama Y, Hidalgo A, Chang J, Peired A, Frenette P S. CD44 is a physiological E-selectin ligand on neutrophils. J Exp Med. 2005; 201:1183-1189.
11. Kiel M J, Yilmaz O H, Iwashita T, Yilmaz O H, Terhorst C, Morrison S J. SLAM family receptors distinguish hematopoietic stem and progenitor cells and reveal endothelial niches for stem cells. Cell. 2005; 121:1109-1121.
12. Purton L E, Scadden D T. Limiting factors in murine hematopoietic stem cell assays Cell Stem Cell. 2007; 1:262-270.
13. Harrison D E, Jordan C T, Zhong R K, Astle C M. Primitive hemopoietic stem cells: direct assay of most productive populations by competitive repopulation with simple binomial, correlation and covariance calculations. Exp Hematol. 1993; 21:206-219.

What is claimed is:
1. A method for enhancing hematopoiesis in a subject undergoing medical treatment with an agent that targets rapidly dividing cells and/or disrupts the cell cycle, the method comprising administering concurrently to the subject a mobilizer of hematopoietic stem cells or progenitor cells and an E-selectin antagonist in an effective amount to enhance hematopoiesis.

2. The method of claim 1, wherein the enhanced hematopoiesis comprises enhanced migration of stem cells from the bone marrow into the peripheral blood of the subject.

3. The method of claim 1, wherein the enhanced hematopoiesis comprises an increased number of hematopoietic stem cells or hematopoietic progenitor/precursor cells in the peripheral blood of the subject.

4. The method of claim 1, wherein the enhanced hematopoiesis comprises an increased number of granulocytes in the peripheral blood of the subject.

5. The method of claim 1, wherein the enhanced hematopoiesis comprises an increased number of neutrophils in the peripheral blood of the subject.

6. The method of claim 1, wherein the mobilizer and the antagonist are administered simultaneously to the subject.

7. The method of claim 1, wherein the E-selectin antagonist is administered to the subject prior to administration of the mobilizer.

8. The method of claim 1, wherein the E-selectin antagonist is administered after administration of the mobilizer to the subject.

9. A method for treating or preventing an immunocompromised condition in a subject, which condition results from exposure of the subject to a medical treatment that targets rapidly dividing cells and/or disrupts the cell cycle, the method comprising administering concurrently to the subject a mobilizer of hematopoietic stem cells or progenitor cells and an E-selectin antagonist in amounts effective for treatment or prevention the immunocompromised condition.

10. The method of claim 9, wherein the immunocompromised condition is selected from neutropenia, agranulocytosis, thrombocytopenia, and anemia.

11. The method of claim 9, further comprising identifying a subject having or at risk of developing the immunocompromised condition.

12. The method of claim 9, wherein the medical treatment is selected from chemotherapy and radiation therapy.

13. The method of claim 9, wherein the medical treatment comprises treatment or prophylaxis of a cancer or an autoimmune disease.

14. The method of claim 9, wherein the mobilizer and the E-selectin antagonist are administered over a period of time and in amounts which are effective for increasing the number of hematopoietic stem cells or progenitor cells and/or neutrophils in the peripheral blood of the subject.

15. The method of claim 9, wherein the mobilizer and the antagonist are administered simultaneously to the subject.

16. The method of claim 9, wherein the E-selectin antagonist is administered to the subject prior to administration of the mobilizer.

17. The method of claim 9, wherein the E-selectin antagonist is administered after administration of the mobilizer to the subject.

18. The method of claim 9, wherein the E-selectin antagonist and the mobilizer are administered concurrently to the subject simultaneously, sequentially or separately with the medical treatment.

19. The method of claim 9, wherein the concurrent administration of the E-selectin antagonist and the mobilizer is a prophylactic treatment.

20. The method of claim 9, wherein the concurrent administration of the E-selectin antagonist and the mobilizer is a therapeutic treatment.

21. The method of claim 9, further comprising exposing the subject to an ancillary treatment that treats or prevents the immunocompromised condition.

22. The method of claim 21, wherein the immunocompromised condition is neutropenia and the ancillary treatment suitably comprises administering to the subject a neutropenia medicament.

23. The method of claim 21, wherein the immunocompromised condition is neutropenia and the ancillary treatment suitably comprises administering to the subject a neutropenia medicament, wherein the neutropenia medicament is selected from the group consisting of a glucocorticoid, an immunoglobulin, an androgen, a recombinant IFNγ, and a uteroferrin.

24. The method of claim 21, wherein the ancillary treatment is administered to the subject simultaneously, sequentially or separately with the E-selectin antagonist or the mobilizer.

25. The method of claim 9, wherein the subject is preparing to undergo chemotherapy or radiation treatment.

26. The method of claim 9, wherein the subject has received at least one dose of chemotherapy or at least one radiation treatment.

* * * * *

UNITED STATES PATENT AND TRADEMARK OFFICE
CERTIFICATE OF CORRECTION

| | |
|---|---|
| PATENT NO. | : 9,254,322 B2 |
| APPLICATION NO. | : 12/747324 |
| DATED | : February 9, 2016 |
| INVENTOR(S) | : Jean-Pierre Levesque et al. |

It is certified that error appears in the above-identified patent and that said Letters Patent is hereby corrected as shown below:

Title page

In the Abstract, line 5, "particular" should read as --particularly--

Specification

Column 1, line 10, "particular" should read as --particularly--

Column 5, line 19, "from glucocorticoid, immunoglobulin" should read as --from a glucocorticoid, an immunoglobulin--

Column 6, line 57, "prior sacrifice" should read as --prior to sacrifice--

Column 7, lines 14 to 15, "PSGL-1-/- CD44-/- or CD44-/-/PSGL-/-" should read as --PSGL-1$^{-/-}$ CD44$^{-/-}$ or CD44$^{-/-}$/PSGL$^{-/-}$--

Column 10, line 12, "functional" should read as --functionally--

Column 11, line 38, "decent" should read as --descent--

Column 12, line 65, "includes" should read as --included--

Column 13, line 56, "sympfoms" should read as --symptoms--

Column 15, line 36, "repoiter" should read as --reporter--

Column 15, line 43, "(CAT) Assays" should read as --(CAT). Assays--

Signed and Sealed this
Twenty-sixth Day of July, 2016

Michelle K. Lee
*Director of the United States Patent and Trademark Office*

CERTIFICATE OF CORRECTION (continued)
U.S. Pat. No. 9,254,322 B2

Specification

Column 16, lines 17 to 18, "windows; available from Hitachi Software engineering" should read as --Windows™; available from Hitachi Software Engineering--

Column 17, line 60, "NaHPO4" should read as --NaHPO$_4$--

Column 17, line 62, "NaHPO4" should read as --NaHPO$_4$--

Column 18, line 2, "NaHPO4" should read as --NaHPO$_4$--

Column 18, line 4, "NaHPO4" should read as --NaHPO$_4$--

Column 18, line 11, "NaHPO4" should read as --NaHPO$_4$--

Column 18, line 13, "NaHPO4" should read as --NaHPO$_4$--

Column 19, lines 63 to 67, "For example, "E-selectin" shall mean the E-selecting gene, whereas "E-selectin" shall indicate the protein product or products generated from transcription and translation and alternative splicing of the "E-selectin" gene." should read as
--For example, "*E-selectin*" shall mean the E-selectin gene, whereas "E-selectin" shall indicate the protein product or products generated from transcription and translation and alternative splicing of the "*E-selectin*" gene.--

Column 26, lines 10 to 17, "[SEQ ID NO, 12] d-DITWDQLWDLMK; Dd-ITWDQLWDLMK; DOd-TWDQLWDLMK; DITWd-DQLWDLMK; DITWDQLWDd-LMK; DITWDQLWDLMd-K; and HITWDQLWNVMN; (amino acids 4-14 of SEQ ID NO: 5) ITWDQLWDLMK; (amino acids 3-14 of SEQ ID NO: 5) DITWDQLWDLMK" should read as --d-DITWDQLWDLMK [SEQ ID NO: 225]; Dd-ITWDQLWDLMK [SEQ ID NO: 226]; DId-TWDQLWDLMK [SEQ ID NO: 227]; DITWd-DQLWDLMK [SEQ ID NO: 228]; DITWDQLWDd-LMKU [SEQ ID NO: 229]; DITWDQLWDLMd-K [SEQ ID NO:230]; and HITWDQLWNVMN [SEQ ID NO: 12]; ITWDQLWDLMK [SEQ ID NO: 231] (amino acids 4-14 of SEQ ID NO: 5); DITWDQLWDLMK [SEQ ID NO: 232] (amino acids 3-14 of SEQ ID NO: 5)--

Column 29, lines 53-59, "DITWDQLWDLM (amino acids 3-13 of SEQ ID NO: 5); DITWDQLWDL (amino acids 3-12 of SEQ ID NO: 5); TWDQLWDLMK (amino acids 5-14 of SEQ ID NO: 5); and DITWDQLWDLMK-C(O)NH$_2$ (amino acids 3-14 of SEQ ID NO: 5) wherein d-indicates a D-amino acid and —C(O)NH$_2$ represents an amidated carboxy terminus [SEQ ID NO: 108]." should read as --DITWDQLWDLM [SEQ ID NO: 233] (amino acids 3-13 of SEQ ID NO: 5); DITWDQLWDL [SEQ ID NO: 234] (amino acids 3-12 of SEQ ID NO: 5); TWDQLWDLMK [SEQ ID NO: 235] (amino acids 5-14 of SEQ ID NO: 5); and DITWDQLWDLMK-C(O)NH$_2$ [SEQ ID NO: 108] (amino acids 3-14 of SEQ ID NO: 5) wherein d- indicates a D-amino acid and -C(O)NH$_2$ represents an amidated carboxy terminus.--

CERTIFICATE OF CORRECTION (continued)
U.S. Pat. No. 9,254,322 B2

Specification

Column 31, lines 5-6, "[SEQ ID NO: 126] DITChaDQLWbLMK-C(O)NH$_2$;" should read as --DITChaDQLWDLMK-C(O)NH$_2$ [SEQ ID NO: 126];--

Column 32, lines 53-54, "[SEQ ID NO, 173] Succ-rrWAQLWDLM(OCH$_3$)K-C(O)NH$_2$;" should read as --Succ-ITWAQLWDLM(OCH$_3$)K-C(O)NH$_2$ [SEQ ID NO: 173];--

Column 33, line 44 to column 34, line 23, "[SEQ ID NO: 196] N-Cbz, N-Me-ITW-C(O)NH$_2$; [SEQ ID NO: 197] Cbz-rr-[(Me) (DL)W]-C(O)NH$_2$; [SEQ ID NO: 198] N-Cbz, N-Me-ITWDQ-C(O)NH$_2$; [SEQ ID NO: 199] Cbz-ITW-N-Me-DQ-C(O)NH$_2$; [SEQ ID NO: 200] Cbz-rr-N-Me-WDQ-C(O)NH$_2$; [SEQ ID NO: 201] Cbz-I-(N-Me T)WDQ-C(O)NH$_2$; [SEQ ID NO: 202] Cbz-I-(N-Me-T)W-C(O)NH$_2$; [SEQ ID NO: 203] Cbz-IT-[(aMe) (DL)W]-DQ-C(O)NH$_2$; [SEQ ID NO: 204] Cbz -N-Me-I-T- [(aMe) (DL) W]-C(O) NH$_2$; [SEQ ID NO: 205] DITWDELWTLML; [SEQ ID NO: 206] HLTWDQLWRIMN; [SEQ ID NO: 207] HITWDQLWNLMN; [SEQ ID NO: 208] HITWDQLWDrMN; [SEQ ID NO: 209] HVTWELLWDIMN; [SEQ ID NO: 210] HITWGQLWDLMN; [SEQ ID NO: 211] HITWEQLWDLMN; [SEQ ID NO: 212] EITWFELWEWME; [SEQ ID NO: 213] MASWVLLWPYMG-C(O)NH$_2$; [SEQ ID NO: 214] DITWAQLWNIMN," should read as --N-Cbz, N-Me-ITW-C(O)NH$_2$; Cbz-IT-[(Me)(DL)W]-C(O)NH$_2$; N-Cbz, N-Me-ITWDQ-C(O)NH$_2$ [SEQ ID NO: 196]; Cbz-ITW-N-Me-DQ-C(O)NH$_2$ [SEQ ID NO: 197]; Cbz-IT-N-Me-WDQ-C(O)NH$_2$ [SEQ ID NO: 198]; Cbz-I-(N-Me T)WDQ-C(O)NH$_2$ [SEQ ID NO: 199]; Cbz-I-(N-Me-T)W-C(O)NH$_2$; Cbz-IT-[(aMe)(DL)W]-DQ-C(O)NH$_2$ [SEQ ID NO: 200]; Cbz-N-Me-I-T-[(aMe)(DL)W]-C(O)NH$_2$; DITWDELWTLML [SEQ ID NO: 201]; HLTWDQLWRIMN [SEQ ID NO: 202]; HITWDQLWNLMN[SEQ ID NO: 203]; HITWDQLWDTMN [SEQ ID NO: 204]; HVTWELLWDIMN [SEQ ID NO: 205]; HITWGQLWDLMN [SEQ ID NO: 206]; HITWEQLWDLMN [SEQ ID NO: 207]; EITWFELWEWME [SEQ ID NO: 208]; MASWVLLWPYMG-C(O)NH$_2$ [SEQ ID NO: 209]; DITWAQLWNIMN [SEQ ID NO: 210],--

Column 34, Lines 30-44, "Alternative peptide inhibitors of E-selectin are disclosed for example in US Pat. Appl. Pub. No 2005/0181987, which is expressly incorporated herein by reference in its entirety, and which discloses several peptido-mimetics which mimic the topography of the E-selectin ligand: ASAVNLYIPTQE [SEQ ID NO: 215], VYLAPGRISRDY [SEQ ID NO: 216], VYLAPGRFSRDY [SEQ ID NO: 217], CTSHWGVLSQRR [SEQ ID NO: 218], RVLSPESYLGPS [SEQ ID NO: 219], RVLSPESYLGPA [SEQ ID NO: 220], VGNGVLMGRRG [SEQ ID NO: 221], RVLSPESYLGPA [SEQ ID NO: 222], GNCRYIGLRQFG [SEQ ID NO: 223], DIRVEPGGGYTH [SEQ ID NO: 224], APIHTYTGRARG [SEQ ID NO: 225], and RHTCVRSCGHDR [SEQ ID NO: 226]." should read as --Alternative peptide inhibitors of E-selectin are disclosed for example in US Pat. Appl. Pub. No 2005/0181987, which is expressly incorporated herein by reference in its entirety, and which discloses several peptido-mimetics which mimic the topography of the E-selectin ligand: ASAVNLYIPTQE [SEQ ID NO: 211], VYLAPGRISRDY [SEQ ID NO: 212], VYLAPGRFSRDY [SEQ ID NO: 213], CTSHWGVLSQRR [SEQ ID NO: 214], RVLSPESYLGPS [SEQ ID NO: 215], RVLSPESYLGPA [SEQ ID NO: 216], VGNGVLMGRRG [SEQ ID NO: 217], RVLSPESYLGPA [SEQ ID NO: 218], GNCRYIGLRQFG [SEQ ID NO: 219], DIRVEPGGGYTH [SEQ ID NO: 220], APIHTYTGRARG [SEQ ID NO: 221], and RHTCVRSCGHDR [SEQ ID NO: 222].--

Specification

Column 36, line 65, "—$OSO_2^{2-}$" should read as -- —$OSO_2^{1-}$--

Column 37, line 2, "—$CH_2PO_3^{2}$" should read as -- —$CH_2PO_3^{2-}$--

Column 55, line 25, " 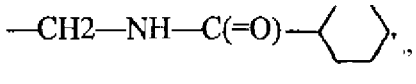 " should read as -- 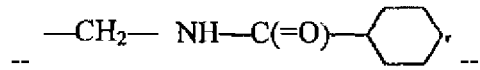 --

Column 114, line 37, "a E-selectin" should read as --an E-selectin--

Column 114, line 57, "amidification" should read as --amidation--

Column 116, line 15, "as agonist" should read as --as an agonist--

Column 117, line 31, "5-bromo-4-chloro-3-indoyl phosphate (BCIP)" should read as --5-bromo-4-chloro-3-indolyl phosphate (BCIP)--

Column 117, line 32, "3,3',4,4"-diamnobenzidine (DAB)" should read as --3,3',4,4"-diaminobenzidine (DAB)--

Column 117, line 63, "[SEQ ID NO: 227], which corresponds to GenBank accession" should read as --[SEQ ID NO: 223], which corresponds to GenBank accession--

Column 118, lines 16-17, "RGSSLKILSKGKRGGHSSVSTESESSSFHSS [SEQ ID NO: 228], which corresponds to GenBank accession number" should read as --RGSSLKILSKGKRGGHSSVSTESESSSFHSS [SEQ ID NO: 224], which corresponds to GenBank accession number--

Column 118, line 36, "G1" should read as --Gi--

Column 119, line 39, "(IL12)" should read as --(IL-12)--

Column 123, line 9, "drugs is" should read as --drug is--